(12) United States Patent
Yoo et al.

(10) Patent No.: US 10,583,206 B2
(45) Date of Patent: Mar. 10, 2020

(54) RADIOACTIVE PROBE FOR DETECTING HYDROGEN SULFIDE

(71) Applicant: KYUNGPOOK NATIONAL UNIVERSITY INDUSTRY-ACADEMIC COOPERATION FOUNDATION, Daegu (KR)

(72) Inventors: Jeong Soo Yoo, Daegu (KR); Swarbhanu Sarkar, Daegu (KR); Yeong Su Ha, Daegu (KR); Woong Hee Lee, Daegu (KR)

(73) Assignee: Kyungpook National University Industry-Academic, Cooperation Foundation, Daegu (KR)

( * ) Notice: Subject to any disclaimer, the term of this patent is extended or adjusted under 35 U.S.C. 154(b) by 0 days.

(21) Appl. No.: 15/564,214

(22) PCT Filed: Apr. 6, 2016

(86) PCT No.: PCT/KR2016/003559
§ 371 (c)(1),
(2) Date: Feb. 20, 2018

(87) PCT Pub. No.: WO2016/163727
PCT Pub. Date: Oct. 13, 2016

(65) Prior Publication Data
US 2018/0369428 A1 Dec. 27, 2018

(30) Foreign Application Priority Data
Apr. 7, 2015 (KR) .................. 10-2015-0049305

(51) Int. Cl.
| | | |
|---|---|---|
| *A61K 49/10* | (2006.01) | |
| *C07B 59/00* | (2006.01) | |
| *A61K 51/04* | (2006.01) | |
| *A61K 49/00* | (2006.01) | |
| *C07F 1/08* | (2006.01) | |
| *G01R 33/56* | (2006.01) | |

(52) U.S. Cl.
CPC ........ *A61K 49/106* (2013.01); *A61K 49/0002* (2013.01); *A61K 51/0478* (2013.01); *A61K 51/0482* (2013.01); *A61K 51/0491* (2013.01); *A61K 51/0497* (2013.01); *C07B 59/004* (2013.01); *C07F 1/08* (2013.01); *G01R 33/5601* (2013.01)

(58) Field of Classification Search
CPC .............. A61K 51/0482; A61K 49/106; A61K 51/0497; A61K 51/0478; A61K 51/0491; A61K 49/0002; C07B 59/004; C07F 1/08; G01R 33/5601
See application file for complete search history.

(56) References Cited

U.S. PATENT DOCUMENTS

2011/0027172 A1* 2/2011 Wang .................. A61K 31/337
424/1.29

FOREIGN PATENT DOCUMENTS

| CN | 101780286 A | 7/2010 |
|---|---|---|
| WO | WO 00/40585 | 7/2000 |
| WO | WO 02/26748 A2 | 4/2002 |
| WO | WO 2014/027820 A1 | 2/2014 |

OTHER PUBLICATIONS

Pauline Desogere. Synthesis and studies of new optimised chelating agents for targeting chemokine receptor CXCR4. Other. Université de Bourgogne, 2012. English. NNT : 2012DIJOS047. tel-00842206 (Year: 2012).*
Obata, A et al., "Retention mechanism of hypoxia selective nuclear imaging/radiotherapeutic agent Cu-diacetyl-bis(N 4-methylthiosemicarbazone) (Cu-ATSM) in tumor cells", *Annals of Nuclear Medicine*, vol. 15 No. 6, Dec. 2001, pp. 499-504 (6 pages in English).
Adonai, N et al., "Ex vivo cell labeling with 64Cu-pyruvaldehyde-bis(N4-methylthiosemicarbazone) for imaging cell trafficking in mice with positron-emission tomography", *Proceedings of the National Academy of Sciences*, vol. 99 No. 5, Mar. 2002, pp. 3030-3035 (8 pages in English).
Dehdasthi, F et al., "In vivo assessment of tumor hypoxia in lung cancer with 60Cu-ATSM", *European Journal of Nuclear Medicine and Molecular Imaging*, vol. 30 No. 6, Jun. 2003, pp. 844-850 (7 pages in English).
Extended European Search Report dated Nov. 23, 2018 in European Patent Application No. 16776830.8 (12 pages in English).
Jones-Wilson, T. et al., "The In Vivo Behavior of Copper-64-Labeled Azamacrocyclic Complexes", Nuclear Medicine & Biology, vol. 25, 1998, (pp. 523-530).
Yoo, J. et al., "Comparative in Vivo Behavior Studies of Cyclen-Based Copper-64 Complexes: Regioselective Synthesis, X-ray Structures, Radiochemistry, log P, and Biodistribution," J. Med. Chem. 2004, (pp. 6625-6637).

(Continued)

*Primary Examiner* — Michael G. Hartley
*Assistant Examiner* — Leah H Schlientz
(74) *Attorney, Agent, or Firm* — NSIP Law

(57) ABSTRACT

Provided is a probe for detecting in vivo hydrogen sulfide, specifically, a probe for detecting hydrogen sulfide including a complex compound into which a radioactive isotope Cu is introduced. According to specific embodiments of the present disclosure, as a result of real-time observing animal models, in which hydrogen sulfide involved in various diseases is generated in a large quantity, through optical and nuclear medicine imaging, the probe for detecting hydrogen sulfide according to the present disclosure may selectively bind with hydrogen sulfide to provide images of a site where hydrogen sulfide has abnormally increased in a cell or a tissue, thereby detecting a disease in an unexpected site without affecting the anatomical properties of the body. Accordingly, the probe may be effectively used as a means for diagnosing diseases, such as a composition for imaging, an imaging method, etc.

11 Claims, 44 Drawing Sheets

(56) References Cited

OTHER PUBLICATIONS

Sasakura, K. et al., "Development of a Highly Selective Fluorescene Probe for Hydrogen Sulfide", Journal of The American Chemical Society, 2011, (pp. 18003-18005).

Qu, X. et al., "A Red Fluorescent Turn-on Probe for Hydrogen Sulfide and its Application in Living Cells," The Royal Society of Chemistry, 2013, (pp. 7510-7512).

Pandya. D. et al., "New Bifunctional Chelator for 64u-Immuno-Positron Emission Tomography," Bioconjugate Chemistry, 2013, (pp. 1356-1366).

International Search Report and Written Opinion dated Feb. 2, 2017 in corresponding International Patent Application No. PCT/KR2016/003559. (10 pages in English and 28 pages in Korean).

Sun, Xiankai, et al. "Radiolabeling and In Vivo Behavior of Copper-64-Labeled Cross-Bridged Cyclam Ligands." *Journal of Medicinal Chemistry*, vol. 45, No. 2, Feb. 2002, pp. 469-477.

Liu, Yongjian, et al. "Molecular Imaging of Atherosclerotic Plaque With 64Cu-Labeled Natriuretic Peptide and PET." *Journal of Nuclear Medicine: Official Publication, Society of Nuclear Medicine*, vol. 51, Issue 1, Jan. 2010, pp. 85-91.

Xiao, Li, et al. "Synthesis of PECAM-1-Specific 64Cu PET Imaging Agent: Evaluation of Myocardial Infarction Caused by Ischemia-Reperfusion Injury in Mouse." *Bioorganic & Medicinal Chemistry Letters*, vol. 22, No. 12, Apr. 2012, pp. 4144-4147.

Lima, Luis MP, et al. "Monopicolinate Cyclen and Cyclam Derivatives for Stable Copper (II) Complexation," *Inorganic Chemistry*, vol. 51, No. 12, May 2012, pp. 6916-6927.

Stasiuk, Graeme J., et al. "The Ubiquitous DOTA and Its Derivatives: The Impact of 1, 4, 7, 10-Tetraazacyclododecane-1, 4, 7, 10-Tetraacetic Acid on Biomedical Imaging." *Chemical Communications*, vol. 49, issue Apr. 27, 2013, pp. 2732-2746.

Hickey, James L., et al. "Diagnostic Imaging Agents for Alzheimer's Disease: Copper Radiopharmaceuticals That Target Aβ Plaques," *Journal of the American Chemical Society*, vol. 135, No. 43, Oct. 2013, pp. 16120-16132.

Korean Office Action dated Jun. 1, 2017 in Corresponding Korean Patent Application No. 10-2017-0018121 (6 pages in Korean.).

Korean Office Action dated Sep. 18, 2017 in Corresponding Korean Patent Application No. 10-2017-0018121 (7 pages in Korean.).

* cited by examiner

FIG. 1
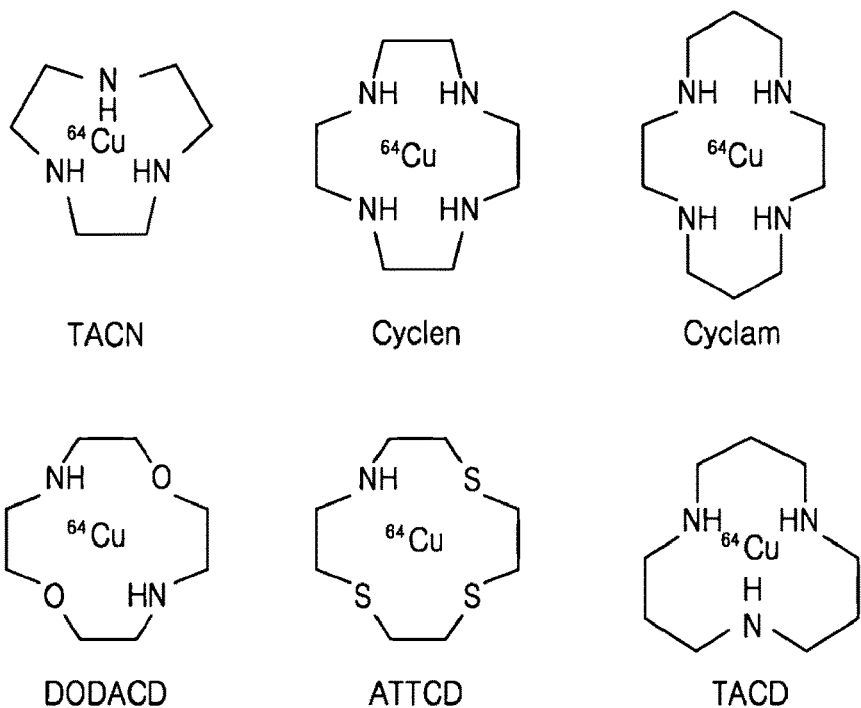
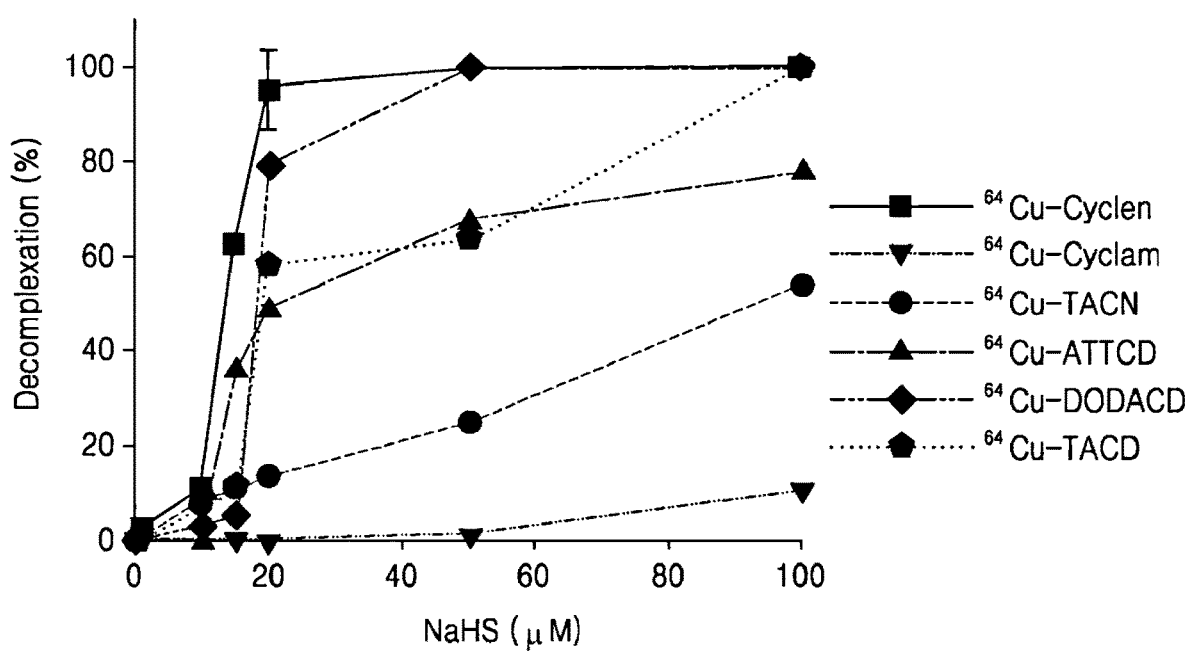

TLC: C-18 (MeOH:10% NH$_4$OAc [1:1])

$^{64}$Cu-TACN: 1.68 mCi

FIG. 7A
- CFA BALB/c mice (1day before)
4 h
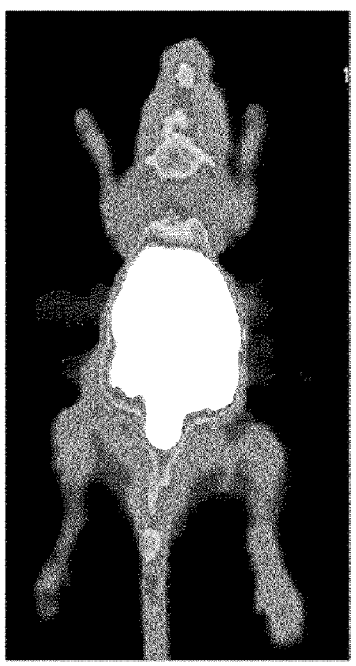
758 μCi
- Injection activity = 957 μCi
24 h
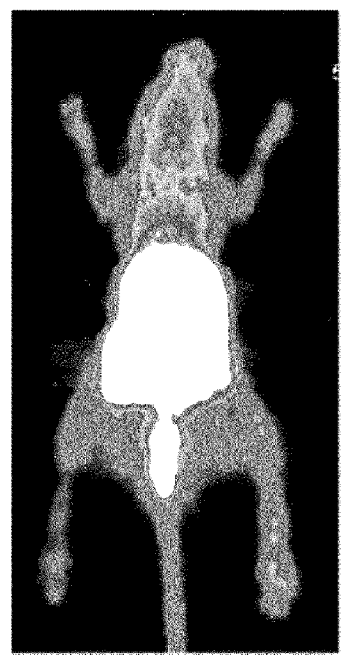
210 μCi FIG. 8C
Optical Image
4 h
Prone
Supine
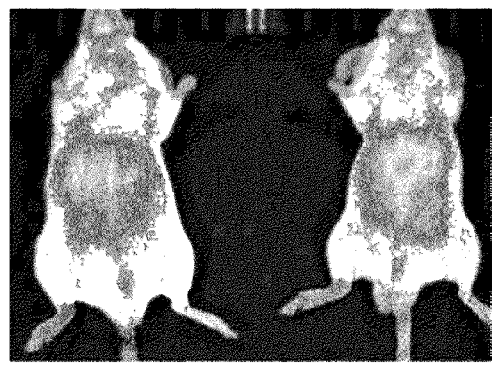
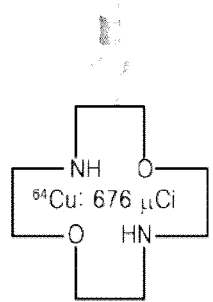
$^{64}$Cu: 676 μCi
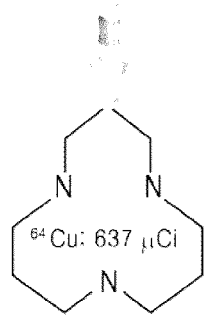
$^{64}$Cu: 637 μCi FIG. 11C
4 h post-injection
Prone
Supine
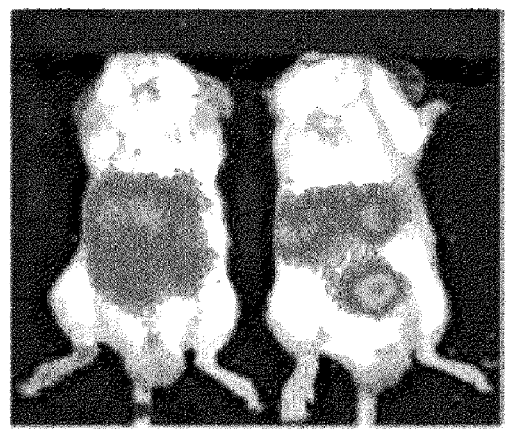

FIG. 11D
8 h post-injection          24 h post-injection
Prone                Prone                Supine
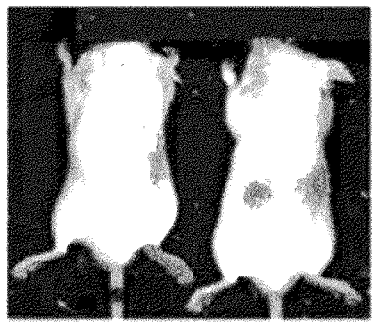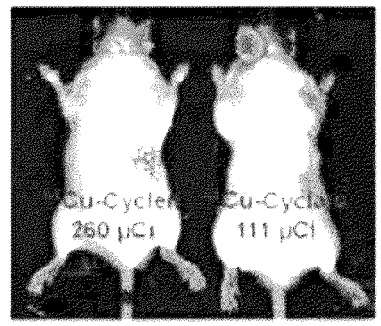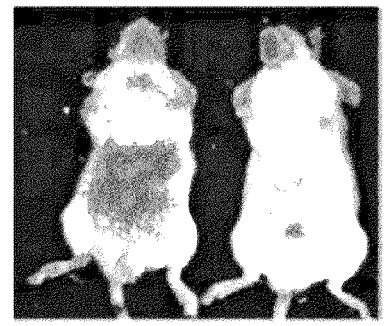

FIG. 14
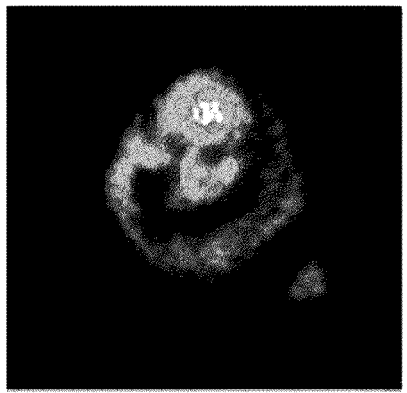  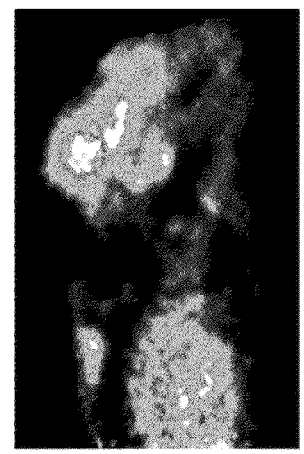
< Transverse >     < Coronal >     < Sagittal >

RADIOACTIVE PROBE FOR DETECTING HYDROGEN SULFIDE

CROSS REFERENCE TO RELATED APPLICATIONS

This application is a U.S. National Stage Application of International Application No. PCT/KR2016/003559, filed on Apr. 6, 2016, which claims the benefit under 35 USC 119(a) and 365(b) of Korean Patent Application No. 10-2015-0049305, filed on Apr. 7, 2015, in the Korean Intellectual Property Office.

TECHNICAL FIELD

The present disclosure relates to a probe for detecting in vivo hydrogen sulfide, and specifically, to a probe for detecting hydrogen sulfide including a complex compound into which a radioactive isotope Cu is introduced.

BACKGROUND ART

According to results of recent studies, hydrogen sulfide ($H_2S$) is known to be involved in various physiological phenomena as a $3^{rd}$ gasotransmitter and gasomediator, together with nitric oxide and carbon monoxide.

A level of hydrogen sulfide in blood plasma is known to be about 50 µM-100 µM, and results of recent studies reported that hydrogen sulfide acts as an important signaling molecule in many different physiological actions such as various inflammatory responses, cardiovascular diseases, vasodilation, glucose metabolism, neovascularization, etc., indicating that it is possible to diagnose a disease such as Down syndrome, Alzheimer's disease, diabetes, liver cirrhosis, etc. simply by detecting the level of hydrogen sulfide.

Particularly, hydrogen sulfide has attracted attention because it functions as a K-ATP channel opener, and contributes to homeostasis of the cardiovascular system, and plays a role in treating cardiac muscle damage. In this regard, WO 2014027820 A1 discloses a real-time biosignal measurement apparatus for cardiac ischemia and reperfusion, including a hydrogen sulfide sensor which detects hydrogen sulfide concentrations in real time.

Further, in vivo hydrogen sulfide is produced by three enzymes of cystathionine-synthase (CBS), cystathionine-lyase (CSE), and 3-mercaptopyruvate sulfurtransferase (3-MST), and hydrogen sulfide inhibits intracellular oxidative stress by inducing glutathione (GSH) which functions to protect cells by a cell immune system and an antioxidant action. Cytosolic hydrogen sulfide produced by CSE enters mitochondria via Katp channels under conditions of increased intracellular oxidative stress, and induces GSH, together with mitochondrial hydrogen sulfide produced by 3-MST and CAT enzymes, thereby protecting cells.

As such, since hydrogen sulfide induces changes of the GSH concentration to actually protect cells, it serves as a mediator preventing cell dysfunction and inhibiting apoptosis. Therefore, if detection of mitochondrial hydrogen sulfide and measurement of its concentration are possible, it will contribute to studying various life phenomena.

Accordingly, many technologies capable of detecting and quantifying hydrogen sulfide are being developed competitively, and in particular, development of a method of detecting in vivo hydrogen sulfide by non-invasive imaging has emerged as an important issue.

Although involvement of hydrogen sulfide in disease diagnosis and physiological phenomena has received attention and various types of probes are now being introduced, detection and accurate quantification of hydrogen sulfide are known to require very difficult and complex conditions such as measurement of $H_2S$ in a liquid state, selectivity for hydrogen sulfide over other anionic species, selectivity for hydrogen sulfide over reduced glutathione (GSH), etc.

In this regard, a method of detecting hydrogen sulfide by using a chromophore that utilizes chemical properties of intracellular cytosolic hydrogen sulfide and blood plasma hydrogen sulfide, a method of detecting hydrogen sulfide by passing a specific electrode through sulfide ions, and a method of detecting hydrogen sulfide by gas chromatography have been used until now. In recent years, various fluorescent probes have been developed. However, due to limitations of the fluorescent probe method, detection of hydrogen sulfide through imaging is very limited to a small animal level, and its application in practical bioimaging and studies on life phenomena is extremely restricted.

As a general fluorescent probe for detecting $H_2S$, a 2,4,6-triaryl pyridium cation compound was disclosed (Journal of the American Chemical Society, 125, 9000, 2003), but there is a problem that this compound cannot avoid competitive reaction with GSH. Further, a method of using 2,4 dinitrobenzene sulfonyl fluorescein as a fluorescence enhancement probe was suggested (Analytica Chimica Acta, 631, 91, 2009), but there is a problem that fluorescence intensity is changed over time due to hydrolysis of sulfonic acid ester.

In addition, an aminofluorescein compound (DPA-4-AF) having 2,2-dipicolylamine containing divalent copper ions ($Cu^{2+}$) was disclosed (Myung Gil Choi, et. al., Chem. Commun., (47), 7390-7392, 2009). A compound, in which a fluorescent material is attached to cyclen, cyclam, TACN, etc., is disclosed in WO2012-144654A1. This compound itself emits fluorescence, but it does not emit fluorescence by quenching of copper ions once binding with copper to form a complex compound. When hydrogen sulfide reacts with the complex compound, the copper complex is detached in a CuS form. Depending on the degree, fluorescence intensity to be restored differs. On the basis of this principle, a method of quantifying the amount of hydrogen sulfide was disclosed. However, this compound still has many problems in that images can be acquired only in vitro, and it is difficult to selectively detect hydrogen sulfide in vivo. Development of a new technology capable of replacing the known detection methods is still demanded.

DETAILED DESCRIPTION OF THE INVENTION

Technical Problem

An object to be achieved in the present disclosure is to provide a radioactive probe capable of selectively detecting in vivo/ex vivo hydrogen sulfide.

Technical Solution

According to one representative aspect of the present disclosure, provided is a probe for detecting hydrogen sulfide ($H_2S$), including a radioactive isotope Cu-introduced complex compound which is represented by any one of the following Chemical Formulae 1 to 4:

[Chemical Formula 1]

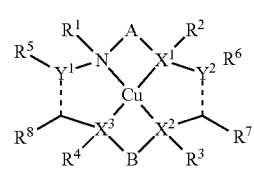

(wherein A, B, $X^1$ to $X^3$, $Y^1$, $Y^2$, and $R^1$ to $R^8$ are the same as disclosed herein)

[Chemical Formula 2]

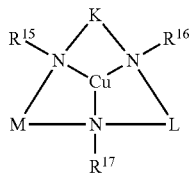

(wherein K, L, M, and $R^{15}$ to $R^{17}$ are the same as disclosed herein)

[Chemical Formula 3]

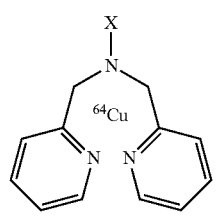

(wherein X is the same as disclosed herein)

[Chemical Formula 4]

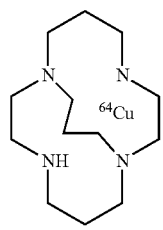

Advantageous Effects of the Invention

According to specific embodiments of the present disclosure, as a result of real-time observing animal models, in which hydrogen sulfide involved in various diseases is generated in a large quantity, through optical and nuclear medicine imaging, the probe for detecting hydrogen sulfide according to the present disclosure may selectively bind with hydrogen sulfide to provide images of a site where hydrogen sulfide has abnormally increased in a cell or a tissue, thereby detecting a disease in an unexpected site without affecting the anatomical properties of the body. In addition, the probe for detecting hydrogen sulfide quickly reacts with hydrogen sulfide, thereby solving the existing problem of waiting a predetermined time for testing after an imaging agent is injected. Accordingly, the probe may be effectively used as a means for diagnosing diseases, such as a composition for imaging, an imaging method, etc.

DESCRIPTION OF THE DRAWINGS

FIG. 1 shows a graph measuring hydrogen sulfide sensitivity of $^{64}$Cu-labeled complex compounds according to a specific embodiment of the present disclosure;

FIGS. 7A to 7D show results of imaging paw inflammation models injected with $^{64}$Cu-labeled complex compounds of Example 2 or Example 14 according to a specific embodiment of the present disclosure;

FIGS. 8A to 8E show results of imaging paw inflammation models injected with $^{64}$Cu-labeled complex compounds of Example 3 or Example 21 according to a specific embodiment of the present disclosure;

FIGS. 11A to 11D show results of imaging paw inflammation models injected with a $^{64}$Cu-labeled complex compound of Example 16 according to a specific embodiment of the present disclosure;

FIG. 14 shows result of imaging brain inflammation models injected with a $^{64}$Cu-labeled complex compound of Example 17 according to a specific embodiment of the present disclosure;

BEST MODE

Figure 2A:
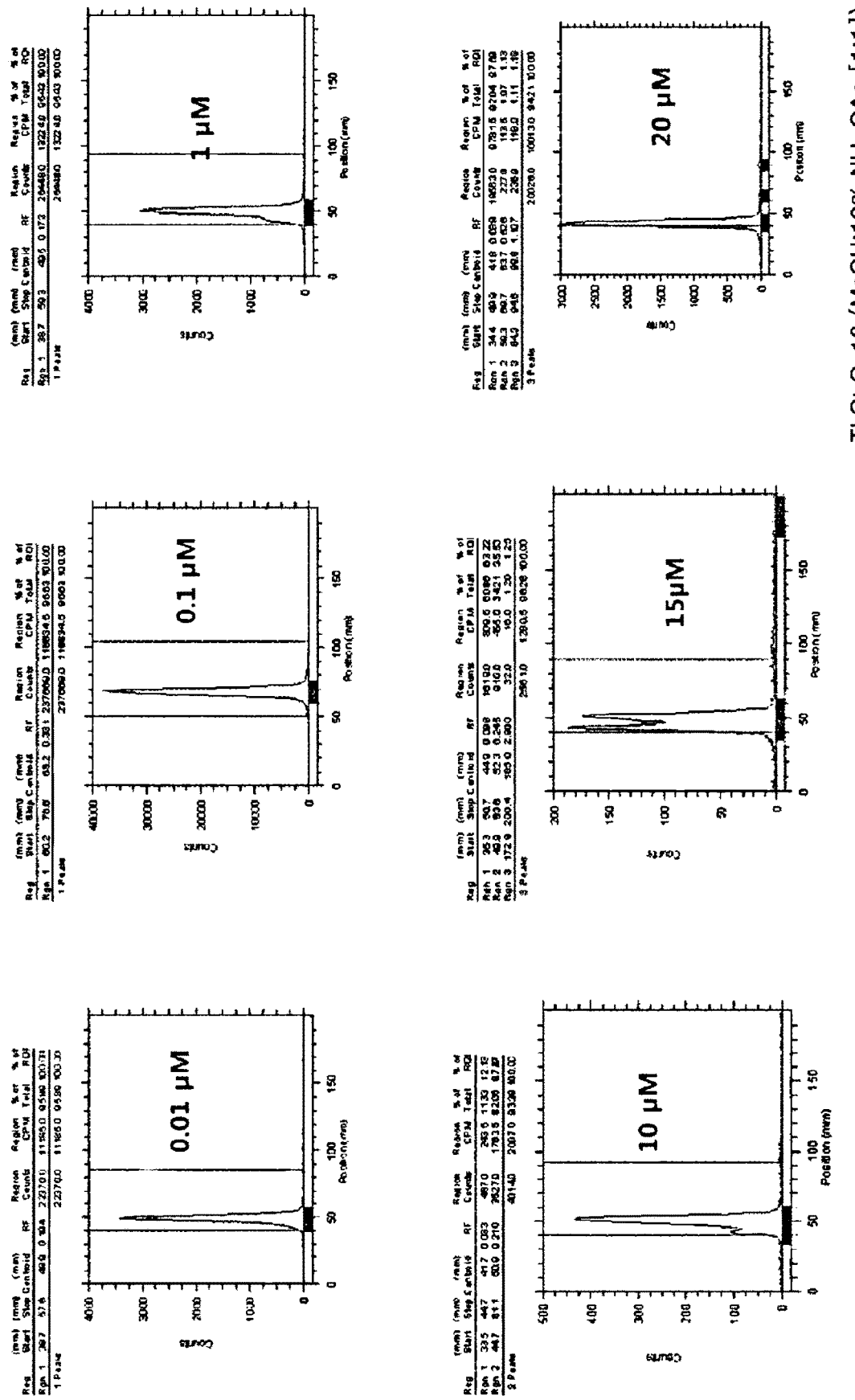
FIGS. 2A and 2B show results of measuring radio-TLC of $^{64}$Cu-labeled complex compounds according to a specific embodiment of the present disclosure.

Hereinafter, various aspects and specific embodiments of the present disclosure will be described in more detail.

As used herein, the term 'probe' is defined as a substance which is able to detect or image an in vivo/ex vivo target. In place of the term, an imaging agent, a contrast agent, a radiopharmaceutical, etc. is generally used.

According to an aspect of the present disclosure, disclosed is a probe for detecting hydrogen sulfide (H$_2$S), including a radioactive isotope Cu-introduced complex compound which is represented by any one of the following Chemical Formulae 1 to 4:

[Chemical Formula 1]

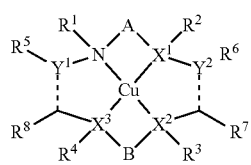

1

(wherein $X^1$, $X^2$ and $X^3$ are each independently one or more selected from N, O, and S;

$Y^1$ and $Y^2$ are each independently C or N;

A and B are each independently one or more selected from no bond, C(R$^9$)(R$^{10}$)—C(R$^{11}$)(R$^{12}$)—, =C(R$^9$)—C(R$^{10}$) (R$^{11}$)—C(R$^{12}$)(R$^{13}$)—, and C(R$^9$)(R$^{10}$)—C(R$^{11}$)(R$^{12}$)—C(R$^{13}$)(R$^{14}$)—, and =C(R$^9$)_C(R$^{10}$)=;

R$^1$ to R$^{14}$ are each independently one or more selected from no bond, hydrogen, hydroxy, substituted or unsubstituted C$_1$-C$_6$ linear or branched alkyl, substituted or unsubstituted C$_1$-C$_6$ linear or branched alkyloxycarbonyl, substituted or unsubstituted C$_5$-C$_{12}$ aryl C$_1$-C$_6$ alkyl, substituted or unsubstituted C$_5$-C$_{12}$ heterocycloalkyl, substituted or unsubstituted C$_5$-C$_{20}$ aryl, substituted or unsubstituted C$_5$-C$_{20}$ arylsulfonyl, C$_1$-C$_6$ alkylamine, C$_1$-C$_6$ dialkylamine, and substituted or unsubstituted amine, the 'substituted' means being substituted with one or more substituents selected from hydroxy, hydroxy C$_1$-C$_6$ alkyl, C$_1$-C$_6$ dialkylamine, nitro, and $^{64}$Cu-labeled 3-methyl-1,4,7,10-tetraazacyclotridecane, R$^5$ and R$^8$ or R$^6$ and R$^7$ bind to each other to form a C$_4$-C$_8$ cycloalkyl ring;

--- is a single bond or a double bond,

Cu is any one selected from $^{60}$Cu, $^{61}$Gu, $^{62}$Gu, $^{64}$Cu, and $^{67}$Cu);

[Chemical Formula 2]

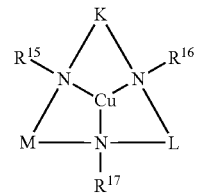

2

(wherein K, L and N are each independently one or more selected from C(R$^{18}$)(R$^{19}$)—C(R$^{20}$)(R$^{21}$)—, =C(R$^{18}$)—C(R$^{19}$)(R$^{20}$)—C(R$^{21}$)(R$^{22}$)—, C(R$^{18}$)(R$^{19}$)—C(R$^{20}$)(R$^{21}$)—C(R$^{22}$)(R$^{23}$)—, and =C(R$^{18}$)—C(R$^{19}$)=;

R$^{15}$ to R$^{23}$ are each independently one or more selected from no bond, hydrogen, hydroxy, substituted or unsubstituted C$_1$-C$_{20}$ linear or branched alkyl, substituted or unsubstituted C$_1$-C$_6$ linear or branched alkyloxycarbonyl, substituted or unsubstituted C$_5$-C$_{12}$ aryl C$_1$-C$_6$ alkyl, substituted or unsubstituted C$_5$-C$_{12}$ heterocycloalkyl, substituted or unsubstituted C$_5$-C$_{20}$ aryl, substituted or unsubstituted C$_5$-C$_{20}$ arylsulfonyl, C$_1$-C$_6$ alkylamine, C$_1$-C$_6$ dialkylamine, and substituted or unsubstituted amine, the 'substituted' means being substituted with one or more substituents selected from hydroxy, hydroxy C$_1$-C$_6$ alkyl, C$_1$-C$_6$ dialkylamine, nitro, and $^{64}$Cu-labeled 3-methyl-1,4,7,10-tetraazacyclotridecane;

Cu is any one selected from $^{60}$Cu, $^{61}$Cu, $^{62}$Cu, $^{64}$Cu, and $^{67}$Cu);

[Chemical Formula 3]

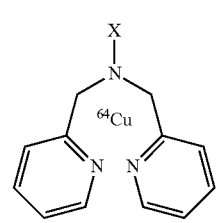

3

(wherein X is hydrogen or a compound represented by the following Chemical Formula)

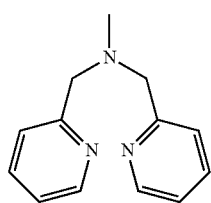

[Chemical Formula 4]

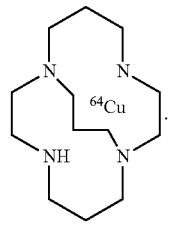

Preferably, the complex compound of Chemical Formula 1 is characterized by a complex compound represented by the following Chemical Formula 5 or 6:

[Chemical Formula 5]

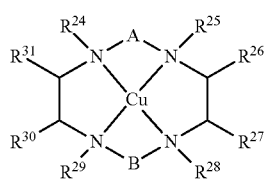

(wherein A or B is one or more selected from C(R$^{32}$)(R$^{33}$)—C(R$^{34}$)(R$^{35}$)—, =C(R$^{32}$)—C(R$^{33}$)(R$^{34}$)—C(R$^{35}$)(R$^{36}$)—, and C(R$^{32}$)(R$^{33}$)—C(R$^{34}$)(R$^{35}$)—C(R$^{36}$)(R$^{37}$)—, R$^{24}$ to R$^{37}$ are each independently one or more selected from no bond, hydrogen, hydroxy, $C_1$-$C_6$ linear or branched alkyl, $C_1$-$C_6$ linear or branched alkyloxycarbonyl, $C_1$-$C_6$ linear or branched alkylamine, substituted or unsubstituted amine, $C_5$-$C_{12}$ aryl $C_1$-$C_6$ alkyl substituted or unsubstituted with $^{64}$Cu-labeled 3-methyl-1,4,7,10-tetraazacyclotridecane or nitro, $C_5$-$C_{20}$ heterocycloalkyl substituted or unsubstituted with hydroxy or hydroxy $C_1$-$C_6$ alkyl, and $C_5$-$C_{20}$ arylsulfonyl substituted or unsubstituted with $C_1$-$C_6$ dialkylamine, R$^{26}$ and R$^{27}$ or R$^{30}$ and R$^{31}$ bind to each other to form a $C_4$-$C_8$ cycloalkyl ring;

Cu is any one selected from $^{60}$Cu, $^{61}$Gu, $^{62}$Gu, $^{64}$Cu, and $^{67}$Cu);

[Chemical Formula 6]

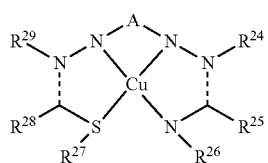

(wherein A is C(R$^{30}$)(R$^{31}$)—C(R$^{32}$)(R$^{33}$)— or =C(R$^{30}$)—C(R$^{31}$)=, R$^{24}$ to R$^{33}$ are each independently one or more selected from no bond, hydrogen, hydroxy, $C_1$-$C_6$ linear or branched alkyl, $C_1$-$C_6$ alkylamine, $C_1$-$C_6$ dialkylamine, and substituted or unsubstituted amine, --- is a single bond or a double bond, if --- is a double bond, R$^{24}$ or R$^{29}$ is no bond, Cu is any one selected from $^{60}$Cu, $^{61}$Cu, $^{62}$Cu, $^{64}$Cu, and $^{67}$Cu).

More preferably, the compound represented by any one of Chemical Formulae 1 to 4 is characterized by any one selected from (1) 1,4,7,10-tetraazacyclododecane;
(2) 1-(anthracen-9-ylmethyl)-1,4,7,10-tetraazacyclododecane;
(3) 1,7-dioxa-4,10-diazacyclododecane;
(4) 1,4,7,10-tetrakis(anthracen-9-ylmethyl)-1,4,7,10-tetraazacyclododecane;
(5) (7S,14R)-5,5,7,12,12,14-hexahexamethyl-1,4,8,11-tetraazacyclotetradecane;
(6) 2,5,5,7,9,12,12,14-octamethyl-1,4,8,11-tetraazacyclotetradecane;
(7) (1E,7E)-2,5,5,7,9,12,12,14-octamethyl-1,4,8,11-tetraazacyclotetradeca-7,14-diene;
(8) (7S,14S)-5,5,7,12,12,14-hexamethyl-1,4,8,11-tetraazacyclotetradecane;
(9) 6,15-dimethyldocosahydrodibenzo[b,i][1,4,8,11]tetraazacyclotetradecene;
(10) ethyl 3-(1,4,7,10-tetraazacyclododecan-1-yl)propanoate;
(11) 1,4-bis((1,4,7,10-tetraazacyclotridecan-4-yl)methyl)benzene;
(12) 2-(4-nitrobenzyl)-1,4,7,10-tetraazacyclododecane;
(13) 1,4,7,10-tetraazacyclotridecane;
(14) (2R,3S,4S,5R,6S)-2-(hydroxymethyl)-6-(1,4,7,10-tetraazacyclododecan-1-yl)tetrahydro-2H-pyran-3,4,5-triol;
(15) 5-((1,4,7,10-tetraazacyclododecan-1-yl)sulfonyl)-N,N-dimethylnaphthalene-1-amine;
(16) 1,4,8,11-tetraazacyclotetradecane;
(17) (2R,2'R,3S,3'S,4S,4'S,5R,5'R,6R,6'R)-6,6'-(1,4,7,10-tetraazacyclododecane-1,7-diyl)bis(2-(hydroxymethyl)tetrahydro-2H-pyran-3,4,5-triol);
(18) 1,4,7-triazonane;
(19) 1,5,9-triazacyclododecane;
(20) 5-((1,4,7-triazonan-1-yl)sulfonyl)-N,N-dimethylnaphthalene-1-amine;
(21) 1-methyl-1,4,8,11-tetraazacyclotetradecane;
(22) 1,4,8,11-tetraazabicyclo[6.6.3]heptadecane;
(23) bis(pyridin-2-ylmethyl)amine;
(24) N$^1$,N$^1$,N$^2$,N$^2$-tetrakis(pyridin-2-ylmethyl)ethane-1,2-diamine;
(25) (1Z,N'E)-N'-((E)-3-((bis(methylamino)methylene)hydrazono)butan-2-ylidene)-N-methylcarbamohydrazonothioic acid;
(26) (1Z,N'E)-N'-((E)-2-((bis(methylamino)methylene)hydrazono)propylidene)-N-methylcarbamohydrazonothioic acid;
(27) (2E,2'E,3R,3'R)-3-((3-(((R,E)-3-(hydroxyimino)butan-2-yl)amino)-2,2-dimethylpropyl)amino)butan-2-one oxime;
(28) 1,4,7-trithia-10-azacyclododecane;
(29) 1-methyl-1,4,7-triazonane;
(30) 1-(anthracen-9-ylmethyl)-1,4,7-triazonane;
(31) 1-hexadecyl-1,4,7-triazonane;
(32) 1,4,7-trimethyl-1,4,7-triazonane;
(33) 1,4,7-tris(anthracen-9-ylmethyl)-1,4,7-triazonane; and
(34) 1,4,7-trihexadecyl-1,4,7-triazonane.

The compound represented by any one of Chemical Formulae 1 to 4 is any one selected from
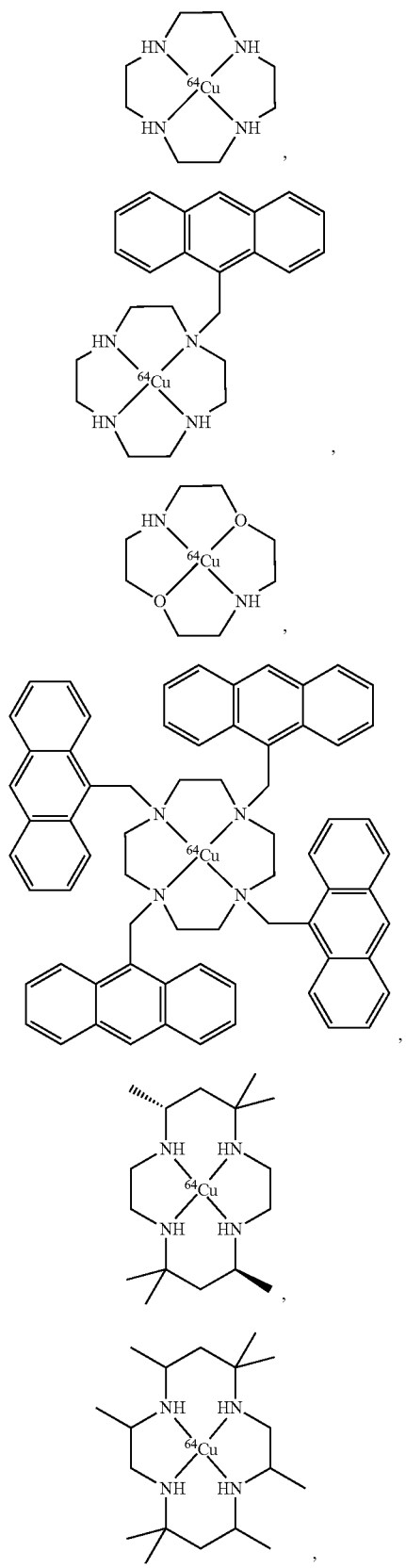
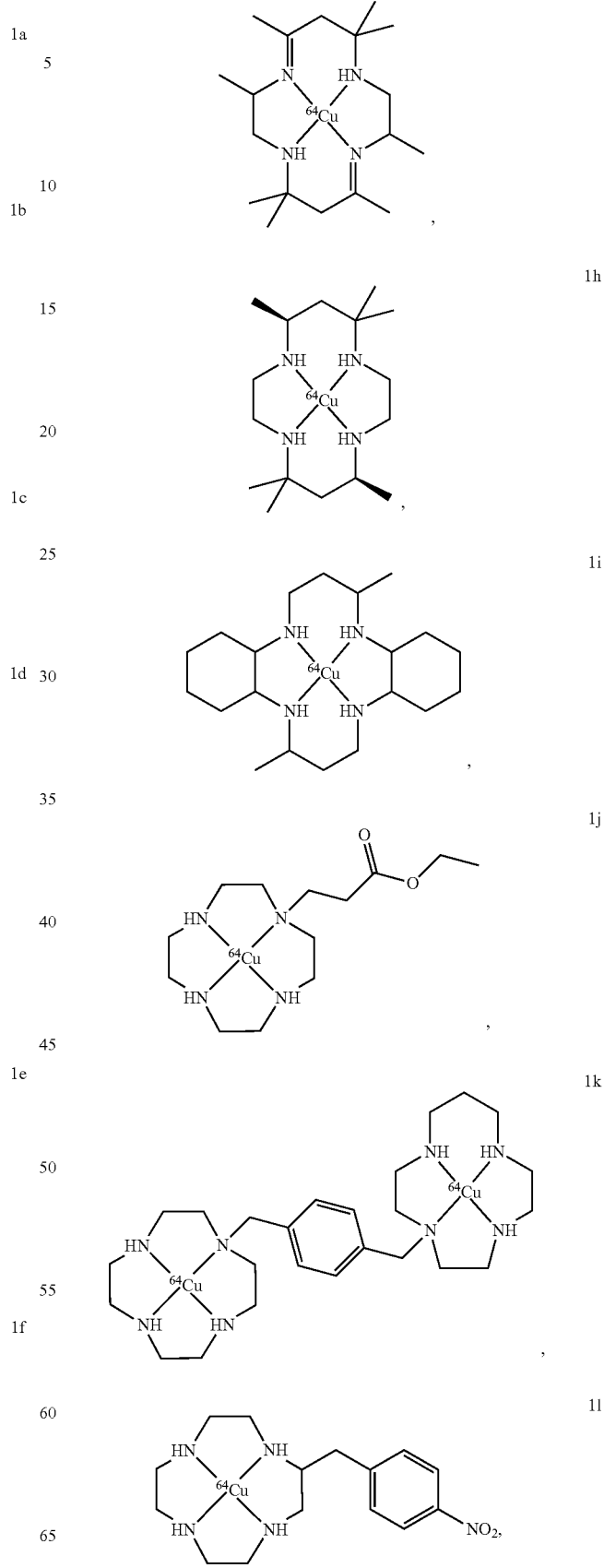

-continued
1m
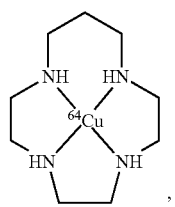
1n
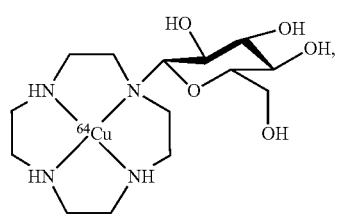
1o
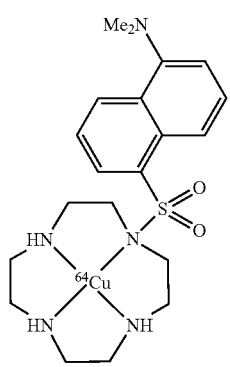
1p
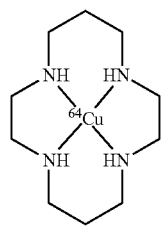
1q
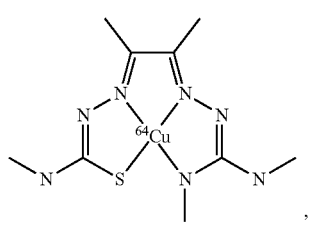
1r
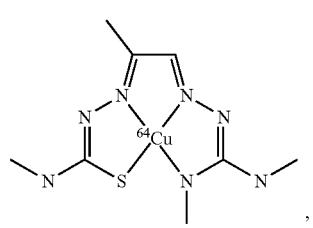
-continued
1r′
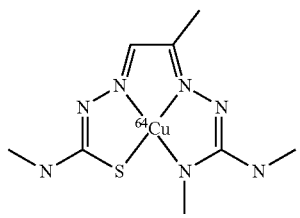
1s
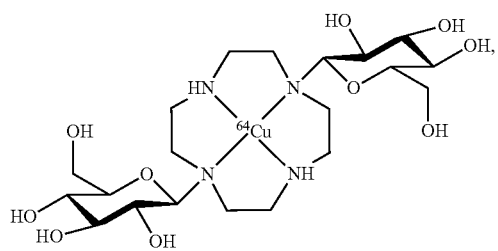
1t
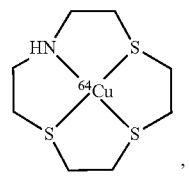
1u
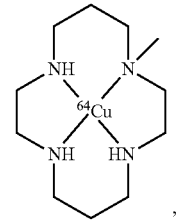
1w
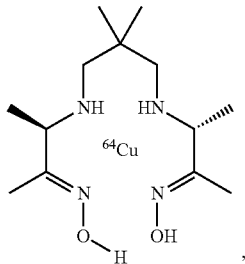
2a
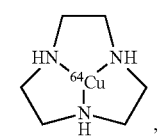
2b
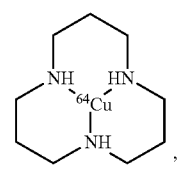

2c 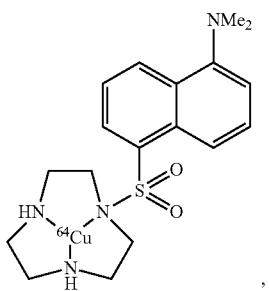

2d 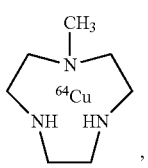

2e 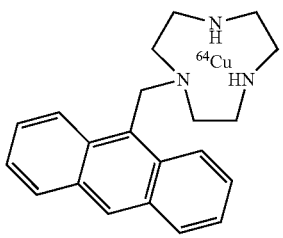

2f 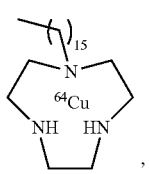

2g 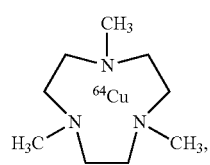

2h 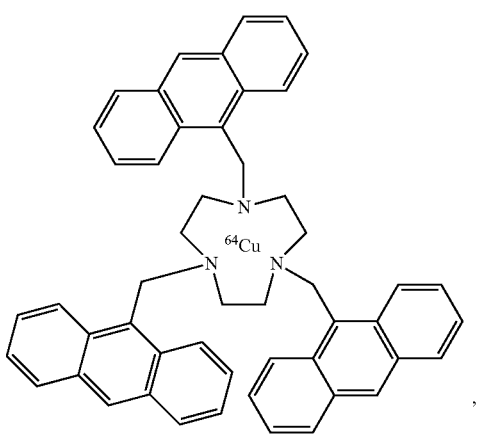

2i 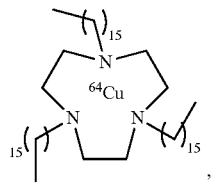

3a 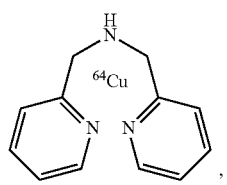

3b 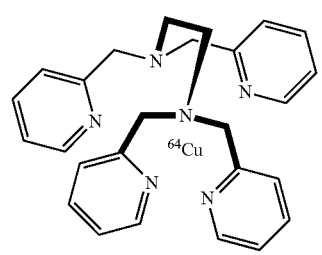

and

4 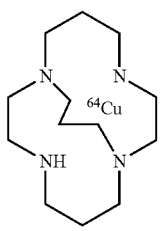

With regard to the radioactive isotope Cu-introduced complex compound represented by any one of Chemical Formulae 1 to 4 according to a specific embodiment of the present disclosure, as a result of real-time observing animal models, in which hydrogen sulfide involved in various diseases is generated in a large quantity, through optical and nuclear medicine imaging, the probe for detecting hydrogen sulfide according to the present disclosure may selectively bind with hydrogen sulfide and quickly reacts with hydrogen sulfide to provide images of a site where hydrogen sulfide has abnormally increased in a cell or a tissue, thereby detecting a disease in an unexpected site without affecting the anatomical properties of the body, and solving the existing problem of waiting a predetermined time for testing after an imaging agent is injected. Accordingly, the probe may be effectively used as a means for diagnosing diseases, such as a contrast agent for positron emission tomography (PET), a contrast agent for gamma camera, single photon emission computed tomography (SPECT), or Cherenkov optical imaging, a contrast agent for charge-coupled device (CCD), a contrast agent for magnetic resonance imaging (MRI), an imaging composition for computed tomography (CT), ultrasound (US), etc., or an imaging method.

In this regard, any one complex compound of Chemical Formulae 1 to 4 is preferably included in a dose of 50 μCi/kg-1000 μCi/kg, based on a dose immediately before use.

If the dose is out of the above range, there are additional problems that a signal-to-noise ratio is too low or the radiation exposure of a patient is excessively increased.

According to another aspect of the present disclosure, disclosed is a method of imaging sulfide ions in a cell or a tissue by using the probe for detecting hydrogen sulfide including the radioactive isotope Cu-introduced complex compound.

In a specific embodiment of the present disclosure, the imaging of sulfide ions is characterized by being performed by measuring Cherenkov radiation emitted from the radioactive isotope Cu.

In another specific embodiment of the present disclosure, Cherenkov radiation is characterized by having a wavelength of 200 nm to 1000 nm.

In still another specific embodiment of the present disclosure, the probe for detecting hydrogen sulfide including the radioactive isotope Cu-introduced complex compound is characterized by imaging sulfide ions in a site where hydrogen sulfide is abnormally increased or in a cell or extracellular matrix localized to the site, after being administered.

In still another specific embodiment of the present disclosure, disclosed is a method of detecting density of hydrogen sulfide, the method including introducing the probe for detecting hydrogen sulfide including the radioactive isotope Cu-introduced complex compound into a pharmaceutical carrier; injecting the probe into a mammal excluding a human; and scanning the mammal excluding a human by using a radiation imaging device.

In still another specific embodiment of the present disclosure, disclosed is a pharmaceutically acceptable pharmaceutical composition for diagnosing inflammatory diseases, including the probe for detecting hydrogen sulfide including the radioactive isotope Cu-introduced complex compound.

In a specific embodiment of the present disclosure, the inflammatory diseases are characterized by one or more selected from rheumatoid arthritis, non-rheumatoid inflammatory arthritis, Lyme disease-associated arthritis, inflammatory osteoarthritis, encephalomeningitis, osteomyelitis, inflammatory bowel disease, appendicitis, pancreatitis, sepsis, pyelitis, nephritis, and inflammatory diseases caused by bacterial infections.

In a specific embodiment of the present disclosure, as a result of conducting optical imaging and nuclear medicine imaging studies using animal models having induced paw inflammation, muscle inflammation, arthritis, or brain inflammation, selective uptake of the radioactive isotope Cu-introduced complex compound according to the present disclosure was observed in inflamed sites, and therefore, it may be effectively used as a pharmaceutical composition for diagnosing inflammatory diseases.

In still another specific embodiment of the present disclosure, disclosed is a pharmaceutically acceptable pharmaceutical composition for diagnosing cardiac diseases, including the probe for detecting hydrogen sulfide including the radioactive isotope Cu-introduced complex compound.

In a specific embodiment of the present disclosure, the cardiac diseases are characterized by one or more selected from myocardial infarction, cardiac ischemia, angina, cardiomyopathy, and endocarditis.

It is known that a myocardial infarction site has a high concentration of hydrogen sulfide. After induction of myocardial infarction by coronary artery occlusion in rats, the $^{64}$Cu-labeled complex compound according to the present disclosure was injected to the rats, and uptake in the myocardial infarction site was observed over time by imaging. As a result, when the radioactive isotope Cu-introduced complex compound according to a specific embodiment of the present disclosure was injected, high uptake in the myocardial infarction site was confirmed such that the myocardial infarction site was clearly observed in the image, indicating that the radioactive isotope Cu-introduced complex compound may be effectively used as a pharmaceutical composition for diagnosing cardiac diseases, as compared with FDG which is a known imaging agent to visualize cardiac muscles as partially broken rings when it is injected for imaging.

According to still another aspect of the present disclosure, disclosed is a pharmaceutically acceptable pharmaceutical composition for diagnosing Parkinson's disease, including the probe for detecting hydrogen sulfide including the radioactive isotope Cu-introduced complex compound.

According to still another aspect of the present disclosure, disclosed is a pharmaceutically acceptable pharmaceutical composition for diagnosing Alzheimer's disease, including the probe for detecting hydrogen sulfide including the radioactive isotope Cu-introduced complex compound.

According to still another aspect of the present disclosure, disclosed is a pharmaceutically acceptable pharmaceutical composition for diagnosing Down syndrome, including the probe for detecting hydrogen sulfide including the radioactive isotope Cu-introduced complex compound.

According to still another aspect of the present disclosure, disclosed is a pharmaceutically acceptable pharmaceutical composition for diagnosing tumors, including the probe for detecting hydrogen sulfide including the radioactive isotope Cu-introduced complex compound.

According to a specific embodiment of the present disclosure, the diagnosing of tumors is to diagnose hypoxia in tumors.

According to still another aspect of the present disclosure, disclosed is a pharmaceutically acceptable pharmaceutical composition for diagnosing sepsis, including the probe for detecting hydrogen sulfide including the radioactive isotope Cu-introduced complex compound.

According to still another aspect of the present disclosure, disclosed is a pharmaceutically acceptable pharmaceutical composition for diagnosing pains, including the probe for detecting hydrogen sulfide including the radioactive isotope Cu-introduced complex compound.

According to still another aspect of the present disclosure, disclosed is a pharmaceutically acceptable pharmaceutical composition for diagnosing arteriosclerosis, including the probe for detecting hydrogen sulfide including the radioactive isotope Cu-introduced complex compound.

According to still another aspect of the present disclosure, disclosed is a pharmaceutically acceptable pharmaceutical composition for diagnosing diabetes, including the probe for detecting hydrogen sulfide including the radioactive isotope Cu-introduced complex compound.

According to still another aspect of the present disclosure, disclosed is a pharmaceutically acceptable pharmaceutical composition for diagnosing stroke, including the probe for detecting hydrogen sulfide including the radioactive isotope Cu-introduced complex compound.

According to still another aspect of the present disclosure, disclosed is a pharmaceutically acceptable pharmaceutical composition for diagnosing liver cirrhosis, including the probe for detecting hydrogen sulfide including the radioactive isotope Cu-introduced complex compound.

According to still another aspect of the present disclosure, disclosed is a pharmaceutically acceptable pharmaceutical composition for diagnosing asthma, including the probe for detecting hydrogen sulfide including the radioactive isotope Cu-introduced complex compound.

According to still another aspect of the present disclosure, disclosed is a pharmaceutically acceptable pharmaceutical composition for diagnosing Parkinson's disease, including the probe for detecting hydrogen sulfide including the radioactive isotope Cu-introduced complex compound.

According to still another aspect of the present disclosure, disclosed is a kit for preparing a radioactive isotope Cu-labeled drug which is a sterile non-pyrogenic sealed form of a solution, frozen, or lyophilized state, including 1 ng to 100 mg of the probe for detecting hydrogen sulfide including the radioactive isotope Cu-introduced complex compound or a pharmaceutically acceptable salt thereof.

In an aspect of the present disclosure, the kit for preparing the drug is characterized by further including 0.01 mL-10 mL of a buffer solution at pH 1-9 and a concentration of 1 µM-10 µM.

In another aspect of the present disclosure, the buffer solution is characterized by acetic acid, phosphoric acid, citric acid, fumaric acid, butyric acid, succinic acid, tartaric acid, carbonic acid, glucoheptonic acid, gluconic acid, glucuronic acid, glucaric acid, boric acid, or a sodium salt or potassium salt thereof.

According to still another aspect of the present disclosure, disclosed is a method of early diagnosing a disease in an animal excluding a human by examining whether a hydrogen sulfide concentration is rapidly increased or decreased as compared with that of a normal state by measuring the hydrogen sulfide concentration in the blood or tissue using the radioactive isotope Cu-introduced complex compound.

Hereinafter, the present disclosure will be described in more detail with reference to Examples, etc. However, these examples should not be construed as narrowing or limiting the scope and content of the present disclosure. Further, it will be apparent that a person of ordinary skill in the art can easily implement the present invention, of which specific experimental results are not suggested, on the basis of the disclosure of the present invention including the following Examples, and changes and modifications also belong to the scope of the appended claims of the present invention.

MODE OF THE INVENTION

Synthesis of Various Chelates

Synthesis of (2R,3S,4S,5R,6R)-2-(hydroxymethyl)-6-(1,4,7,10-tetraazacyclododecan-1-yl)tetrahydro-2H-pyran-3,4,5-triol (CyclenGlc)

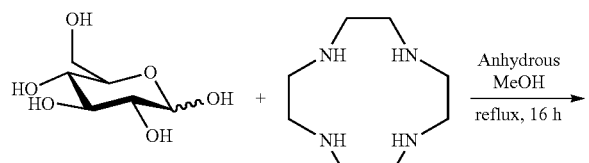

Cyclen (240 mg, 1.4 mmol) was added to a stirred solution of glucose (50 mg, 0.28 mmol) in anhydrous MeOH (10 mL), and the resulting solution was heated under reflux for 16 hours under $N_2$ atmosphere. Complete consumption of the starting materials was confirmed by TLC [stationary phase=C-18 TLC, mobile phase=MeOHL:10% $NH_4OAc$ (1:1)]. Then, the solvent was evaporated to dryness under reduced pressure and column chromatography was used to obtain a pure compound (52 mg, 56%). $^1H$ NMR ($D_2O$, 400 MHz): δ1.8 (s, 3H), 2.60-3.02 (m, 17H), 3.24-3.42 (m, 6H), 3.58-3.63 (m, 1H), 3.78 (d, J=12.0 Hz, 1H), 4.00 (d, J=8.4 Hz, 1H); $^{13}C$ NMR ($D_2O$, 100 MHz): δ43.67, 44.97, 45.92, 46.85, 49.18, 61.08, 69.96, 70.29, 77.47, 91.69; HRMS (FAB): m/z calcd for $C_{14}H_{30}N_4O_5$ [M+H] 335.2294; found 335.2296.

Synthesis of ethyl 3-(1,4,7,10-tetraazacyclododecan-1-yl)propanoate

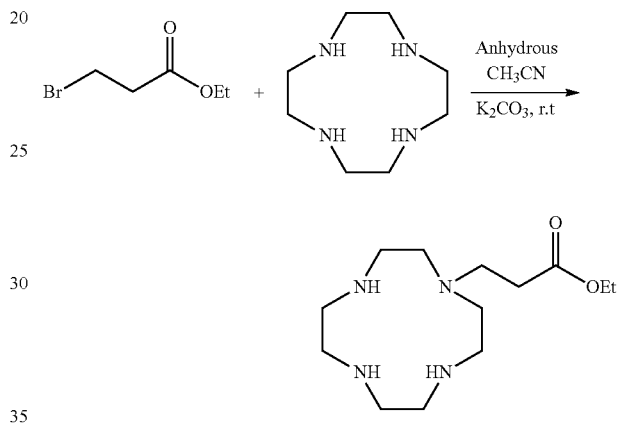

$K_2CO_3$ (300 mg, 2.2 mmol) and ethyl 3-bromopropanoate (100 mg, 0.61 mmol) were added to a stirred solution of cyclen (380 mg, 2.2 mmol) in anhydrous $CH_3CN$ (10 mL), and the resulting solution was stirred at room temperature for 16 hours under $N_2$ atmosphere. Complete consumption of the starting materials was confirmed by TLC [stationary phase=Basic alumina TLC, mobile phase=$CH_2Cl_2$:MeOH (10:1)]. The resulting product was separated from $K_2CO_3$ by filtration, and evaporated to dryness under reduced pressure. Column chromatography was used to obtain a pure compound (100 mg, 64%). $^1H$ NMR ($CDCl_3$, 400 MHz): δ1.27 (t, J=7.2 Hz, 3H), 2.38-2.57 (m, 10H), 2.64-2.67 (m, 4H), 2.76-2.84 (m, 6H), 4.07-4.18 (m, 2H); $^{13}C$ NMR ($CDCl_3$, 100 MHz): δ14.10, 32.55, 44.38, 45.64, 46.39, 49.61, 50.92, 60.31, 172.67.

Synthesis of 1,4,7,10-tetrakis(anthracen-9-ylmethyl)-1,4,7,10-tetraazacyclododecane

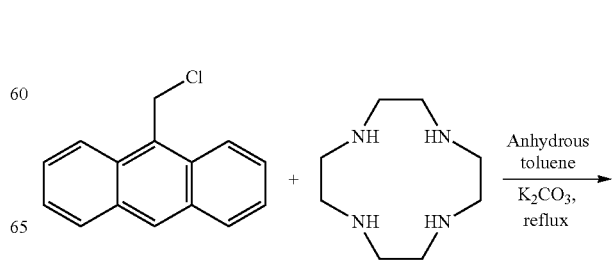

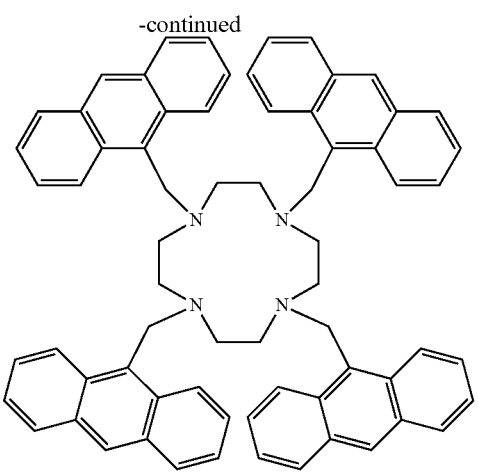

K$_2$CO$_3$ (400 mg, 2.9 mmol) and 9-(chloromethyl)anthracene (655 mg, 2.9 mmol) were added to a stirred solution of cyclen (100 mg, 0.58 mmol) in anhydrous toluene (15 mL), and the resulting solution was heated under reflux for 16 hours under N$_2$ atmosphere. Formation of a new product was confirmed by TLC [stationary phase=Silica TLC, mobile phase=EtOAc]. The resulting product was evaporated to dryness under reduced pressure and dichloromethane (50 mL) was added. The resulting product was shaken well with water and the separated organic layer was dried over MgSO$_4$. Column chromatography was used to obtain a pure compound (270 mg, 50%). $^1$H NMR (CDCl$_3$, 400 MHz): δ2.42 (s, 16H), 4.45 (s, 8H), 7.43-7.65 (m, 16H), 7.81-8.09 (m, 10H), 8.32-8.48 (m, 10H); $^{13}$C NMR (CDCl$_3$, 100 MHz): δ45.28, 51.02, 54.68, 123.86, 124.60, 125.15, 126.52, 126.82, 127.38, 128.44, 129.31, 129.51, 131.44, 131.49, 131.51, 134.28.

Synthesis of 1-(anthracen-9-ylmethyl)-1,4,7,10-tetraazacyclododecane

Chloromethylanthracene (1.0 equiv.) was dissolved in toluene (5 mL), and cyclen (5.0 equiv.) was added thereto. The resulting solution was heated under reflux for 8 hours. $^1$H NMR (CDCl$_3$, 400 MHz): δ2.04 (s, 3H, NH), 2.44-2.47 (m, 8H), 2.84-2.94 (m, 8H), 4.75 (s, 2H), 7.46-7.59 (m, 4H), 8.01-8.03 (m, 2H), 8.45-8.51 (m, 3H).

Synthesis of 5-((1,4,7,10-tetraazacyclododecan-1-yl)sulfonyl)-N,N-dimethylnaphthalene-1-amine

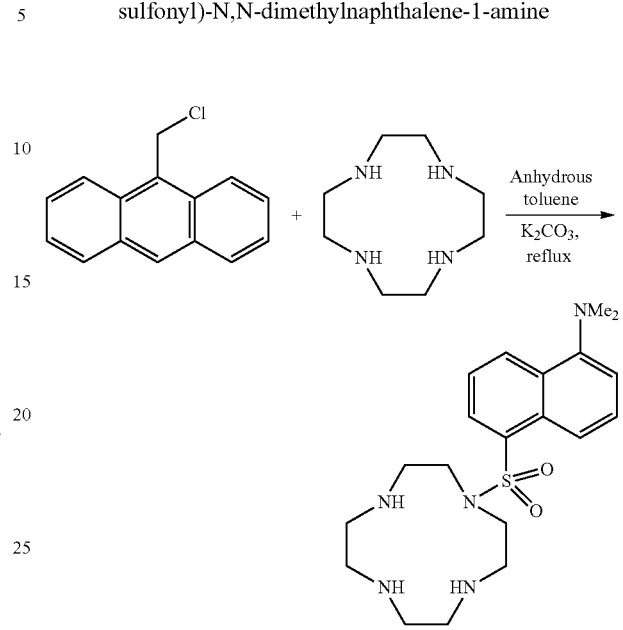

Dansyl chloride (1.0 equiv.) was dissolved in toluene (5 mL), and then cyclen (5.0 equiv.) was added thereto. The resulting solution was stirred at room temperature for 2 hours. Precipitated salts were removed, and an organic phase was separated and dried. The solid was purified by column chromatography. $^1$H NMR (CDCl$_3$, 400 MHz): δ2.00-2.04 (m, 3H), 2.89 (s, 6H), 3.11-3.88 (m, 16H), 7.20 (d, J=7.6 Hz, 1H), 7.50-7.59 (m, 2H), 7.92 (d, J=7.2 Hz, 1H), 8.34 (d, J=8.4 Hz, 1H), 8.57 (d, J=8.8 Hz, 1H)); $^{13}$C NMR (CDCl$_3$, 100 MHz): δ45.47, 47.37, 49.95, 50.74, 51.90, 115.67, 118.90, 123.12, 127.97, 128.75, 130.28, 130.56, 131.03, 132.84, 152.07.

Synthesis of 1,4,7-trithia-10-azacyclododecane

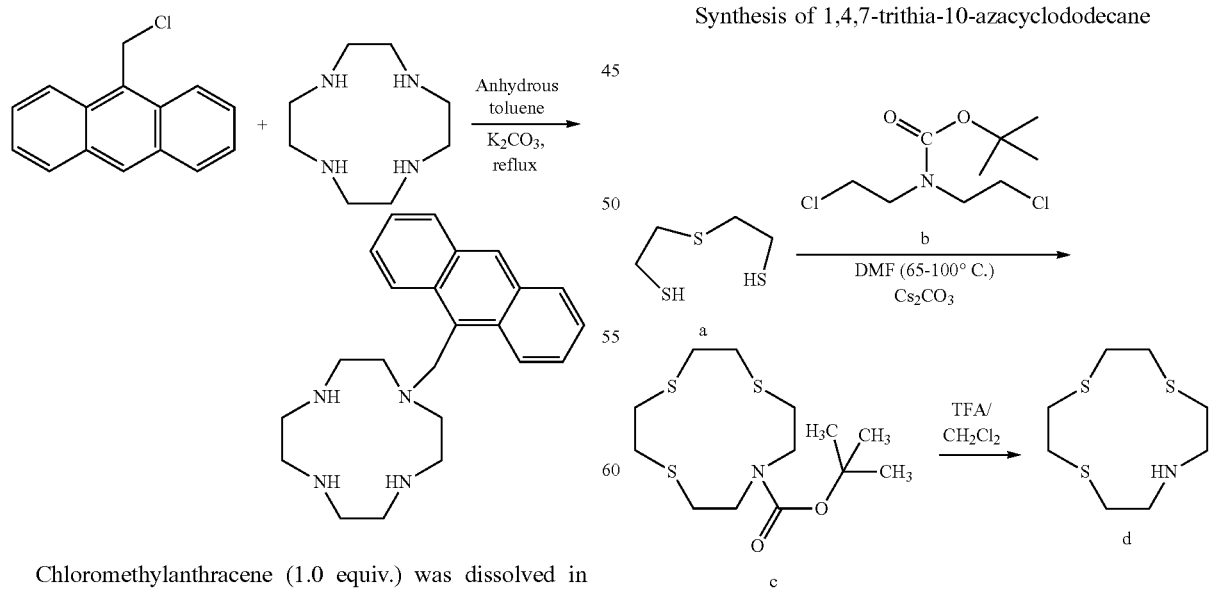

Step I: 3-thia-1,5-pentanedithiol (a, 1 equiv.) in DMF and N-boc-bis(2-chloroethyl)amine (b, 1 equiv.) were slowly added and $Cs_2CO_3$ (1.5 equiv.) was also added, and allowed to react for 96 hours at 65° C. to prepare N-Boc-[12]aneNS3 (c). The solvent was removed under vacuum, and the resulting product was dissolved in $CH_2Cl_2$ and washed with water to remove cesium salts. The product was dried over $MgSO_4$, and subjected to filtration and evaporation processes. The resulting product was purified by recrystallization with warm toluene to obtain a white crystal of Nboc-[12]aneNS3 (c).

Step II: N-Boc-[12]aneNS3 (c) was deprotected with a mixture of TFA and $CH_2Cl_2$ (1:1) at room temperature for 15 minutes. Excess TFA and $CH_2Cl_2$ were evaporated, and then water was added, and pH of the resulting product was adjusted to 14 by using $Na_2CO_3$ and NaOH. Thereafter, the mixture was extracted with $CH_2Cl_2$, and dried over $MgSO_4$, and subjected to filtration and evaporation processes to obtain a white crystal of [12]aneNS3. $^1H$ NMR ($CDCl_3$, 400 MHz): $\delta$2.71-2.91 (m, 16H), 3.98 (brs, 1H); $^{13}C$ NMR ($CDCl_3$, 100 MHz): $\delta$ 49.75, 32.37, 31.83, 31.56.

Synthesis of (1Z,N'E)-N'-((E)-3-((bis(methylamino) methylene)hydrazono)butan-2-ylidene)-N-methyl- carbamohydrazonothioic Acid

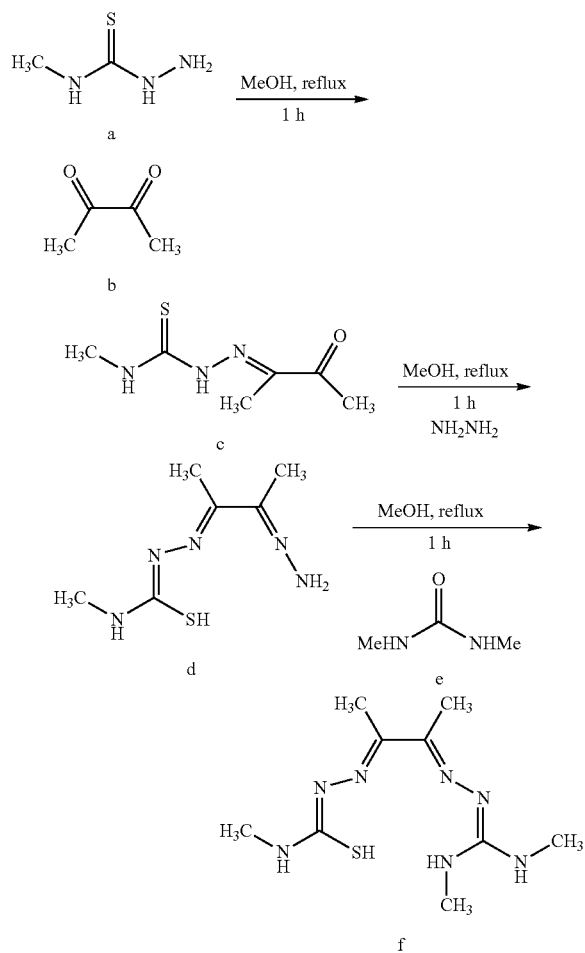

Step I: Semicarbazide (1.0 equiv.) and 2,3-butadione (10 equiv.) were first mixed in MeOH (10 mL), and the resulting product was refluxed for 1 hour to obtain a compound c, which was then purified by column chromatography.

Step II: The compound c (1 equiv.) was first mixed with hydrazine hydrate (10 equiv.) in MeOH (10 mL), and then the resulting product was refluxed for 1 hour to obtain a compound d, which was then purified by column chromatography.

Step III: The compound d (1 equiv.) was first mixed with N,N-dimethyl urea (1 equiv.) in MeOH (10 mL), and then the resulting product was refluxed for 1 hour to obtain a compound f. The solvent was dried and the compound f was purified by column chromatography to obtain a pure compound f. $^1H$ NMR (DMSO-$d_6$, 400 MHz): $\delta$1.574 (s, 1H), 1.85 (s, 1H), 1.95 (s, 1H), 2.02 (s, 3H), 2.19 (s, 6H), 3.03 (s, 3H), 3.04 (s, 3H), 3.13 (s, 1H).

Synthesis of 1-methyl-1,4,7-triazonane

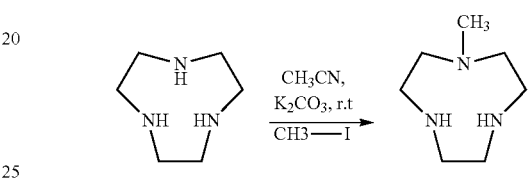

Potassium carbonate (27 mg, 0.19 mmol) and methyl iodide (28 mg, 0.19 mmol) were added to a stirred solution of TACN (100 mg, 0.78 mmol) in anhydrous acetonitrile (10 mL), and the resulting solution was stirred at room temperature for 16 hours. Formation of a new product was confirmed by TLC [stationary phase=Silica TLC, mobile phase=dichloromethane:IPA (10:1)]. The product was diluted with acetonitrile, and separated from potassium carbonate by using a filter, and evaporated to dryness under reduced pressure to obtain 1-methyl-1,4,7-triazonane. HR-MS (FAB) m/z calculated value $C_7H_{17}N_3[M+H]^+$ 144.1501, measured value 144.1501.

Synthesis of 1-(anthracen-9-ylmethyl)-1,4,7-triazonane

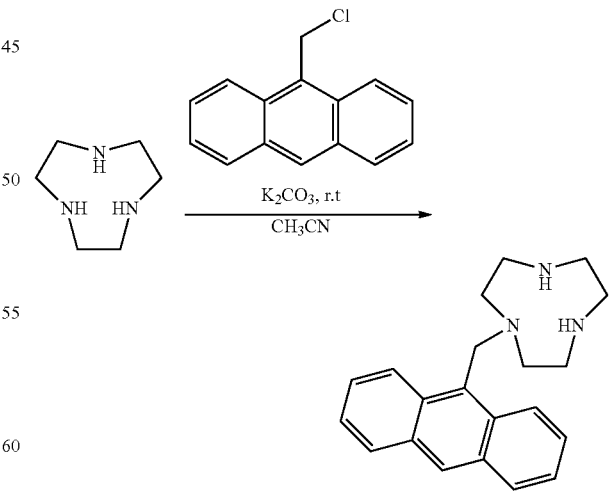

Potassium carbonate (27 mg, 0.19 mmol) and 9-(chloromethyl)anthracene (43 mg, 0.19 mmol) were added to a stirred solution of TACN (100 mg, 0.78 mmol) in anhydrous acetonitrile (10 mL), and the resulting mixture was stirred at room temperature for 16 hours. Formation of a new product was confirmed by TLC [stationary phase=Silica TLC, mobile phase=dichloromethane:IPA (10:1)]. The product was diluted with acetonitrile, and separated from potassium carbonate by using a filter, and evaporated to dryness under reduced pressure to obtain 1-(anthracen-9-ylmethyl)-1,4,7-triazonane. HR-MS(FAB) m/z calculated value $C_{21}H_{25}N_3$ [M+H]$^+$ 320.2127, measured value 320.2127.

Synthesis of 1-hexadecyl-1,4,7-triazonane

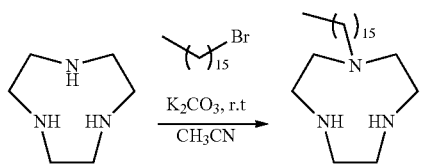

Potassium carbonate (27 mg, 0.19 mmol) and 1-bromohexadecane (58 mg, 0.19 mmol) were added to a stirred solution of TACN (100 mg, 0.78 mmol) in anhydrous acetonitrile (10 mL), and the resulting solution was stirred at room temperature for 16 hours. Formation of a new product was confirmed by TLC [stationary phase=Silica TLC, mobile phase=dichloromethane:IPA (10:1)]. The product was diluted with acetonitrile, and separated from potassium carbonate by using a filter, and evaporated to dryness under reduced pressure to obtain 1-hexadecyl-1,4,7-triazonane. HR-MS(FAB) m/z calculated value $C_{22}H_{47}N_3$[M+H]$^+$ 354.3848, measured value 354.3848.

Synthesis of 1,4,7-trimethyl-1,4,7-triazonane

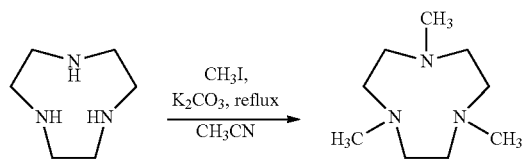

Potassium carbonate (433 mg, 3.12 mmol) and methyl iodide (443 mg, 3.12 mmol) were added to a stirred solution of TACN (100 mg, 0.78 mmol) in anhydrous acetonitrile (10 mL), and the resulting solution was stirred at room temperature for 16 hours. Formation of a new product was confirmed by TLC [stationary phase=Silica TLC, mobile phase=dichloromethane:IPA (10:1)]. The product was diluted with acetonitrile, and separated from potassium carbonate by using a filter, and evaporated to dryness under reduced pressure to obtain 1,4,7-trimethyl-1,4,7-triazonane. MS(FAB) m/z calculated value $C_9H_{21}N_3$[M]$^+$171.17, measured value 171.11

Synthesis of 1,4,7-tris(anthracen-9-ylmethyl)-1,4,7-triazonane

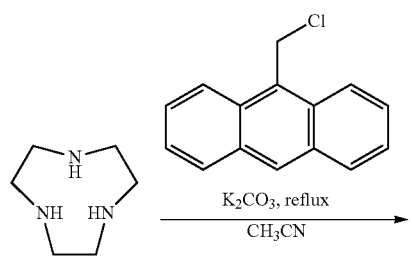

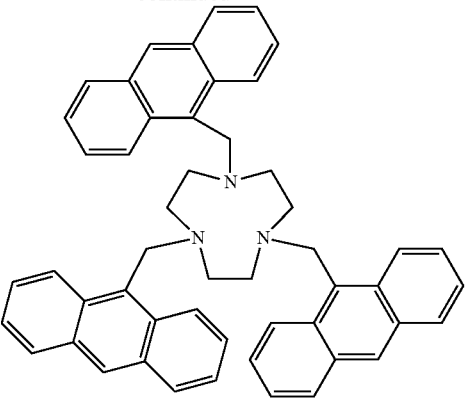

Potassium carbonate (433 mg, 3.12 mmol) and 9-(chloromethyl)anthracene (705 mg, 3.12 mmol) were added to a stirred solution of TACN (100 mg, 0.78 mmol) in anhydrous acetonitrile (10 mL), and the resulting solution was stirred at room temperature for 16 hours. Formation of a new product was confirmed by TLC [stationary phase=Silica TLC, mobile phase=dichloromethane:IPA (10:1)]. The product was diluted with acetonitrile, and separated from potassium carbonate by using a filter, and evaporated to dryness under reduced pressure to obtain 1,4,7-tris(anthracen-9-ylmethyl)-1,4,7-triazonane. HR-MS(EI) m/z calculated value $C_{51}H_{45}N_3$[M+H]$^+$ 699.3613, measured value 699.3612.

Synthesis of 1,4,7-trihexadecyl-1,4,7-triazonane

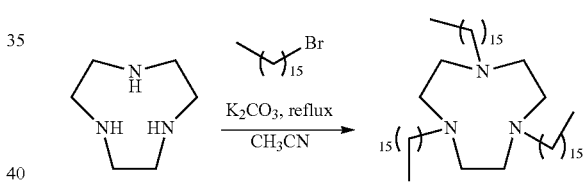

Potassium carbonate (433 mg, 3.12 mmol) and 1-bromohexadecane (949 mg, 3.12 mmol) were added to a stirred solution of TACN (100 mg, 0.78 mmol) in anhydrous acetonitrile (10 mL), and the resulting solution was stirred for 16 hours. Formation of a new product was confirmed by TLC [stationary phase=Silica TLC, mobile phase=dichloromethane:IPA (10:1)]. The product was diluted with acetonitrile, and separated from potassium carbonate by using a filter, and evaporated to dryness under reduced pressure to obtain 1,4,7-trihexadecyl-1,4,7-triazonane. HR-MS(EI) m/z calculated value $C_{54}H_{111}N_3$ [M+H]$^+$ 802.8856, measured value 802.8856.

Radioactive Labeling of Various Chelates with $^{64}$Cu $^{64}$CuCl$_2$ of 0.01 N HCl (1-2 L, 1-5 mCi) was added to various chelates (100 μg) dissolved in 100 μL of 0.1 M ammonium acetate (pH=6.8) without addition of carriers, and allowed to react for 20 minutes at 60° C. to prepare different kinds of chelate-$^{64}$Cu complexes (of the chelates, PCB cyclam which is a complex compound of the following Example 19 was reacted for 60 minutes at 90° C.). A chelate storage solution (20 μg/μL) was prepared by using MilliQ water (the following Example 19) or anhydrous DMSO (Examples 24, 25, 33, 34, 17, a mixture of 18 and 18-1, 26, and 23). Corresponding $^{64}$CU complex formation was confirmed by radio-TLC. Radioactive isotope-labeled compounds for Example 17 and a mixture of Example 18 and 18-1 were purified by using a C-18 Sep Pak column (washed with 10 mL of water to remove DMSO, the compound was eluted with 200 μL of EtOH six times).

Example 1: $^{64}$Cu Complex Compound-1a

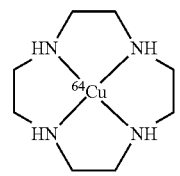

1a 0.01 mg-2 mg of 1,4,7,10-tetraazacyclododecane was dissolved in a buffer solution of 0.1 M NH$_4$OAc(pH 6.8) and then 10 μCi-10,000 μCi of $^{64}$CuCl$_2$ solution was added thereto, and allowed to react at 60° C. to prepare a $^{64}$Cu complex compound represented by Chemical Formula 1a. If the chelate was not dissolved well, a small amount of DMSO was used.

A labeling yield of the $^{64}$Cu complex compound represented by Chemical Formula 1a was confirmed by radio-TLC, and the results are shown in the following Table 1.

TABLE 1

| Reg | (mm) Start | (mm) Stop | (mm) Centroid | Rf | Region counts | Region CPM | % of Total | % of ROI |
|---|---|---|---|---|---|---|---|---|
| Rgn 1 | 48.2 | 73.1 | 62.2 | 0.271 | 167686.0 | 83843.0 | 97.67 | 100.00 |
| 1 peaks | — | — | — | — | 167686.0 | 83843.0 | 97.67 | 100.00 |

As shown in Table 1, labeling of 1,4,7,10-tetraazacyclododecane with $^{64}$Cu was found to be 100%.

Example 2: $^{64}$Cu Complex Compound-1b

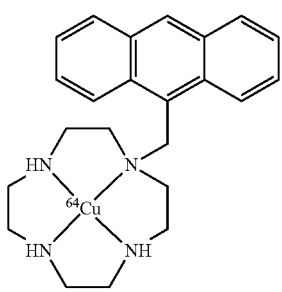

1b

A $^{64}$Cu complex compound represented by Chemical Formula 1b was obtained in the same manner as in Example 1.

Example 3: $^{64}$Cu Complex Compound-1c

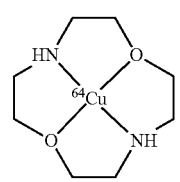

1c

A $^{64}$Cu complex compound represented by Chemical Formula 1c was obtained in the same manner as in Example 1.

Example 4: $^{64}$Cu Complex Compound-1d

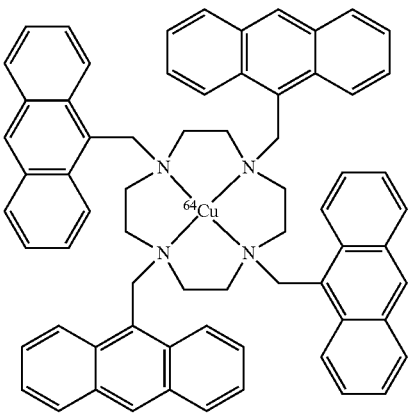

1d

A $^{64}$Cu complex compound represented by Chemical Formula 1d was obtained in the same manner as in Example 1.

Example 5: $^{64}$Cu Complex Compound-1e

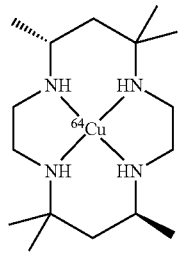

1e

A $^{64}$Cu complex compound represented by Chemical Formula 1e was obtained in the same manner as in Example 1.

Example 6: $^{64}$Cu Complex Compound-1f

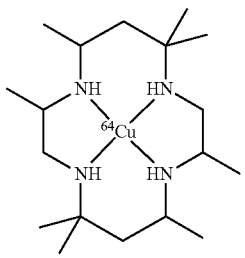

1f

A $^{64}$Gu complex compound represented by Chemical Formula 1f was obtained in the same manner as in Example 1.

Example 7: $^{64}$Cu Complex Compound-1g

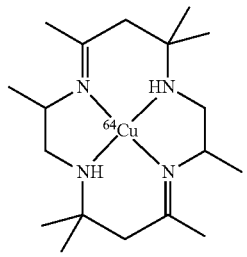

1g

A $^{64}$Gu complex compound represented by Chemical Formula 1g was obtained in the same manner as in Example 1.

Example 8: $^{64}$Cu Complex Compound-1h

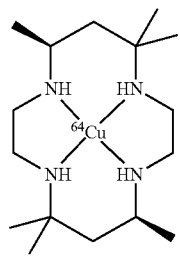

1h

A $^{64}$Cu complex compound represented by Chemical Formula 1h was obtained in the same manner as in Example 1.

Example 9: $^{64}$Cu Complex Compound-1i

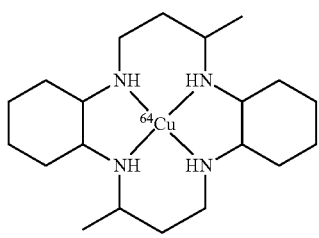

1i

A $^{64}$Cu complex compound represented by Chemical Formula 1i was obtained in the same manner as in Example 1.

Example 10: $^{64}$Cu Complex Compound-1j

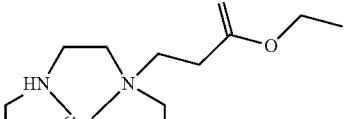

1j

A $^{64}$Cu complex compound represented by Chemical Formula 1j was obtained in the same manner as in Example 1.

Example 11: $^{64}$Cu Complex Compound-1 k

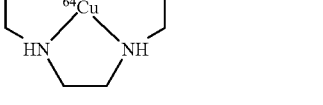

1k

A $^{64}$Cu complex compound represented by Chemical Formula 1k was obtained in the same manner as in Example 1.

Example 12: $^{64}$Cu Complex Compound-1 l

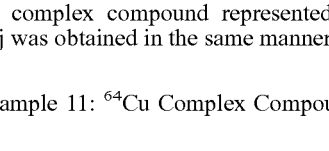

1l

A $^{64}$Cu complex compound represented by Chemical Formula 1l was obtained in the same manner as in Example 1.

Example 13: $^{64}$Cu Complex Compound-1m

1m

A $^{64}$Gu complex compound represented by Chemical Formula 1m was obtained in the same manner as in Example 1.

Example 14: $^{64}$Cu Complex Compound-1n

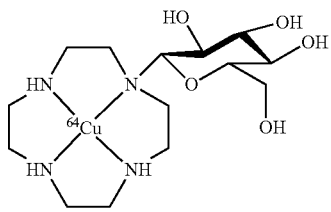

1n

A $^{64}$Cu complex compound represented by Chemical Formula 1n was obtained in the same manner as in Example 1.

Example 15: $^{64}$Cu Complex Compound-1o

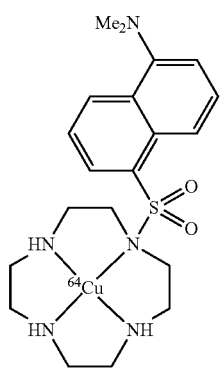

1o

A $^{64}$Cu complex compound represented by Chemical Formula 1o was obtained in the same manner as in Example 1.

Example 16: $^{64}$Cu Complex Compound-1p

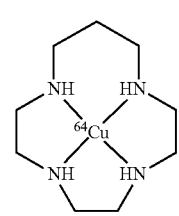

1p

A $^{64}$Cu complex compound represented by Chemical Formula 1p was obtained in the same manner as in Example 1.

Example 17: $^{64}$Cu Complex Compound-1q

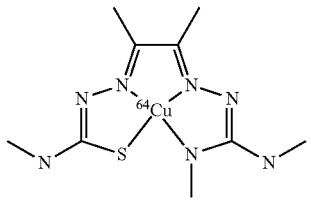

1q

A $^{64}$Gu complex compound represented by Chemical Formula 1q was obtained in the same manner as in Example 1.

Example 18: $^{64}$Cu Complex Compound-1r

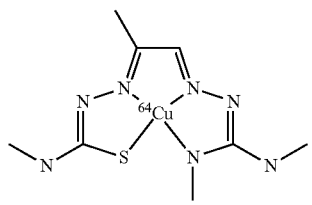

1r

A $^{64}$Cu complex compound represented by Chemical Formula 1 r was obtained in the same manner as in Example 1.

Example 18-1: $^{64}$Cu Complex Compound-1r'

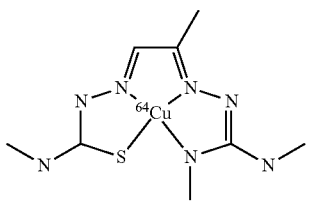

1r'

A $^{64}$Cu complex compound represented by Chemical Formula 1r' was obtained in the same manner as in Example 1.

Example 19: $^{64}$Cu Complex Compound-1s

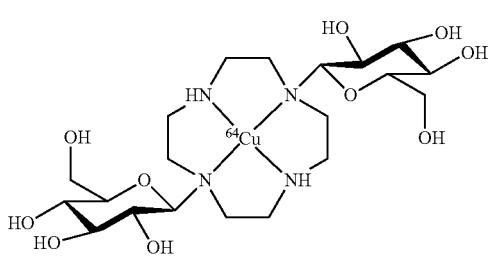

1s

A $^{64}$Gu complex compound represented by Chemical Formula 1s was obtained in the same manner as in Example 1.

Example 20: $^{64}$Cu Complex Compound-2a

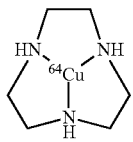

2a

A $^{64}$Cu complex compound represented by Chemical Formula 2a was obtained in the same manner as in Example 1.

Example 21: $^{64}$Cu Complex Compound-2b

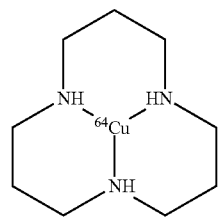

2b

A $^{64}$Gu complex compound represented by Chemical Formula 2b was obtained in the same manner as in Example 1.

Example 22: $^{64}$Cu Complex Compound-2c

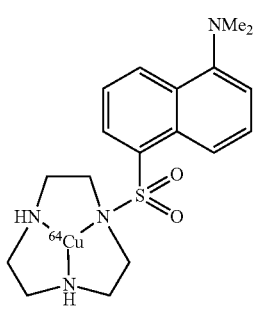

2c

A $^{64}$Gu complex compound represented by Chemical Formula 2c was obtained in the same manner as in Example 1.

Example 23: $^{64}$Cu Complex Compound-1t

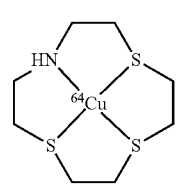

1t

A $^{64}$Gu complex compound represented by Chemical Formula 1t was obtained in the same manner as in Example 1.

Example 24: $^{64}$Cu Complex Compound-1u

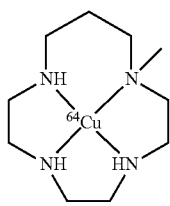

1u

A $^{64}$Gu complex compound represented by Chemical Formula 1u was obtained in the same manner as in Example 1.

Example 25: $^{64}$Cu Complex Compound-4

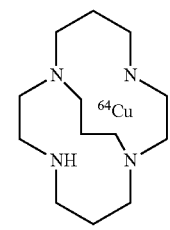

4

A $^{64}$Gu complex compound represented by Chemical Formula 4 was obtained in the same manner as in Example 1.

Example 26: $^{64}$Cu Complex Compound-1w

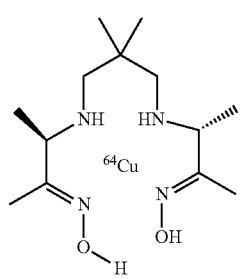

1w

A $^{64}$Gu complex compound represented by Chemical Formula 1w was obtained in the same manner as in Example 1.

Example 27: $^{64}$Cu Complex Compound-2d

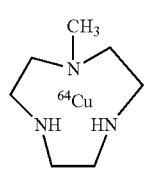

2d

A $^{64}$Gu complex compound represented by Chemical Formula 2d was obtained in the same manner as in Example 1.

Example 28: $^{64}$Cu Complex Compound-2e

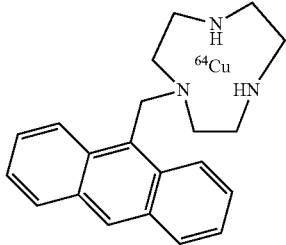

2e

A $^{64}$Gu complex compound represented by Chemical Formula 2e was obtained in the same manner as in Example 1.

Example 29: $^{64}$Cu Complex Compound-2f

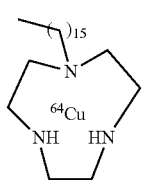

2f

A $^{64}$Cu complex compound represented by Chemical Formula 2f was obtained in the same manner as in Example 1.

Example 30: $^{64}$Cu Complex Compound-2q

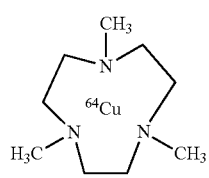

2g

A $^{64}$Cu complex compound represented by Chemical Formula 2g was obtained in the same manner as in Example 1.

Example 31: $^{64}$Cu Complex Compound-2h

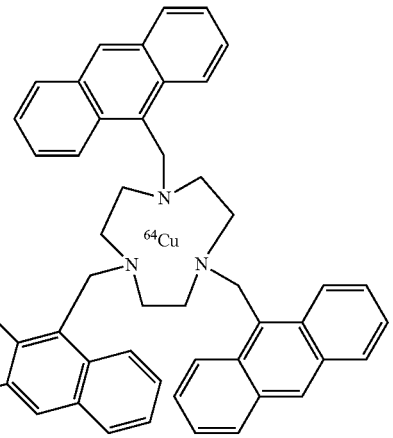

2h

A $^{64}$Gu complex compound represented by Chemical Formula 2h was obtained in the same manner as in Example 1.

Example 32: $^{64}$Cu Complex-2i

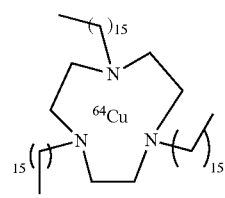

2i

A $^{64}$Gu complex compound represented by Chemical Formula 2i was obtained in the same manner as in Example 1.

Example 33: $^{64}$Cu Complex Compound-3a

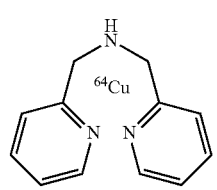

3a

A $^{64}$Cu complex compound represented by Chemical Formula 3a was obtained in the same manner as in Example 1.

Example 34: $^{64}$Cu Complex Compound-3b

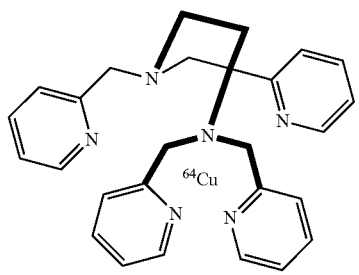

A $^{64}$Cu complex compound represented by Chemical Formula 3b was obtained in the same manner as in Example 1.

Experimental Example 1: Test of Hydrogen Sulfide Detection Sensitivity

To measure hydrogen sulfide detection sensitivity of the $^{64}$Cu-labeled complex compound according to the present disclosure, the following experiment was performed. Results are shown in the following Tables 2 and 3, and FIG. 1.

About 45 μCi-55 μCi of $^{64}$Cu-labeled complex compound (250 μL of triple distilled water) was mixed with various concentrations of NaHS solution (250 L of triple distilled water), and stirred at 37° C. for 15 minutes (a total volume used in the reaction was equally 500 μL). After completion of the reaction, the resulting products were strongly stirred to mix appropriately.

Formation of copper sulfide ($^{64}$CuS) was confirmed by quantification of % decomplexation by using a radio-TLC scanner, and results are shown in the following Tables 2 and 3.

TABLE 2

| NaHS (μM) | Example 1 cyclen | Example 2 cyclen-Anthracene (1:1) | Example 3 DODACD | Example 23 ATTCD | Example 16 cyclam | Example 20 TACN | Example 21 TACD |
|---|---|---|---|---|---|---|---|
| 0 | 0 | 0 | 0 | 0 | 0 | 0 | 0 |
| 1 | 3 | 0 | 0 | 0 | 0 | 0 | 0 |
| 10 | 11 | 0 | 3 | 0 | 0 | 9 | 6.2 |
| 15 | 63 | 0 | 6 | 36.4 | 0 | 11 | 10 |
| 20 | 95 | 15 | 79 | 49.4 | 0 | 13.5 | 58 |
| 50 | 100 | 56 | 100 | 67.7 | 1.3 | 24.6 | 63 |
| 100 | 100 | 100 | 100 | 78.2 | 10.5 | 54.4 | 100 |

TABLE 3

| Example | % decomplexation against 100 μM NaHS solution |
|---|---|
| 24 | 0 |
| 25 | 0 |
| 33 | 26.6 |
| 34 | 0 |
| 17 | 39.67 |
| 26 | 62.43 ± 0.87 |
| 23 | 78.3 ± 2.6 |

As shown in Tables 2 and 3, the results of measuring the lowest detectable concentration of hydrogen sulfide by the $^{64}$Cu-labeled complex compound according to the present disclosure showed that $^{64}$Cu-labeled cyclen of Example 1 according to the present disclosure has the lowest detection limits from low concentrations to high concentrations, and it has the most excellent sensitivity for hydrogen sulfide.

Figure 2B:
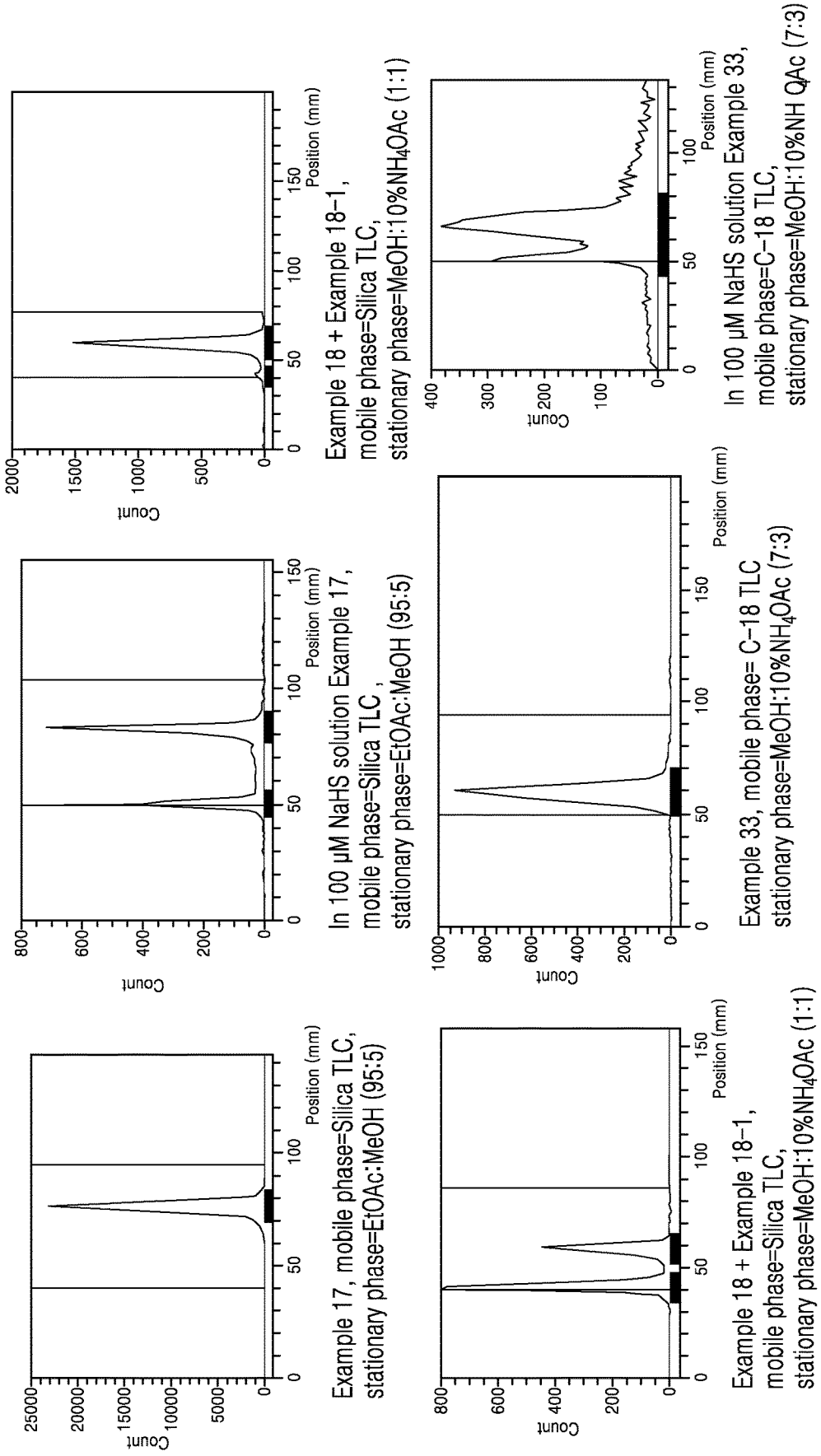

As shown in FIGS. 2A and 2B, radio-TLC results of using $^{64}$Cu-labeled cyclen of Example 1 according to the present disclosure at different concentrations of sulfide ion showed that $^{64}$Cu-labeled cyclen of Example 1 had Rf value greater than 0, but when $^{64}$Cu-labeled cyclen of Example 1 reacts with sulfide ions to form $^{64}$CuS, its Rf value was changed to 0, and it remained at a starting point without moving, and therefore, reaction was easily detected.

Experimental Example 2: Test of Hydrogen Sulfide Detection Over Time

Figure 3:
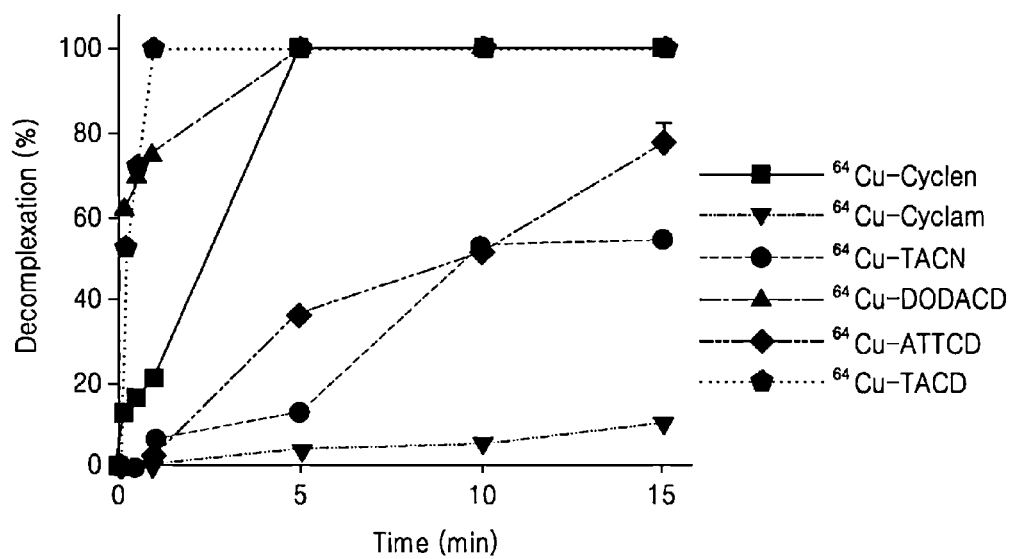
FIG. 3 shows a graph measuring hydrogen sulfide reactivity of $^{64}$Cu-labeled complex compounds according to the present disclosure over time.

To examine reactivity of the $^{64}$Cu-labeled complex compound according to the present disclosure over time, the following experiment was performed. Results are shown in the following Table 4 and FIG. 3.

A detailed experimental method is as follows.

About 45 μCi-50 μCi of $^{64}$Cu-labeled complex compound (250 μL of triple distilled water) was mixed with 100 μM of NaHS solution (250 mL of triple distilled water), and stirred at 37° C. for 15 minutes. Formation of copper sulfide ($^{64}$CuS) was quantified by using a radio-TLC scanner.

TABLE 4

| Section | | 10 sec | 30 sec | 60 sec | 5 min | 10 min | 15 min |
|---|---|---|---|---|---|---|---|
| Example 1 | cyclen | 13 | 17 | 21 | 100 | 100 | 100 |
| Example 2 | cyclen-Anthracene | 21 | 22 | 33 | 82 | 100 | 100 |
| Example 3 | DODACD | 62 | 70 | 75 | 100 | 100 | 100 |
| Example 16 | cyclam | 0 | 0 | 0 | 3 | 5 | 10 |
| Example 20 | TACN | 0 | 0 | 5 | 13 | 60 | 60 |
| Example 21 | TACD | 52 | 72 | 100 | 100 | 100 | 100 |

As shown in Table 4, to examine a reaction rate of the $^{64}$Cu-labeled complex compound according to the present disclosure with sulfide ions, hydrogen sulfide concentrations were measured over time. As a result, $^{64}$Cu-labeled complex compounds of Examples 1, 2, 3 and 21 were found to begin to detect hydrogen sulfide within about 10 seconds.

Experimental Example 3: Test of Hydrogen Sulfide Selectivity

In addition to hydrogen sulfide, many different anions, radicals, etc. exist in the body. Therefore, to examine selective reactivity of the $^{64}$Cu-labeled complex compound according to the present disclosure for sulfide ions, the following experiment was performed. Results are shown in the following Table 5.

About 45 μCi-55 μCi of the $^{64}$Cu-labeled complex compound (250 μL of triple distilled water) was mixed with 100 μM of various anion solutions (250 μL of triple distilled water) including biothiol, and stirred at 37° C. for 15 minutes.

Formation of copper sulfide ($^{64}$CuS) was quantified by using a radio-TLC scanner.

Various biothiol or salt solutions were prepared by dissolving the compounds in triple distilled water.

A colon carcinoma cell CT-26 was seeded in each plate at a density of $5\times10^6$, and then 10 μCi-300 μCi of $^{64}$Cu-labeled complex compound of Examples 1, 7 or 9 according to the present disclosure was treated thereto, followed by incubation for 10 minutes. The cells were washed with PBS, and then 0 μM, 1 μM, or 50 μM of NaHS solution was added thereto, followed by incubation for 5 minutes. Thereafter, the cells were washed with PBS, and then cells were removed from the plate by adding trypsin and EDTA, followed by centrifugation. Supernatants were discarded and radiation of remaining cells was measured by using a gamma counter.

TABLE 5

| | Decomplexation [%] | | | | | |
|---|---|---|---|---|---|---|
| | Example 20 $^{64}$Cu-TACN | Example 1 $^{64}$Cu-cyclan | Example 16 $^{64}$Cu-cyclam | Example 3 $^{64}$Cu-DODACD* | Example 23 $^{64}$Cu-ATTCD | Example 21 $^{64}$Cu-TACD* |
| Cys | 0.8 ± 0.3 | 0.5 ± 0.1 | 0.7 ± 0.2 | 0.4 | 0.5 | 9 ± 3 |
| Hcys | 1.1 ± 0.5 | 1.4 ± 0.4 | 0.7 ± 0.0 | 27 ± 3 | 0.4 | 30 ± 5 |
| GSH | 2.6 ± 0.0 | 0.7 ± 0.0 | 0.8 ± 0.2 | 48 | 0.7 | 33 |
| DTT | 0.9 ± 0.1 | 0.6 ± 0.4 | 0.8 ± 0.0 | 45 ± 2 | 0.4 | 25 |
| L-AsA | 0.8 ± 0.5 | 0.5 ± 0.1 | 0.7 ± 0.2 | 15 | 0.4 | 4 ± 2 |
| ME | 0.4 ± 0.0 | 0.5 ± 0.1 | 0.5 ± 0.6 | 16 | 0.5 | 2 ± 2 |
| NaCl | 0.5 ± 0.0 | 0.2 ± 0.0 | 0.7 ± 0.0 | 0.3 | 0.5 | 0.4 ± 0.2 |
| KI | 0.4 ± 0.2 | 0.7 ± 0.2 | 0.7 ± 0.0 | 0.1 | 0.2 | 0.3 |
| Na$_2$S$_2$O$_3$ | 0.5 ± 0.0 | 0.4 ± 0.0 | 0.8 ± 0.1 | 19 ± 5 | 0.2 | 3 ± 1 |
| Na$_2$S$_2$O$_5$ | 0.5 ± 0.2 | 0.5 ± 0.2 | 0.5 ± 0.0 | 5 | 0.6 | 4 ± 2 |
| NaOAc | 0.3 ± 0.0 | 0.6 ± 0.1 | 0.8 ± 0.0 | 15 | 0.3 | 1 |
| H$_2$O$_2$ | 0.8 ± 0.3 | 0.5 ± 0.4 | 0.7 ± 0.2 | 0.4 | 0.3 | 3 |
| NaClO$_4$ | 0.4 ± 0.1 | 0.6 ± 0.2 | 0.6 ± 0.1 | 0.4 | 0.8 | 2 ± 1 |
| NaHCO$_3$ | 0.6 ± 0.4 | 0.6 ± 0.3 | 0.5 ± 0.1 | 0.3 | 0.1 | 0.9 |
| NaNO$_2$ | 0.4 ± 0.0 | 0.6 ± 0.0 | 0.5 ± 0.1 | 0.5 | 0.6 | 0.5 |
| NaN$_3$ | 0.4 ± 0.0 | 0.3 ± 0.2 | 0.7 ± 0.1 | 0.6 | 0.8 | 0.5 |
| ATB 337 | 0.7 ± 0.2 | 0.7 ± 0.4 | 0.6 ± 0.0 | 3 ± 1 | 0.6 | 6 ± 2 |
| DAT | 0.7 ± 0.6 | 0.4 ± 0.3 | 0.5 ± 0.1 | 100 | 0.4 | 49 ± 2 |

In Table, concentrations of all biothiols and other competitive materials are 100 μM. Further, specific concentrations of biothiols, anions, and oxidants used in Table are as follows: [L-Cys (1 mM); L-Hcys (10 mM); GSH (10 mM); DL-dithiothretitol (DTT, 100 μM); L-ascorbic acid (L-AsA, 10 mM); 2-mercaptoethanol (2-ME, 10 mM); NaCl (10 mm); KI (1 mM); Na$_2$S$_2$O$_3$ (1 mM); Na$_2$S$_2$O$_5$ (1 mM); NaOAc (1 mM); H$_2$O$_2$ (100 M); NaClO$_4$ (100 μM); NaHCO$_3$ (100 μM); NaNO$_2$ (100 M); NaN$_3$ (100 μM); ATB 337 (100 μM); diallyl trisulphide (100 μM)].

As shown in Table 5, results of measuring reactivity with various anions containing sulfur showed that $^{64}$Cu-labeled complex compounds of Examples sulfide whereas $^{64}$Cu-labeled complex compounds of Examples 3 and 21 did not selectively react with hydrogen sulfide, and they also reacted with other biothiol compounds or anions.

Further, selective reactivity of radioactive isotope copper ions, which were not labeled with chelates, with hydrogen sulfide was examined. As a result, it was found that the copper ions reacted with various biothiol compounds or anions, unlike $^{64}$Cu-labeled cyclen of Example 1 according to the present disclosure.

Experimental Example 4: Cellular Uptake Test

Cellular drug uptake is an important prognostic factor in the diagnosis of diseases. Therefore, to examine cellular uptake of the $^{64}$Cu-labeled complex compounds according to the present disclosure, experiments for measuring changes in the cellular uptake under various concentrations of hydrogen sulfide were performed.

Results are shown in the following Table 6.

TABLE 6

| Section | Concentration (μM) | Uptake |
|---|---|---|
| Example 1 | 0 | 600 |
| | 1 | 780 |
| | 50 | 850 |
| Example 7 | 0 | 20000 |
| | 1 | 21000 |
| | 50 | 23000 |
| Example 9 | 0 | 7000 |
| | 1 | 6500 |
| | 50 | 6900 |
| Example 20 | 0 | 30000 |
| | 1 | 32000 |
| | 50 | 34000 |

As shown in Table 6, $^{64}$Cu-labeled complex compounds according to the present disclosure showed that as the NaHS concentration was increased, radiation of $^{64}$Cu-labeled complex compounds by cellular uptake slightly increased.

Experimental Example 4-2: Test of Hydrogen Sulfide-Specific Imaging

In order to examine whether the $^{64}$Cu-labeled complex compounds according to the present disclosure are able to selectively detect in vivo hydrogen sulfide, different materials were injected into the backs of rats, and then each $^{64}$Cu-labeled complex compound according to the present disclosure was injected via the tail, and then selective imaging was examined by optical imaging.

Figure 4:
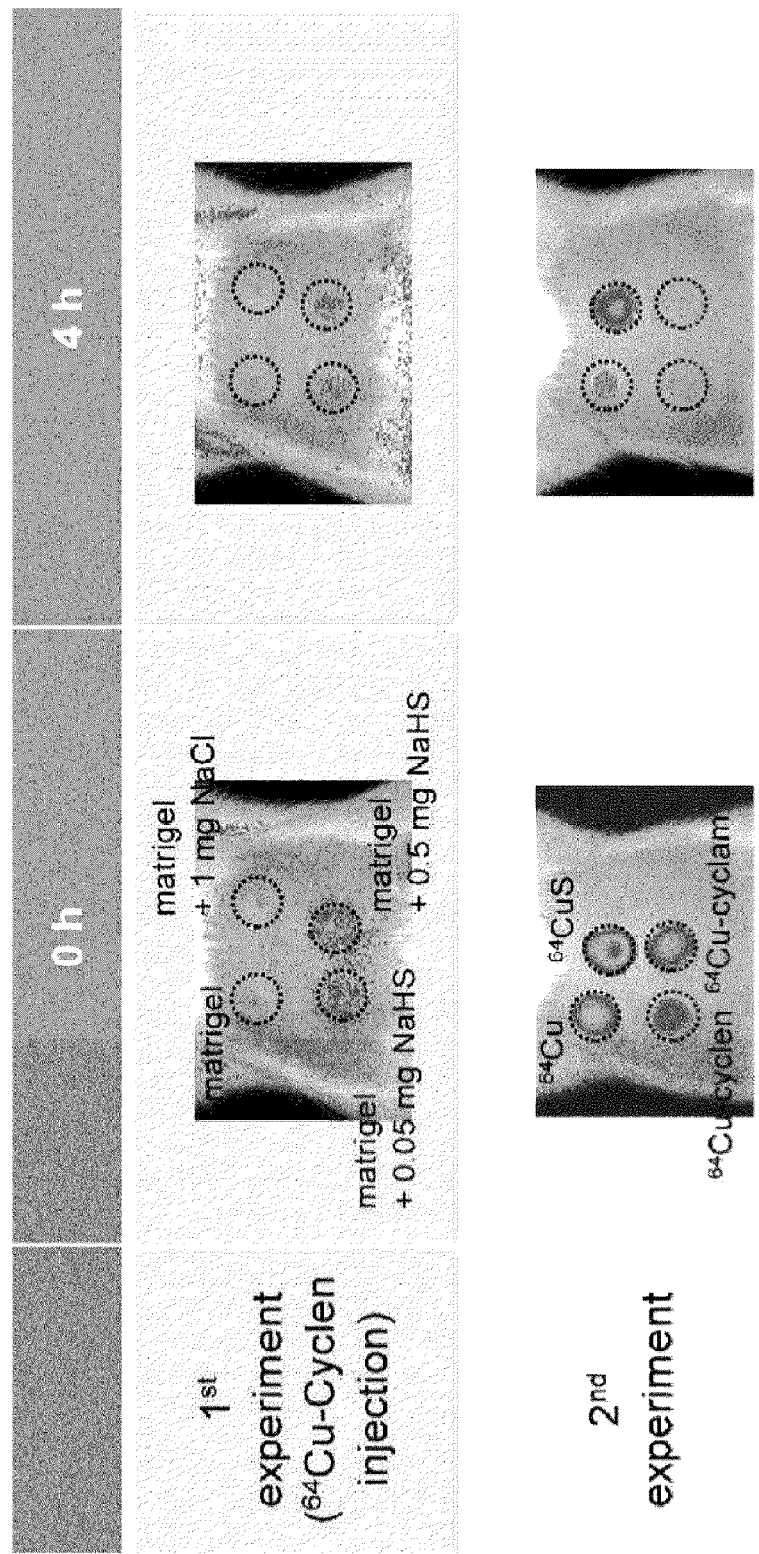
FIG. 4 shows photographs of examining selective imaging through optical imaging after injecting the backs of rats with $^{64}$Cu-labeled complex compounds according to the present disclosure.

FIG. 4 shows photographs of examining selective imaging through optical imaging after injecting the backs of rats with $^{64}$Cu-labeled complex compounds according to the present disclosure. Referring to FIG. 4, at the beginning of the first experiment, matrigel alone, matrigel+1 mg NaCl, matrigel+0.5 mg NaHS, and matrigel+0.05 mg NaHS were injected into four sites on the backs of rats, respectively. 1.8 mCi of the $^{64}$Cu-labeled complex compound according to Example 1 was injected via the tails of rats, immediately followed by optical imaging. As a result, of the four sites, signals were detected only in the lower two sites injected with NaHS generating hydrogen sulfide. Even after 4 hours, signals were still detected only in the lower two sites.

Next, at the beginning of the second experiment, about 0.48 mCi of $^{64}$Cu(II) ion, $^{64}$CuS, $^{64}$Cu-labeled complex compound according to Example 1, and $^{64}$Cu-labeled complex compound according to Example 16 were injected into four sites on the backs of the same rats, respectively. Immediately, optical images were taken and shown in a lower left image of FIG. 4. A photograph taken after 4 hours was shown in a lower right image of FIG. 4. Referring to FIG. 4, $^{64}$Cu-labeled complex compound according to Example 1 and $^{64}$Cu-labeled complex compound according to Example 16 were very rapidly excreted from the body, unlike $^{64}$CuS. A retention time of $^{64}$Cu(II) ion was about half of $^{64}$CuS. These experiments showed that the $^{64}$Cu-labeled complex compounds according to the present disclosure bind with hydrogen sulfide to form $^{64}$CuS, which remains for a long time in the body, thereby being easily detected by imaging.

Preparation Example 1: Preparation of Animal Models (1) Paw Pain Inflammation Model A small amount of CFA (complete Freund's adjuvant) or formalin was injected into only one paw (right) of the hind paws of Balb/c or ICR mice to establish inflammation models. 1 day after injection of the inflammation inducer, the mice were used in imaging or other in vivo experiments.

It is a known fact that inflamed sites show high concentrations of hydrogen sulfide.

(2) Myocardial Infarction Model

A myocardial infarction model was established by using Sprague-Dawley rats (12-week-old or older, about 250 g). 2 days later after induction of myocardial infarction by occlusion of the coronary arteries in the heart, the rats were used in imaging tests. It is a known fact that myocardial infarction sites show high concentrations of hydrogen sulfide.

(3) Arthritis Model

An arthritis inducer, bovine type II collagen was intradermally injected into the tails of DBA/1J mice twice, and 5 weeks later (about 13-week-old), the mice were used in imaging tests. Arthritis degree of the paw was quantified by scoring.

(4) Brain Inflammation Model

An inflammation inducer, lipopolysaccharide was directly injected into one part of the brain of Sprague-Dawley rat to induce inflammation in one part of the brain. 24 hours after induction of inflammation, the rats were used in imaging tests.

(5) Tumor Model

To prepare a CT26 tumor model, the number of cells was counted using a haemacytometer, and 5×10$^6$ cells were subcutaneously injected into the right flank of BALB/c mouse. About 10 days later, when formation of about 1 cm of tumor was observed, the mice were used in subsequent experiments.

To prepare an EMT6 tumor model, the number of cells was counted using a haemacytometer, and 2×10$^5$ cells were subcutaneously injected into the right flank and left shoulder region of BALB/c female mouse. About 2~3 weeks later, when formation of about 1 cm of tumor was observed, the mice were used in subsequent experiments.

(6) Sepsis Model

After the lower abdominal region of ICR mice was opened, a small puncture in the appendix was made by using a syringe needle to prepare an acute sepsis model.

(7) Brain Tumor Model

The surface of the rat's head was incised and the capillaries and meninges on the outer surface of the skull were removed. Subsequently, a hole was made at the defined coordinates by stereotactic surgery, and 20,000 C6 cells which are known as glioma cells of the rat brain were injected by using a syringe pump. After cell injection, the syringe was left for about 5 minutes to allow absorption of the cells, and then slowly removed. The hole was filled with bone cement, and then sutured to prepare a brain tumor model.

(8) Pancreatitis Model

Caerulein (50 μg/kg) was intraperitoneally injected into Balb/c mouse seven times at hourly intervals to prepare a pancreatitis model.

Experimental Example 5: Optical Imaging and Nuclear Medicine Imaging Studies

Nuclear medicine imaging was measured by using an Inveon PET/CT system of Siemens Healthcare, and optical imaging was measured by using IVIS spectrum CT equipment. Cherenkov radiation emitted from $^{64}$Cu was measured by using a highly sensitive CCD (charge-coupled device) camera.

Imaging was measured for 1 minute to 5 minutes, and a radiation dose was about 50 μCi to 2000 μCi, and photographs were variously taken as needed, such as immediately after first injection, at 1 hour, 4 hours, and 24 hours later.

(1) Paw Inflammation Model

Figure 5A:
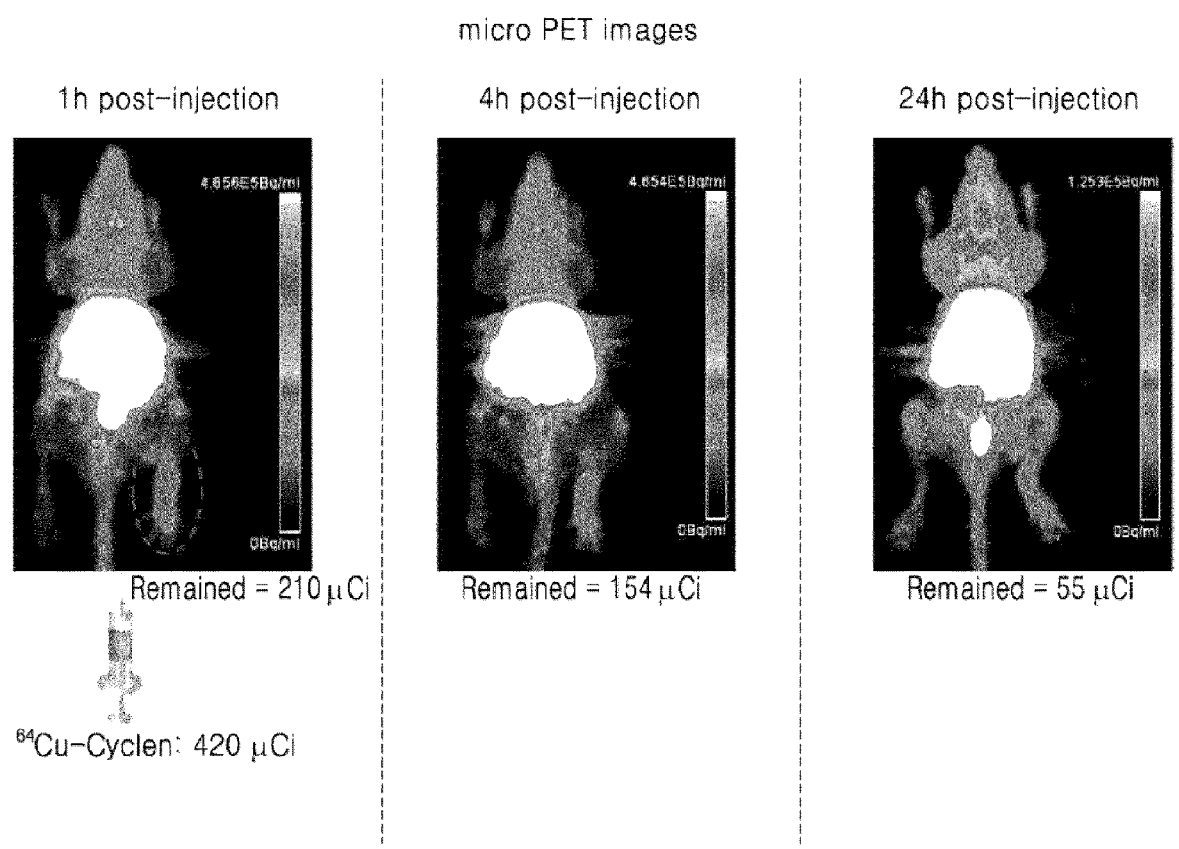
FIGS. 5A to 5D show results of imaging paw inflammation models injected with a $^{64}$Cu-labeled complex compound of Example 1 according to a specific embodiment of the present disclosure.
Figure 5B:
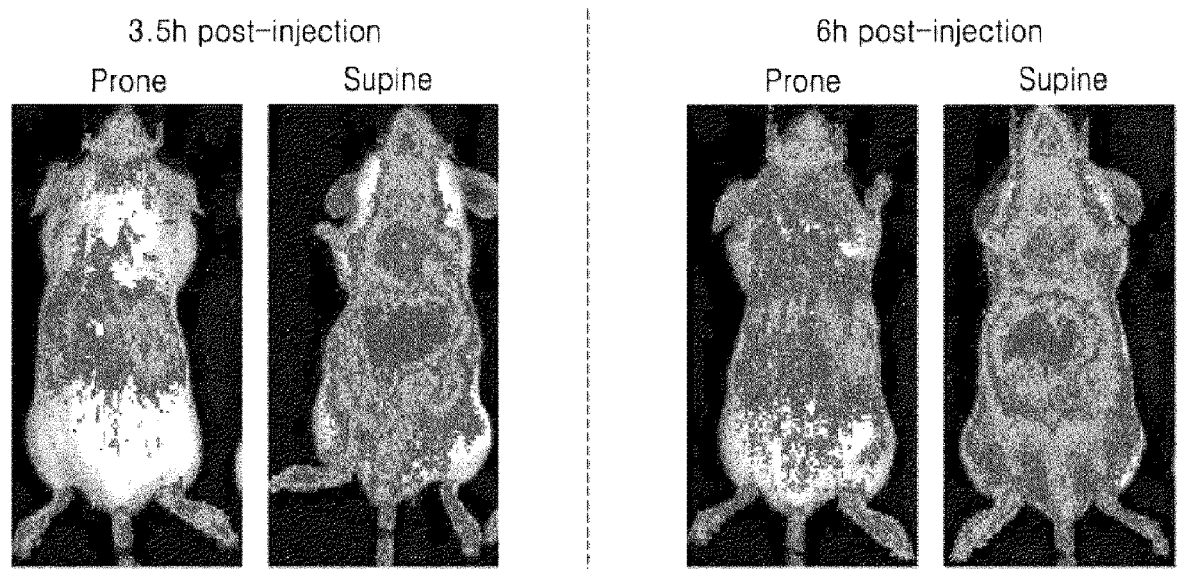
Figure 5C:
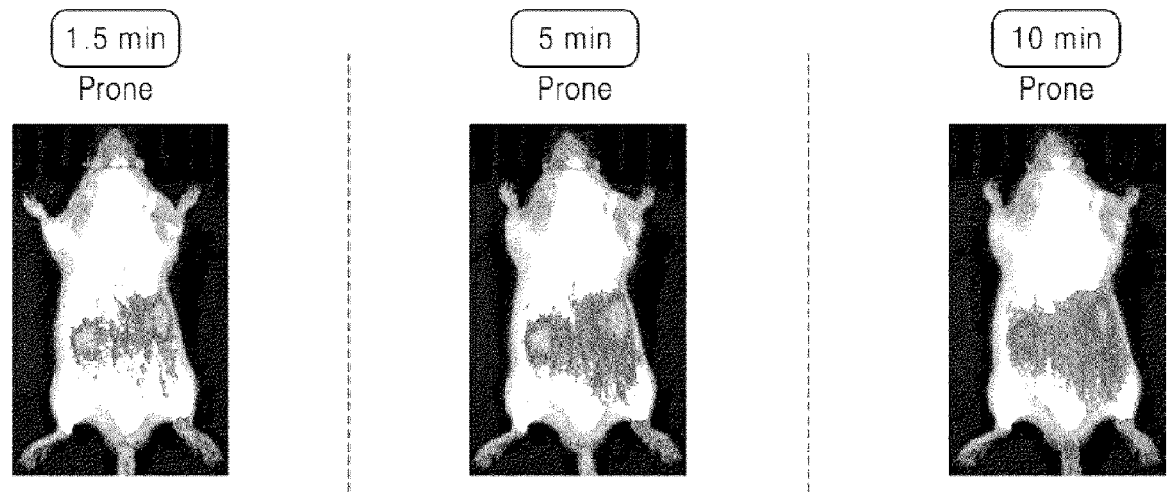

As shown in FIG. 5A, result of treating $^{64}$Cu-labeled cyclen of Example 1 according to the present disclosure showed that higher uptake in the inflamed right paw than in the opposite paw was observed in PET imaging. As shown in FIG. 5B, optical imaging showed increased uptake of $^{64}$Cu-labeled cyclen of Example 1 according to the present disclosure in the CFA-induced inflamed site. As shown in FIG. 5C, it was confirmed that $^{64}$Cu-labeled cyclen of Example 1 according to the present disclosure showed a high reaction rate with hydrogen sulfide such that the inflamed site can be detected immediately after injection (1.5-10 minutes).

Figure 5D:
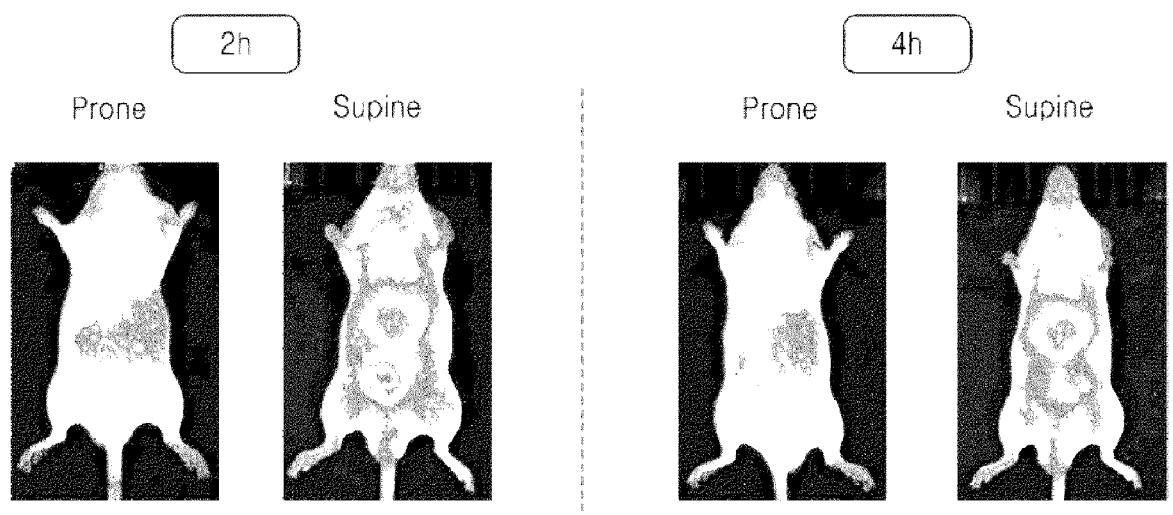

As shown in FIG. 5D, the same results were also observed in the paw inflammation ICR and Balb/c mouse models, and $^{64}$Cu-labeled cyclen of Example 1 according to the present disclosure showed a retention time of 24 hours or longer in the animal models, suggesting that therapeutic effects may be predicted in a non-invasive manner without continuous injection of the drug.

Figure 6A:
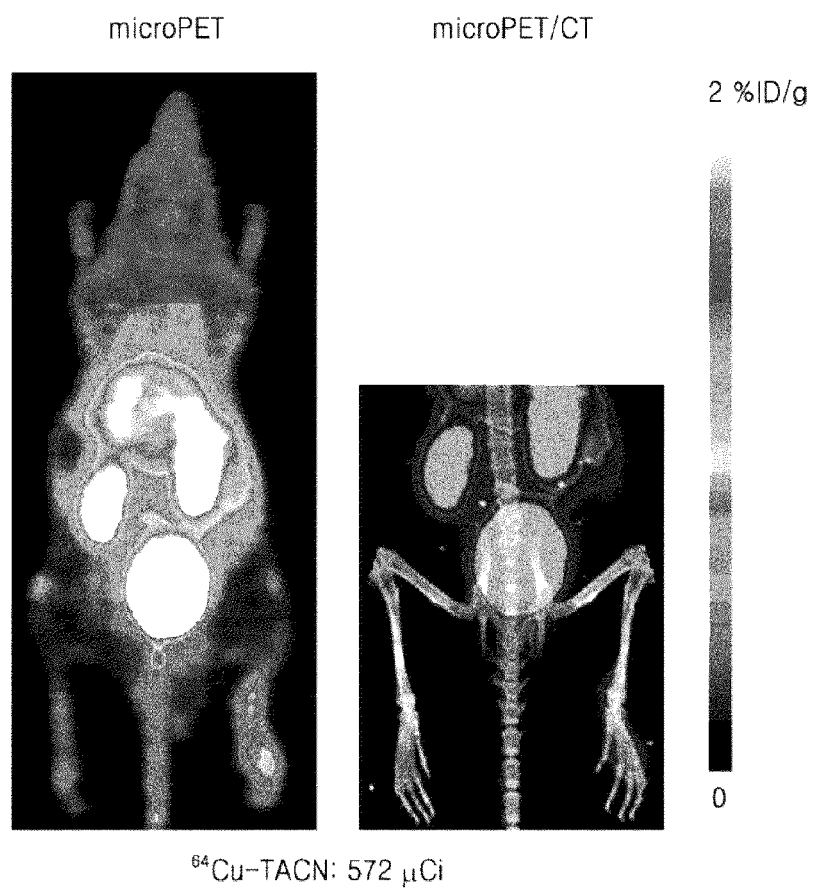
FIGS. 6A to 6C show results of imaging paw inflammation models injected with a $^{64}$Cu-labeled complex compound of Example 20 according to a specific embodiment of the present disclosure.
Figure 6B:
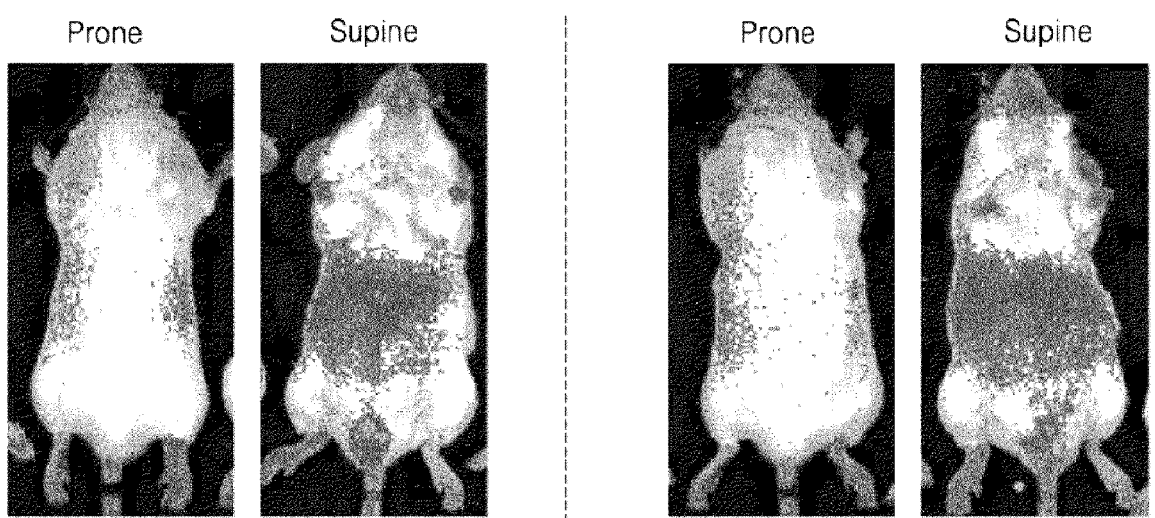
Figure 6C:
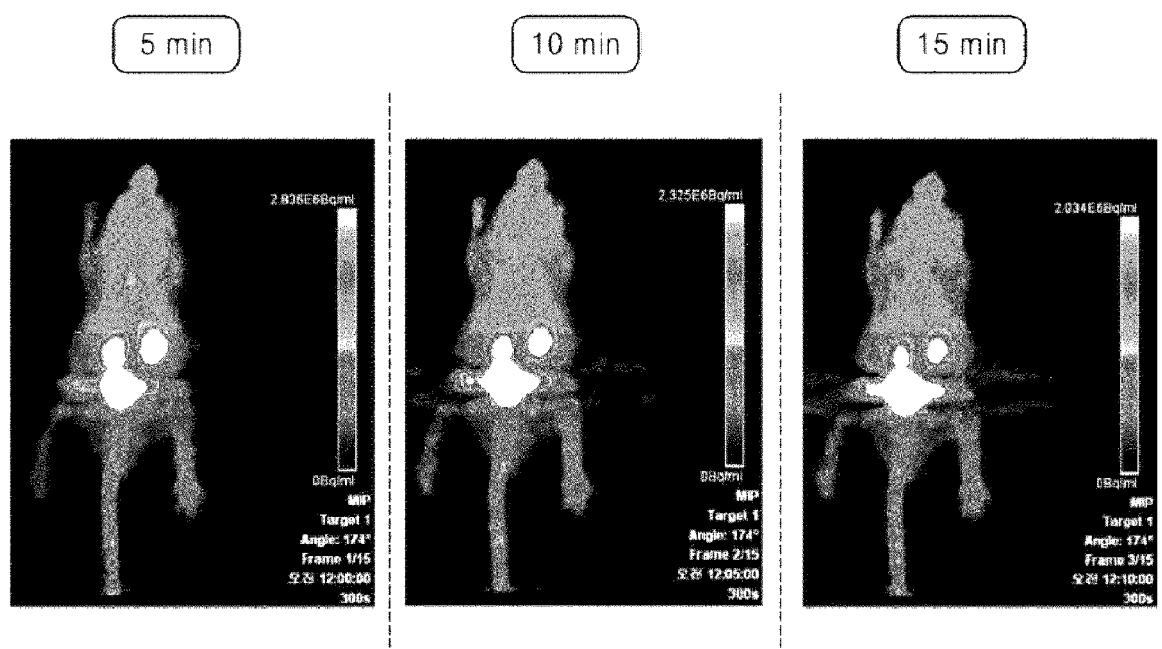
Figure 7B:
Figure 7C:
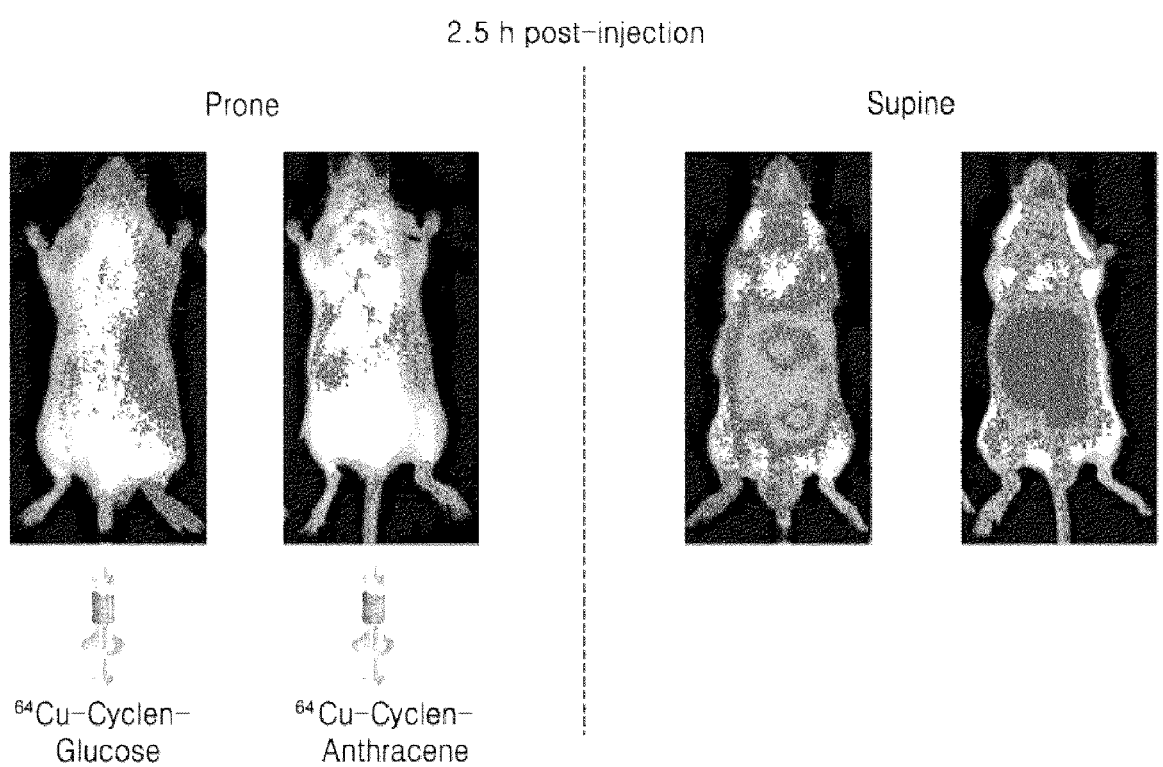
Figure 7D:
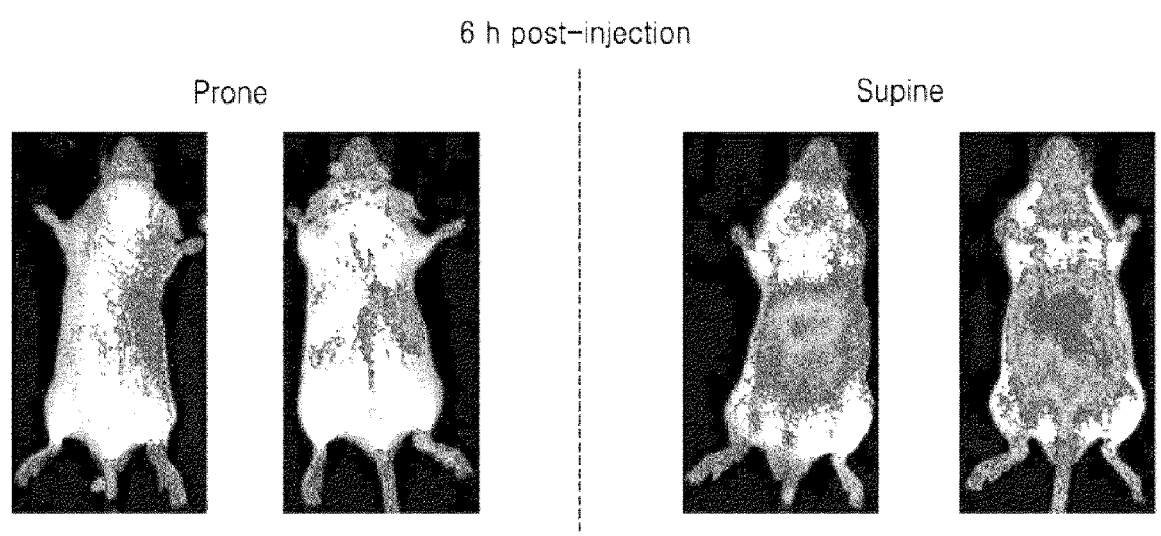
Figure 8A:
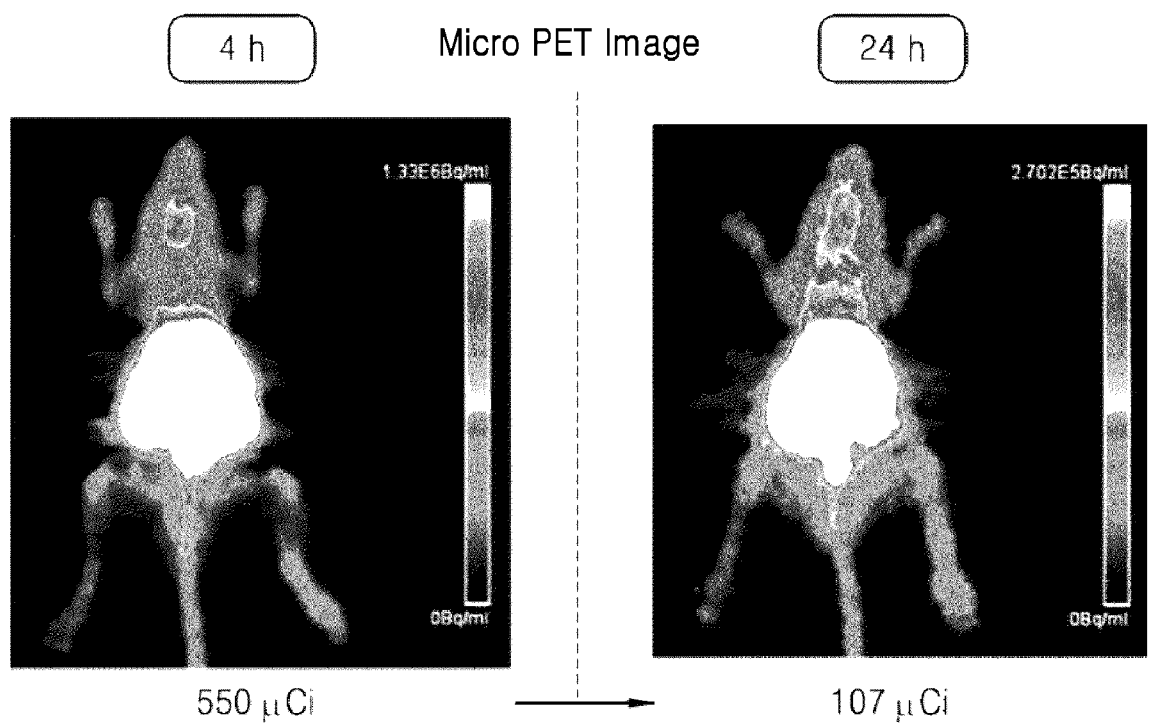
Figure 8B:
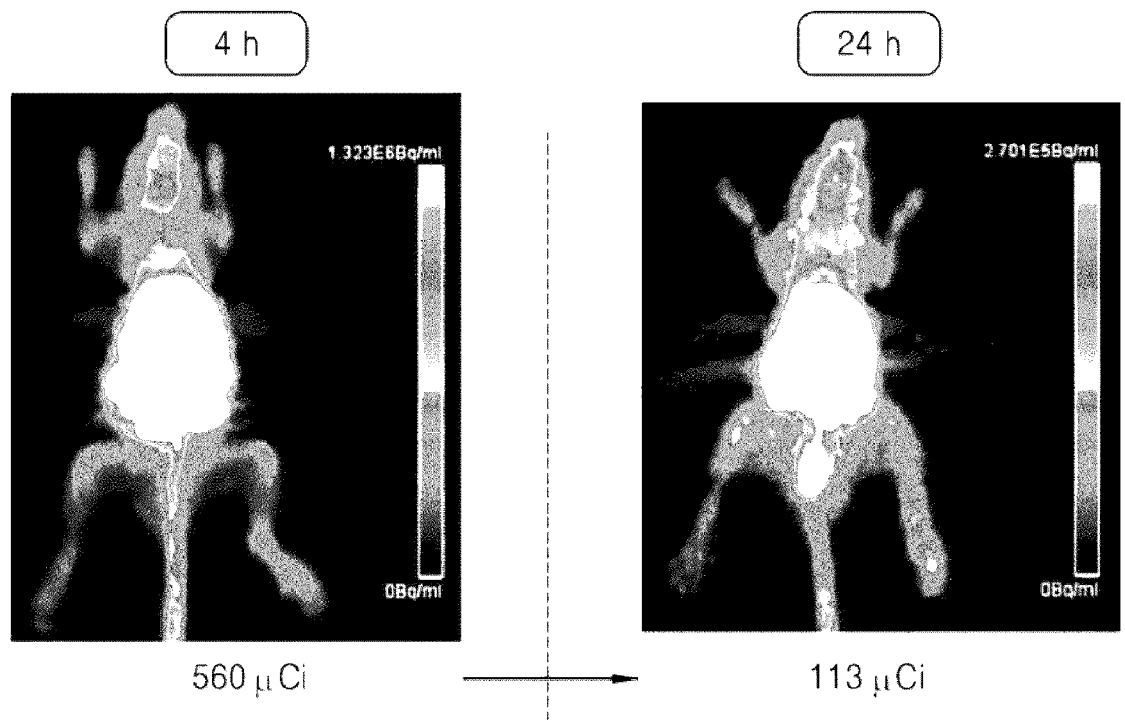
Figure 8D:
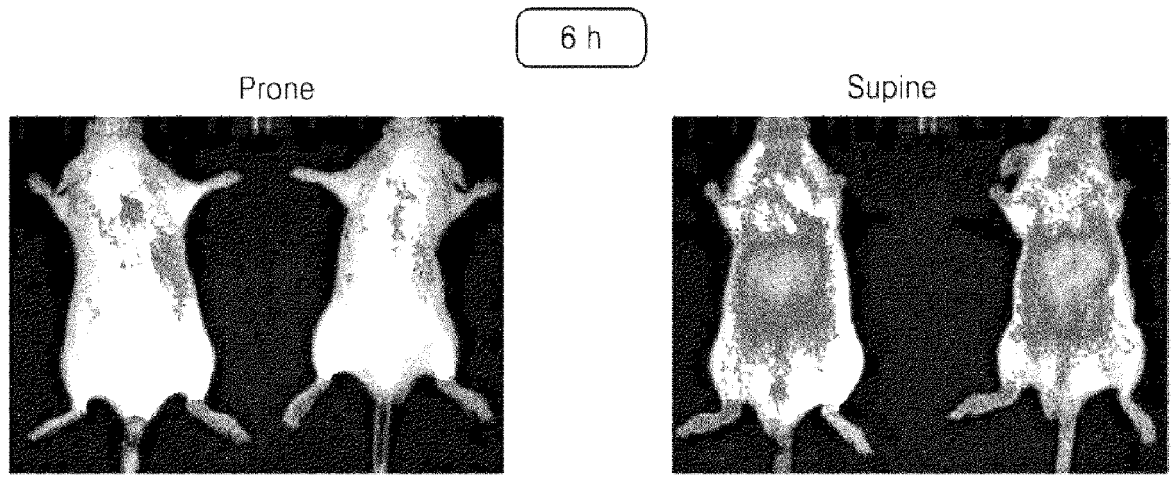
Figure 8E:
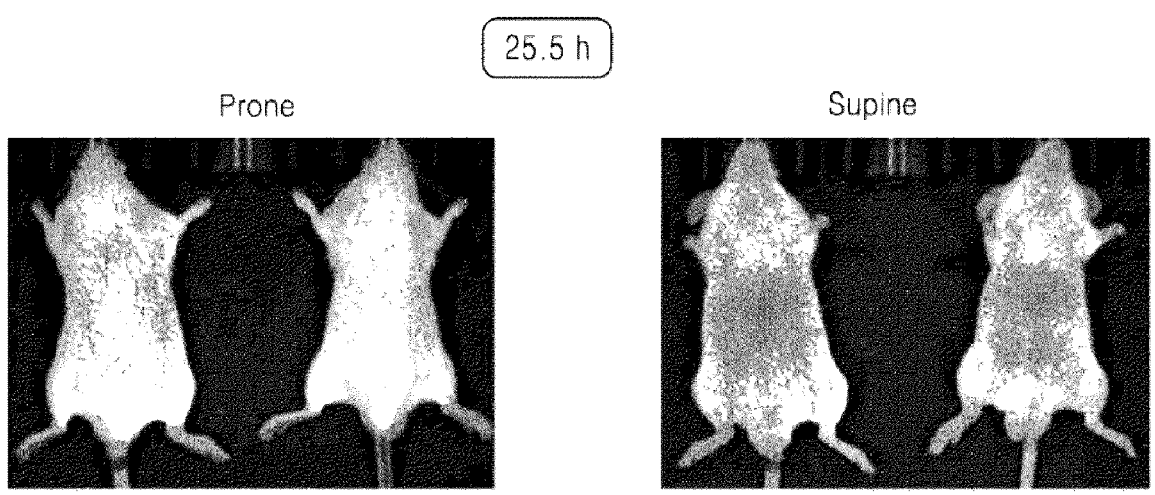
Figure 9A:
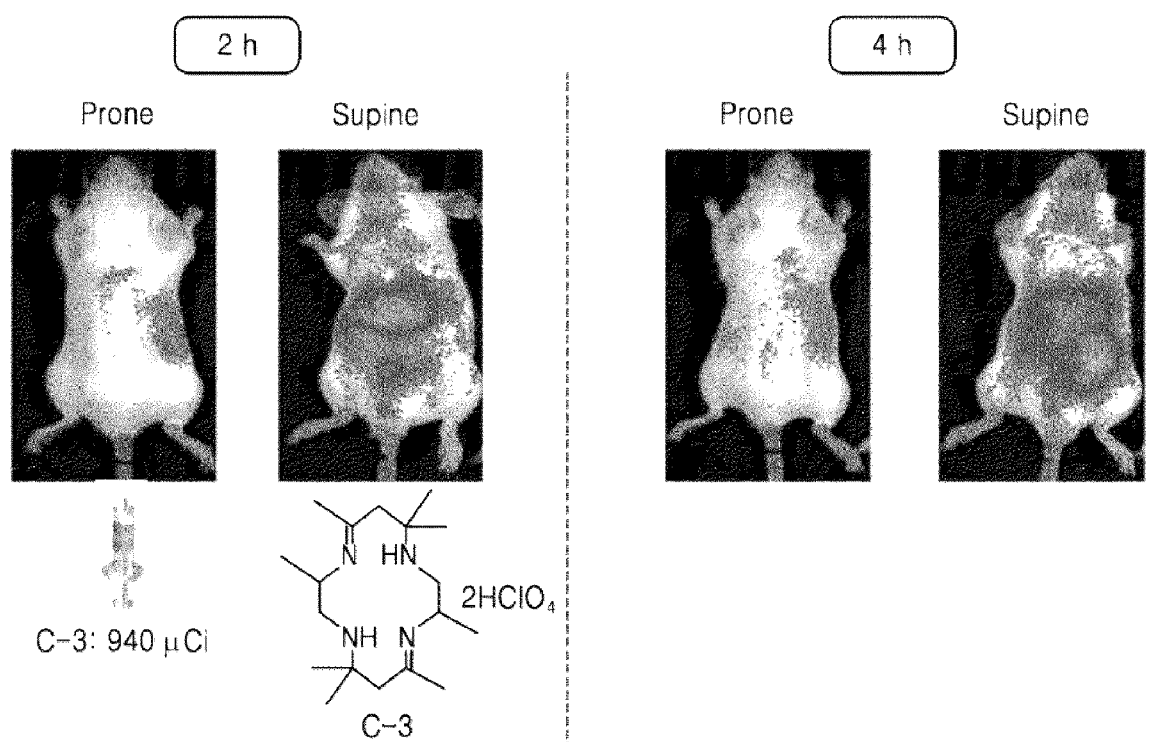
FIGS. 9A and 9B show results of imaging paw inflammation models injected with a $^{64}$Cu-labeled complex compound of Example 7 according to a specific embodiment of the present disclosure.
Figure 9B:
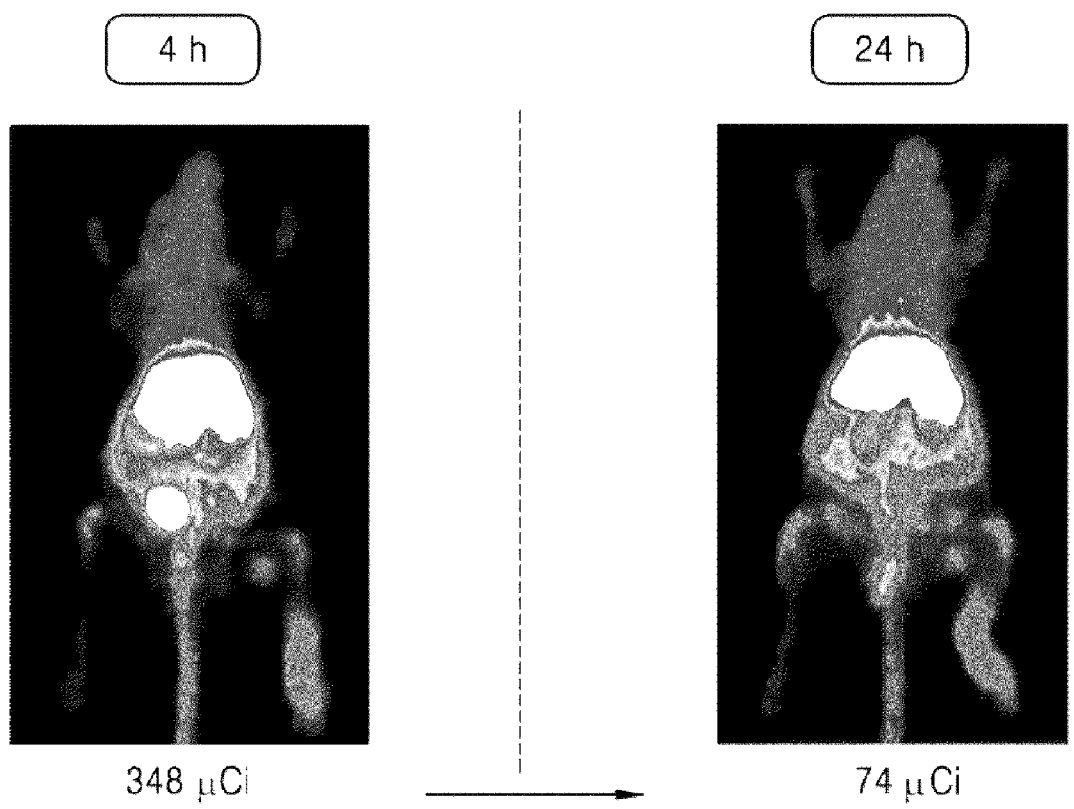
Figure 10A:
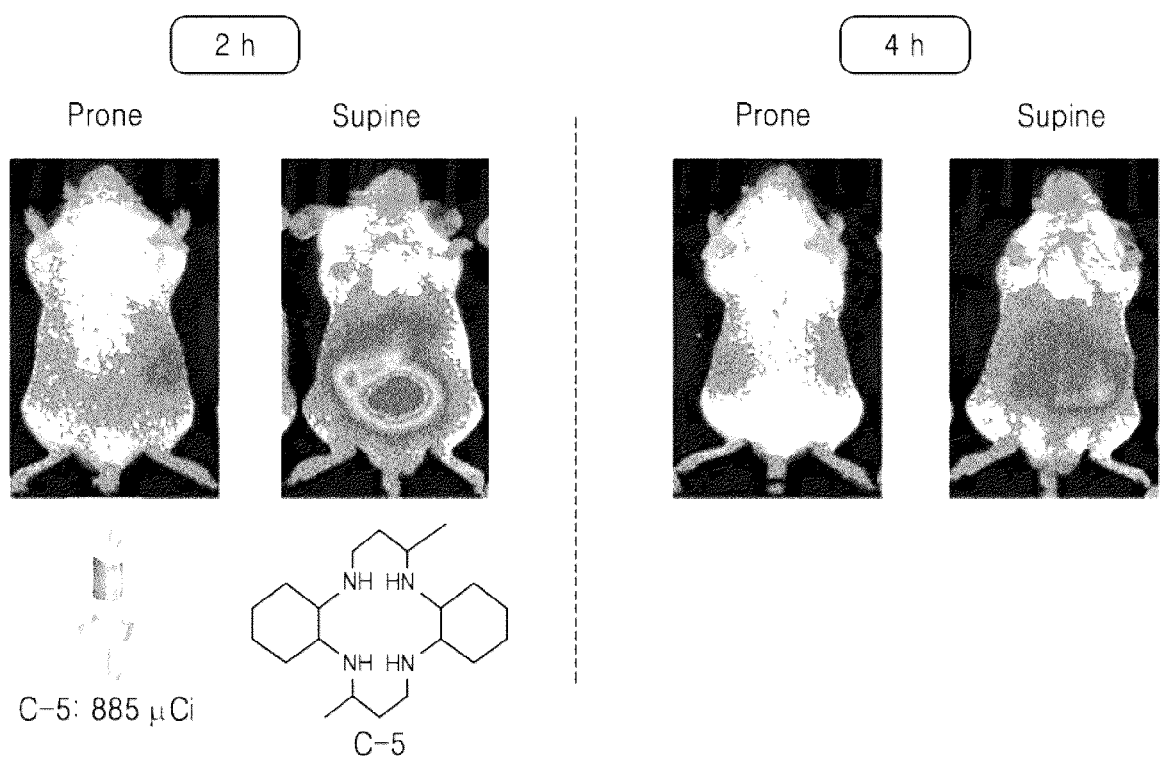
FIGS. 10A and 10B show results of imaging paw inflammation models injected with a $^{64}$Cu-labeled complex compound of Example 9 according to a specific embodiment of the present disclosure.
Figure 10B:
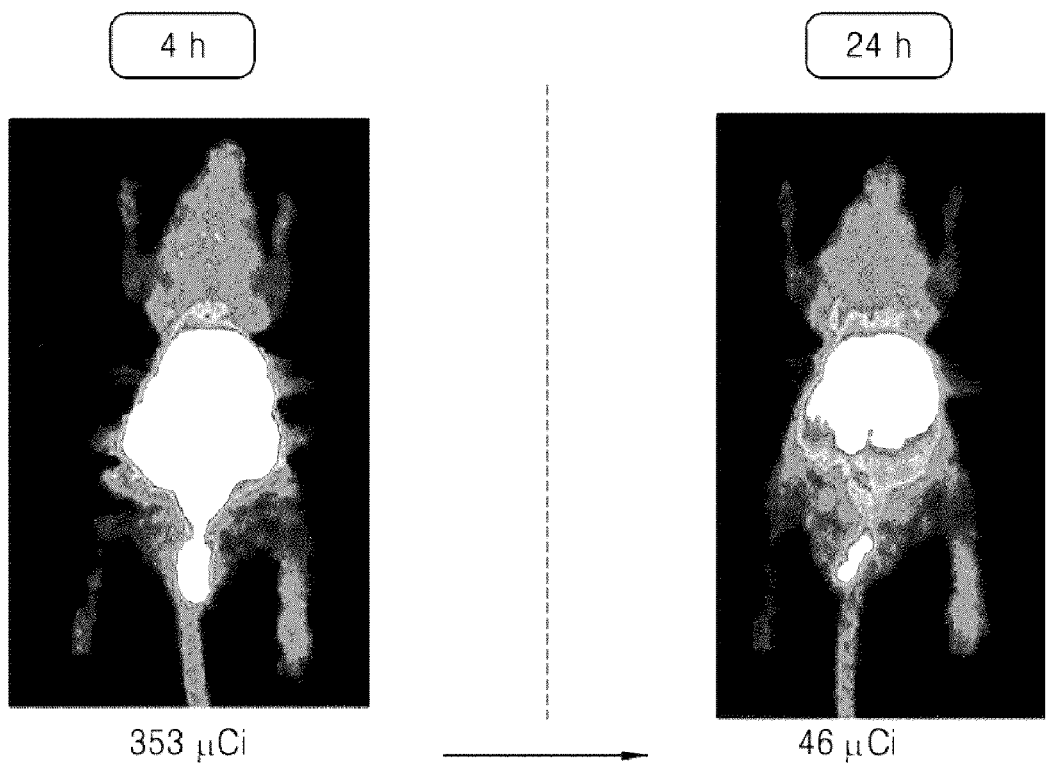
Figure 11A:
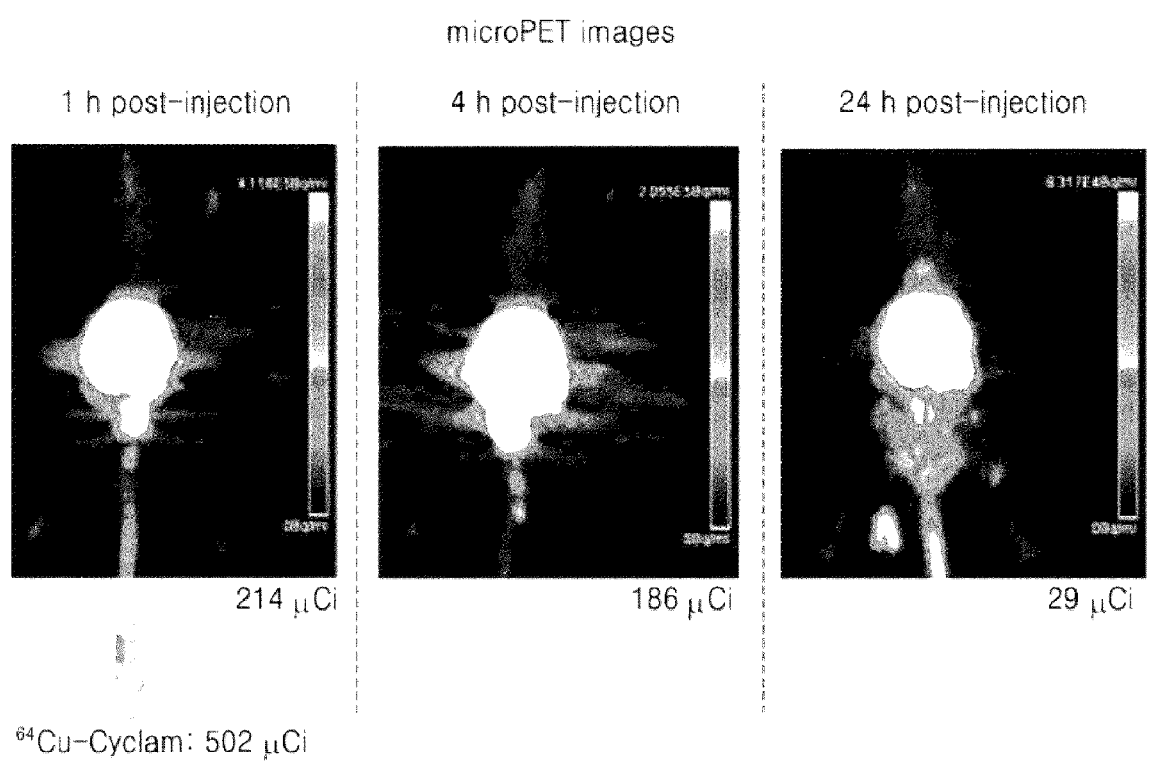
Figure 11B:
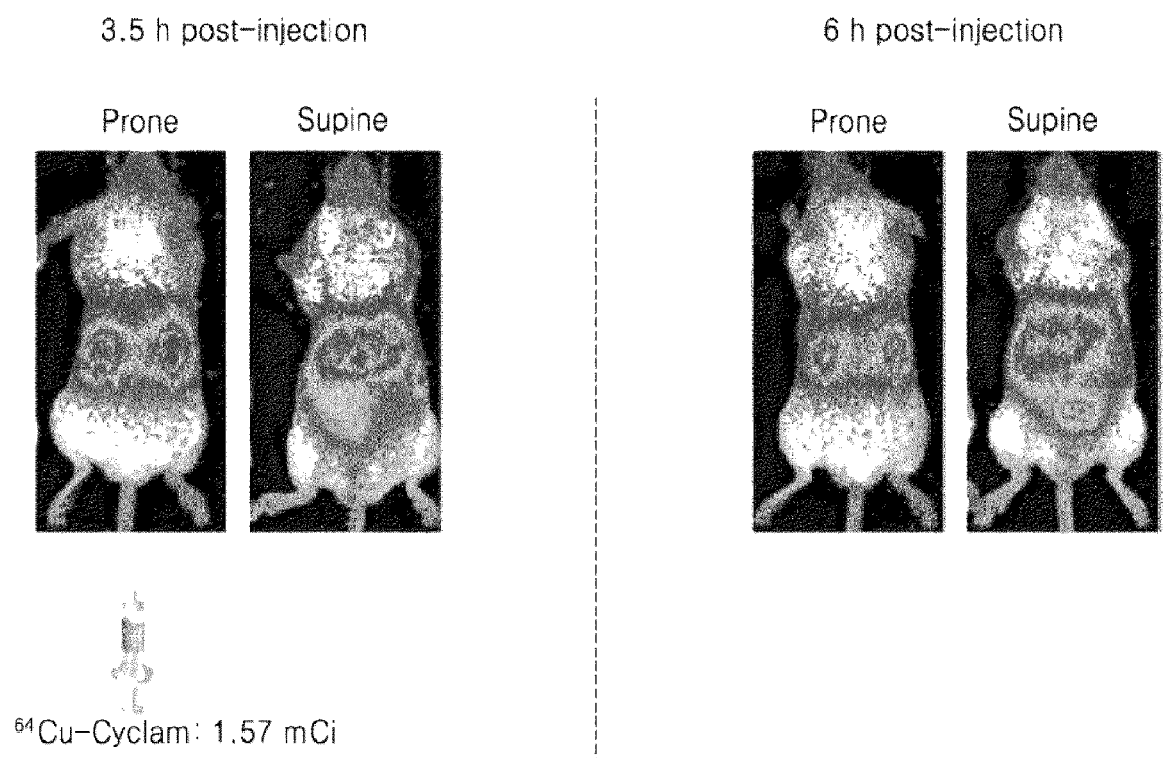
Figure 12:
FIG. 12 shows the degree of inflammation in the joint regions of arthritis animal models according to a specific embodiment of the present disclosure.

As shown in FIGS. 6A to 6C, higher uptake of $^{64}$Cu-labeled TACN of Example 20 was observed in the inflamed paw than in the opposite paw when imaging was performed after 1 hour, and the same result was also observed in PET imaging. The inflamed site was also detected in imaging immediately after injection of $^{64}$Cu-labeled TACN of Example 20.

In addition, selective uptake of $^{64}$Cu-labeled complex compound of Examples 2, 3, 14 or 21 according to the present disclosure in inflamed sites was also observed in optical imaging and nuclear medicine imaging, as shown in FIGS. 7A to 7D and FIGS. 8A to 8E.

Meanwhile, as shown in FIGS. 9A to 9B and FIGS. 10A to 10B, higher uptakes of $^{64}$Cu-labeled compounds 1g and 1i of Examples 7 and 9 in the inflamed paw than in the opposite paw were observed in the optical and nuclear medicine imaging which were performed 2 hours later.

Meanwhile, as shown in FIGS. 11A to 11D, $^{64}$Cu-labeled cyclam of Example 16 showed no obvious difference in the inflamed and normal paws, and its injection showed low uptake, compared to injection of the same quantity of $^{64}$Cu-labeled cyclen of Example 1.

(2) Arthritis Model

Figure 13A:
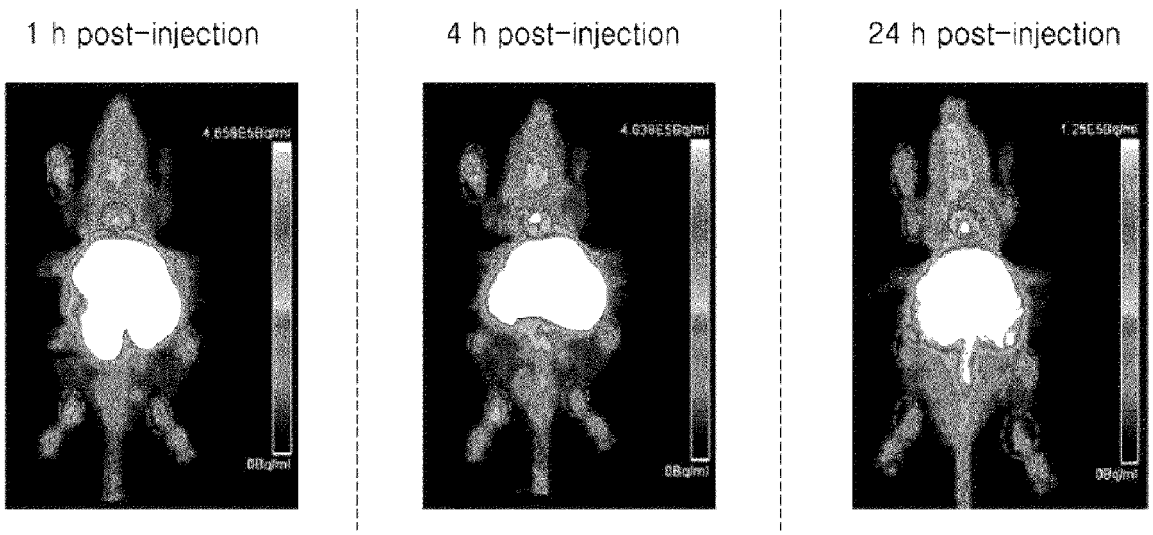
FIGS. 13A and 13B show results of imaging arthritis models injected with the $^{64}$Cu-labeled complex compound of Example 1 according to a specific embodiment of the present disclosure.
Figure 13B:
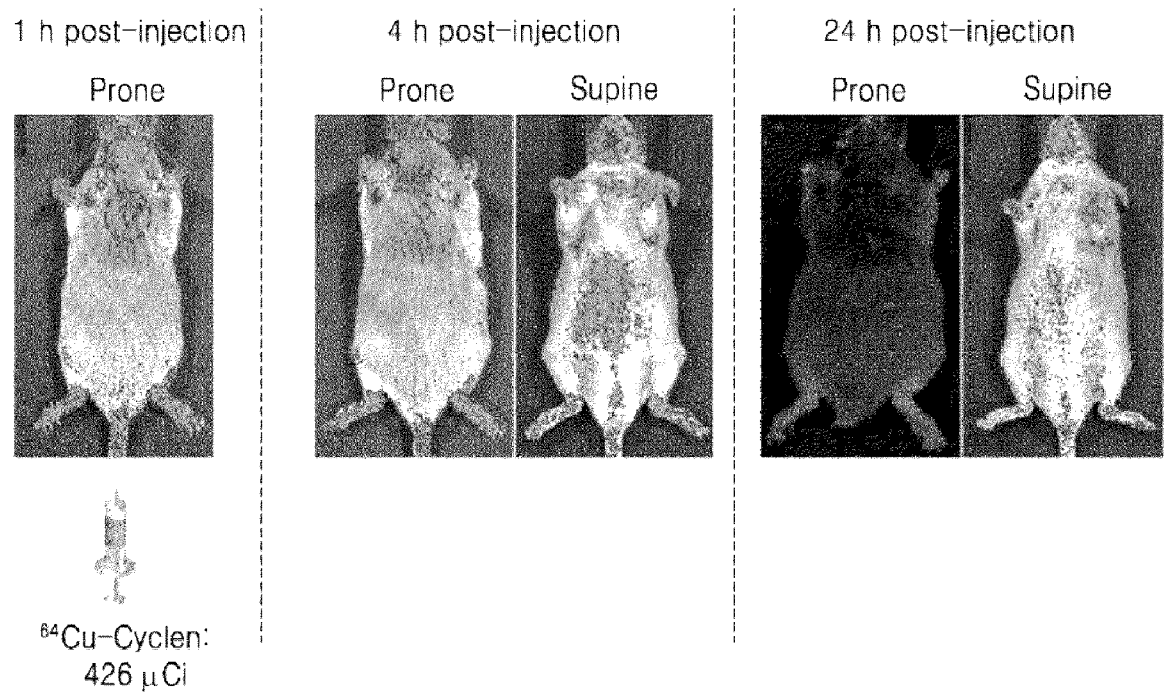

When $^{64}$Cu-labeled cyclen of Example 1 according to the present disclosure was injected into the arthritis model, selective uptake in the joint region was observed, as shown in FIGS. 13A and 13B.

(3) Brain Inflammation Model

Inflammation was induced by injecting LPS into the half of the rat's brain, and 1 day later, $^{64}$Cu-labeled complex compound of Example 17 according to the present disclosure was injected, followed PET imaging. As shown in FIG. 14, higher uptake was observed in the inflamed site than in the opposite site.

Experimental Example 6: Imaging Study in Myocardial Infarction Model

It is known that myocardial infarction sites show high concentrations of hydrogen sulfide. Thus, after induction of myocardial infarction by coronary artery occlusion in rats, 50 μCi-900 μCi of the $^{64}$Cu-labeled complex compound was injected via the tails of the rats, and uptake in the myocardial infarction site was examined over time by PET imaging.

2 days after injection of the $^{64}$Cu-labeled complex compound, [$^{18}$F]FDG was injected, and PET imaging was performed to examine whether myocardial infarction was properly induced.

36 hours after establishment of the myocardial infarction model, 730 μCi of the radioisotope-labeled complex compound of the present disclosure was injected and nuclear medicine imaging was performed. 2 days later, 1.06 μCi of FDG was injected into the same rat, and then FDG-PET images were obtained. Results are shown in FIGS. 15 to 17 (in the nuclear medicine imaging, the upper image represents a transverse image, and the lower image represents a coronal image).

Figure 15:
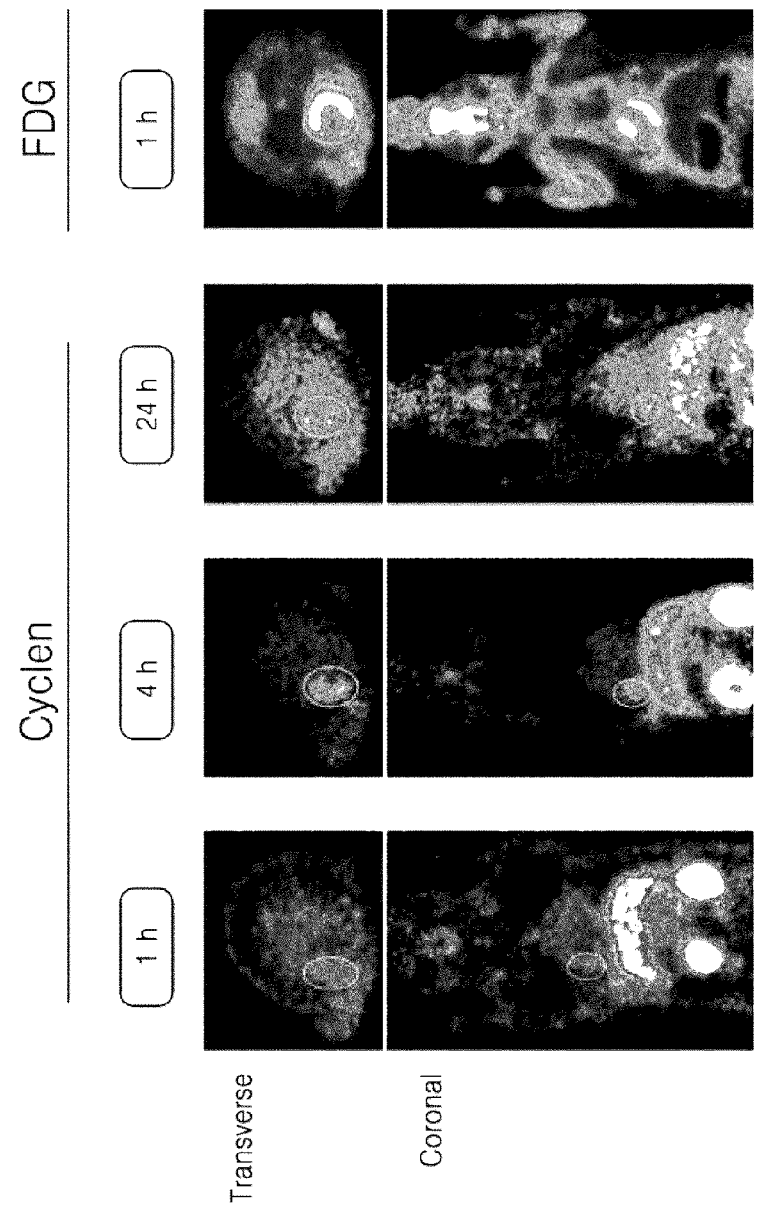
FIG. 15 shows result of imaging myocardial infarction models injected with the $^{64}$Cu-labeled complex compound of Example 1 according to a specific embodiment of the present disclosure.

As shown in FIG. 15, in the image taken at 24 hours after injection of $^{64}$Cu-labeled cyclen of Example 1 according to the present disclosure, high uptake was detected in the myocardial infarction site such that the myocardial infarction site was clearly observed. In contrast, when FDG was injected, FDG uptake did not occur in the myocardial infarction site, and therefore, the cardiac muscles was observed not as donut-shaped rings but as partially broken rings.

Figure 16:
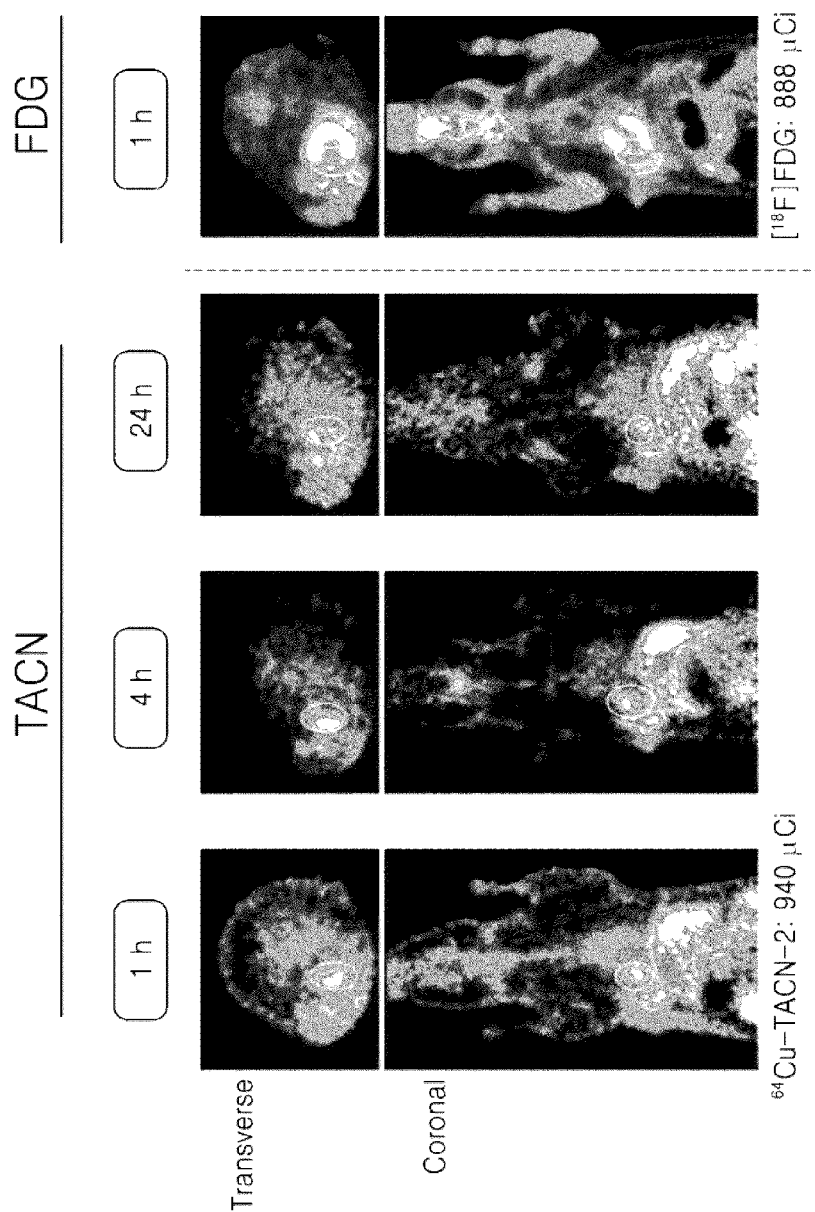
FIG. 16 shows result of imaging myocardial infarction models injected with the $^{64}$Cu-labeled complex compound of Example 20 according to a specific embodiment of the present disclosure.

As shown in FIG. 16, when $^{64}$Cu-labeled TACN compound of Example 20 was injected, the myocardial infarction site was clearly observed.

Figure 17:
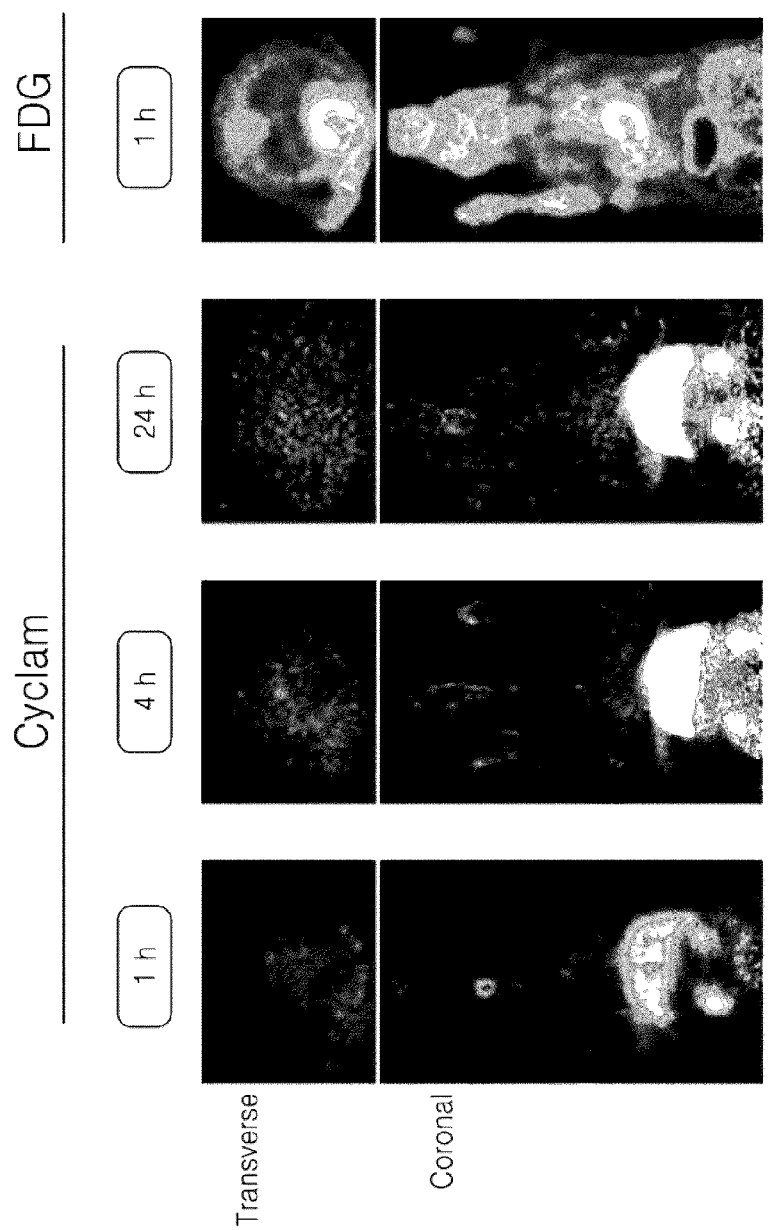
FIG. 17 shows result of imaging myocardial infarction models injected with the $^{64}$Cu-labeled complex compound of Example 16 according to a specific embodiment of the present disclosure.
Figure 18:
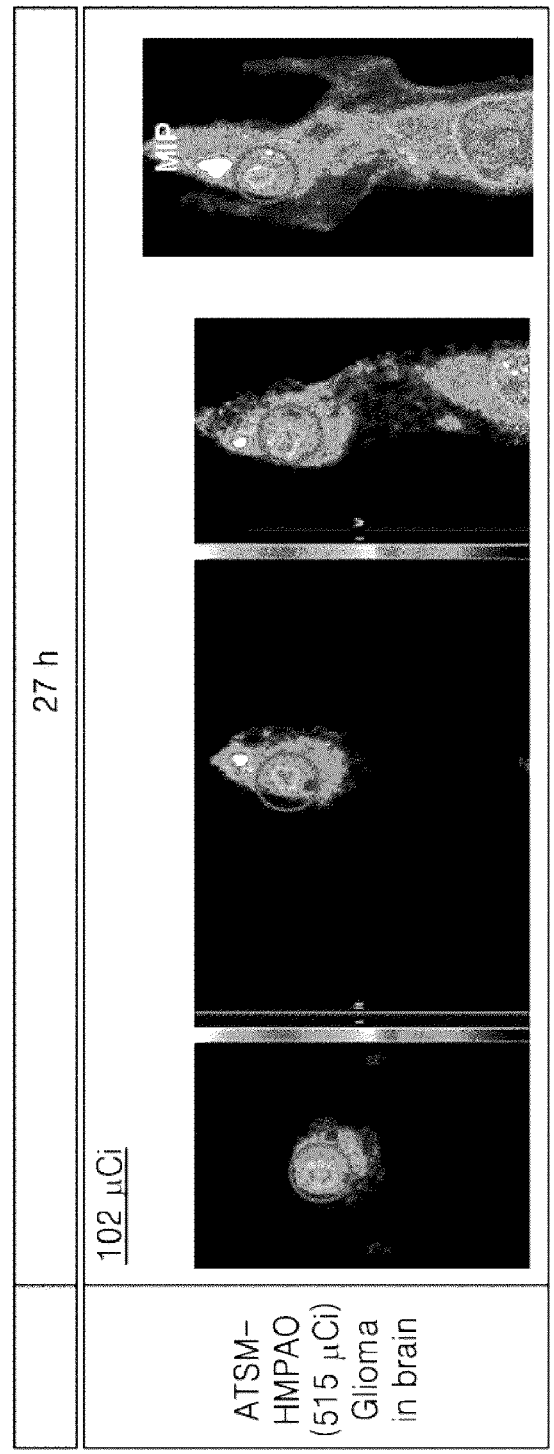
FIG. 18 shows result of imaging brain tumor models injected with the $^{64}$Cu-labeled complex compound of Example 17 according to a specific embodiment of the present disclosure.

As shown in FIG. 17, when $^{64}$Cu-labeled cyclam of Example 16 was injected, no specific uptake was observed in the heart, as in the above paw inflammation and arthritis models.

Experimental Example 7: Imaging Study in Brain Tumor Model

PET images were obtained at 72 hours after injecting the $^{64}$Cu-labeled 1q compound of Example 17 into the prepared brain tumor rat model. High uptake was observed in the brain tumor, and this imaging study suggests that brain tumor may be diagnosed by using the probe for detecting hydrogen sulfide.

Experimental Example 8: Imaging Study in Various Tumor Models

Figure 19A:
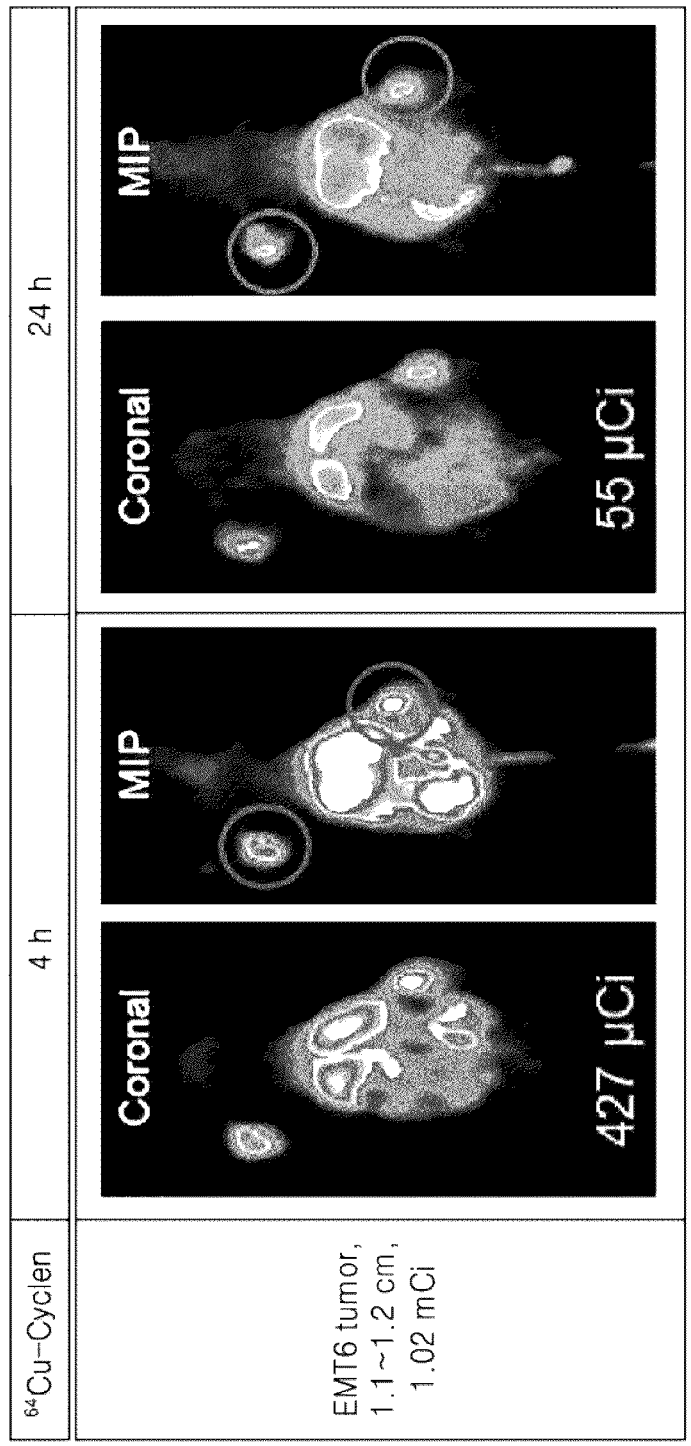
FIGS. 19A and 19B show results of imaging tumor (EMT6) (19A) and tumor (CT26) (19B) injected with the $^{64}$Cu-labeled complex compound of Example 1 according to a specific embodiment of the present disclosure, respectively.
Figure 19B:
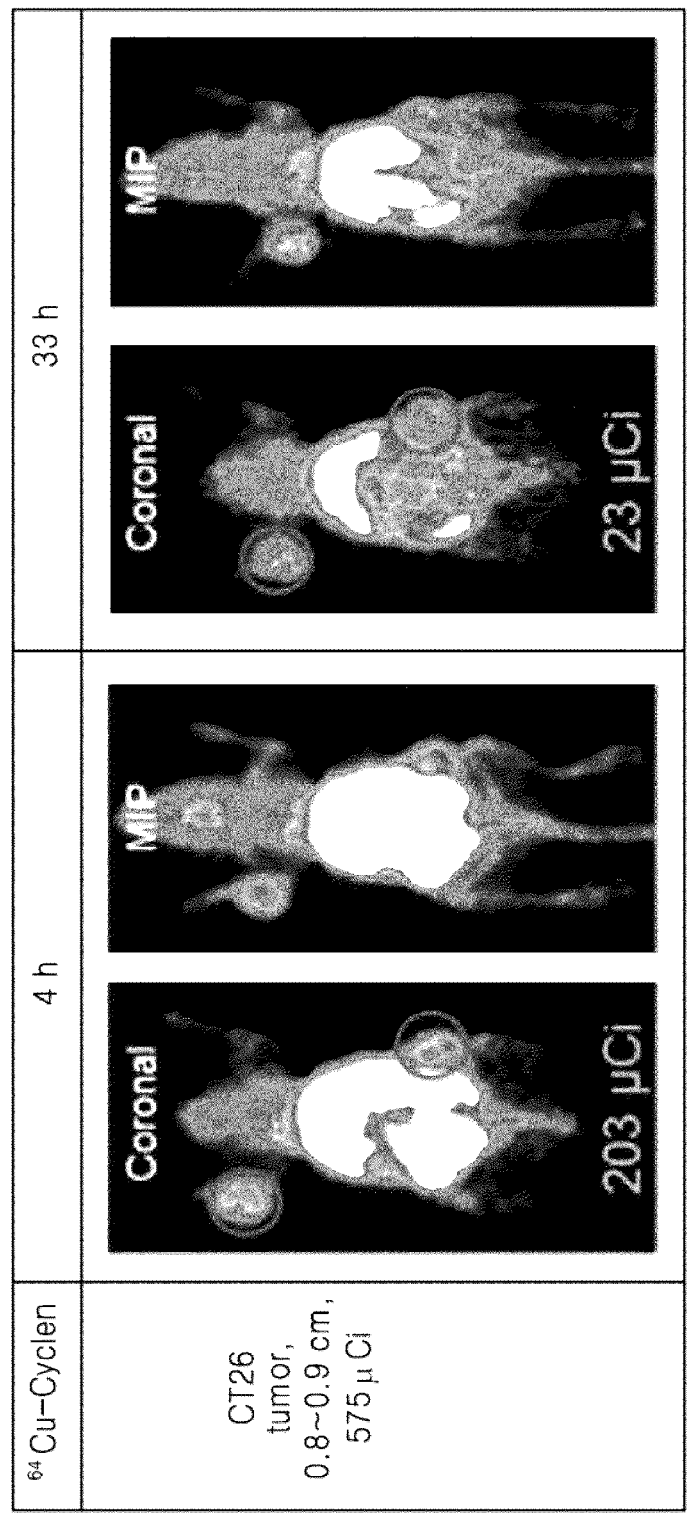

PET images were obtained after injecting the $^{64}$Cu-labeled complex compound of Example 1 into the prepared rat model having EMT6 tumor and rat model having CT26 tumor. Results are shown in FIGS. 19A and 19B. Referring to FIGS. 19A and 19B, higher uptake was observed in the tumor region (red circle) than in the background, suggesting that the probe for detecting hydrogen sulfide may be used in the diagnosis of various tumors. In particular, since EMT6 tumor is commonly used as a hypoxic tumor model, the probe may be suggested as a probe applicable to detection of hypoxia in tumors.

Experimental Example 9: Imaging Study in Pancreatitis Model

Figure 20:
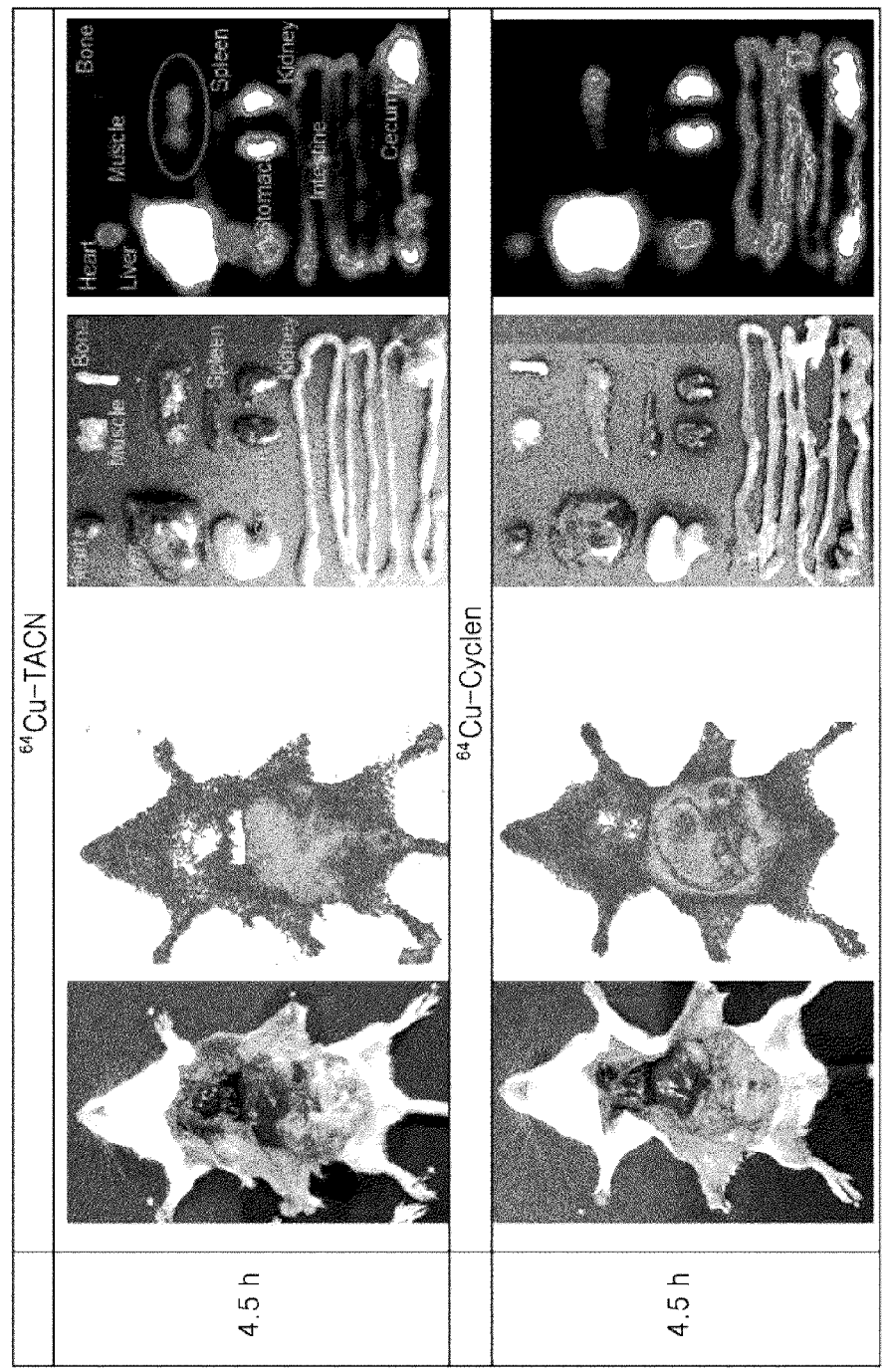
FIG. 20 shows result of imaging pancreatitis models injected with the $^{64}$Cu-labeled complex compounds of Example 1 or Example 20 according to the present disclosure.

Optical images were obtained after injecting each of the $^{64}$Cu-labeled complex compounds of Example 1 and Example 20 into the prepared rat models having pancreatitis, and PET images were obtained after excision of tissues thereof. Results are shown in FIG. 20. Referring to FIG. 20, high uptakes of the $^{64}$Cu-labeled complex compounds of Example 1 and Example 20 were observed in the pancreas (red oval) of the pancreatitis models, suggesting that the probe of the present disclosure may be used to diagnose pancreatitis.

Experimental Example 10: Imaging Study in Sepsis Model

Figure 21:
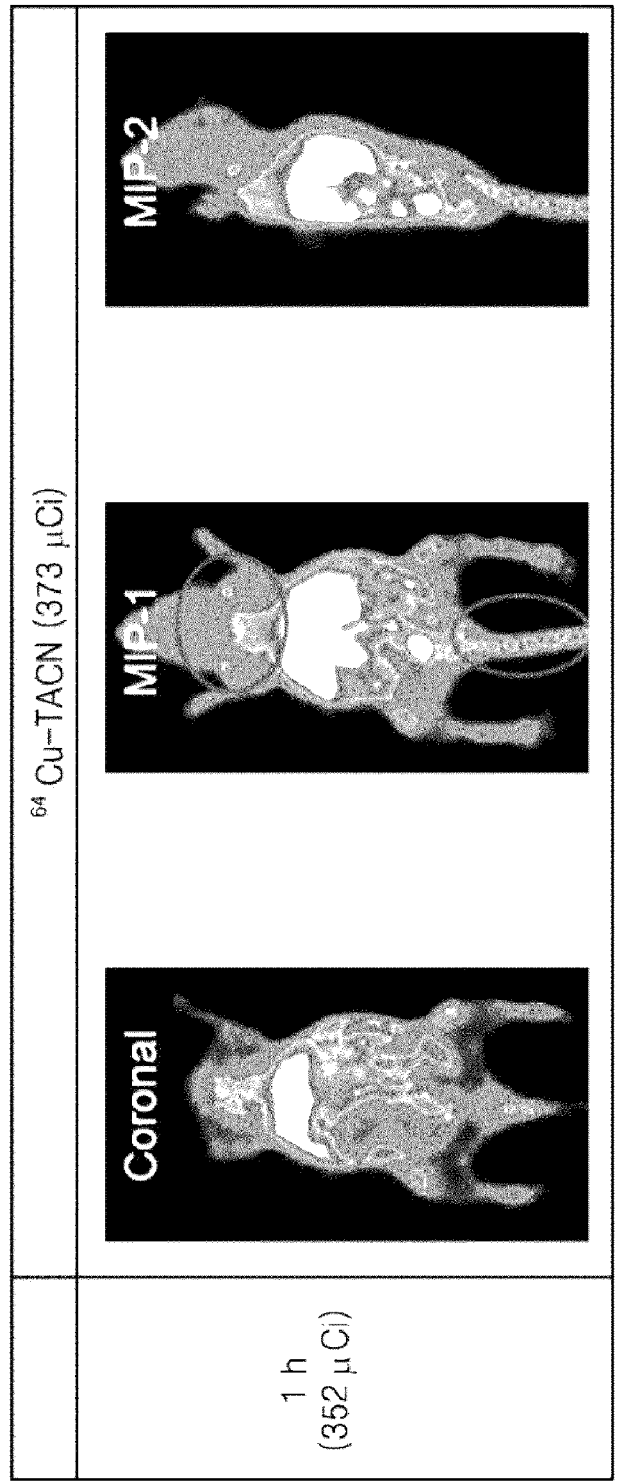
FIG. 21 shows result of imaging sepsis models injected with the $^{64}$Cu-labeled complex compound of Example 20 according to the present disclosure.

PET images were obtained after injecting the $^{64}$Cu-labeled complex compound of Example 20 into the prepared rat model having sepsis. Result is shown in FIG. 21. Referring to FIG. 21, uptake was increased throughout the body of the sepsis model. In particular, increased uptake was observed in the lung, suggesting that the probe for detecting hydrogen sulfide may be used in the diagnosis of sepsis.

Experimental Example 11: Imaging Study of Hydrogen Sulfide in Normal Rat

Figure 22:
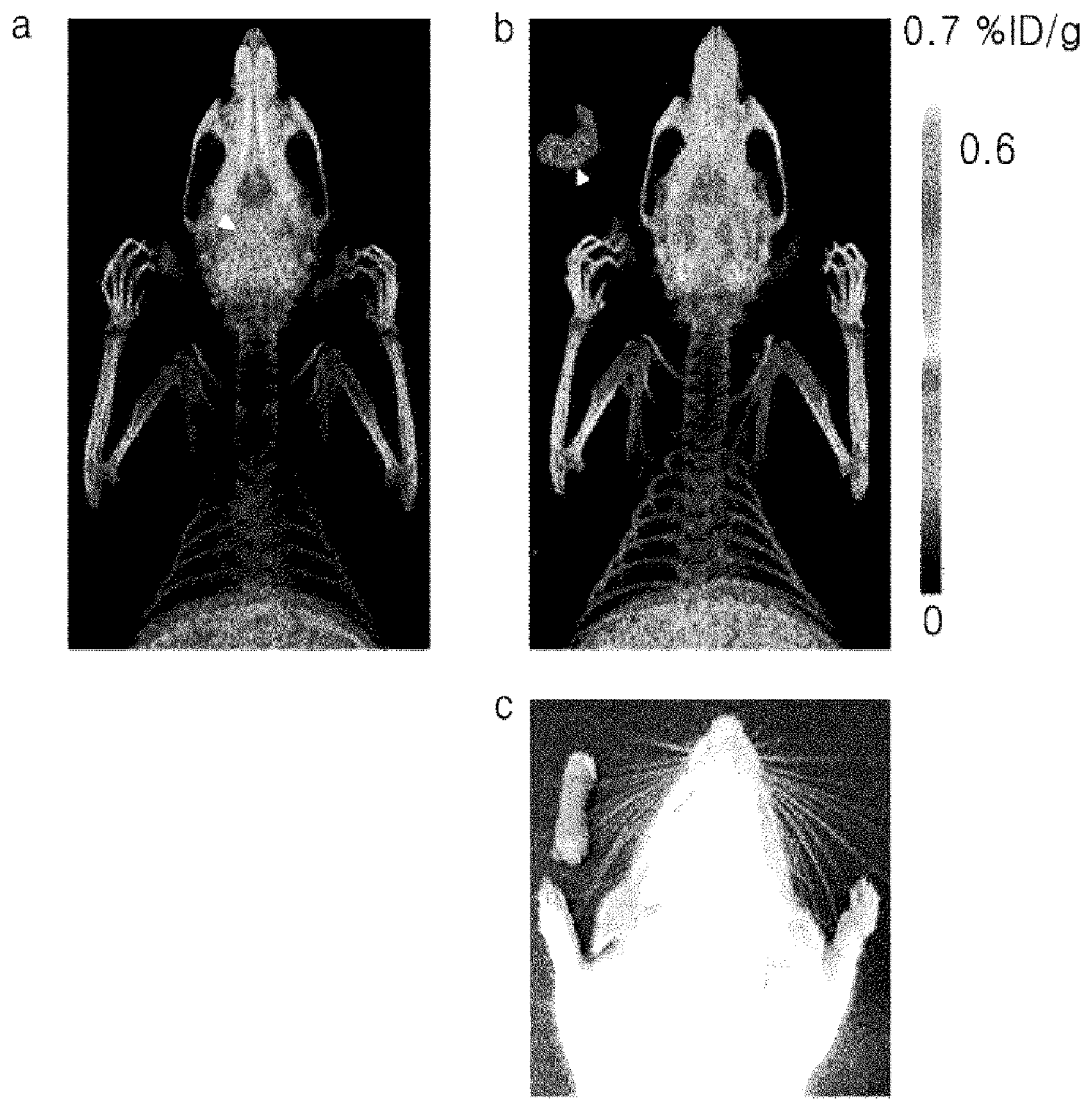
FIG. 22 is a PET image showing a high concentration of hydrogen sulfide in the tongue of a normal rat injected with the $^{64}$Cu-labeled complex compound of Example 1 according to the present disclosure, indicating that the $^{64}$Cu-labeled complex compound of Example 1 according to the present disclosure is used to easily detect a site having a high concentration of in vivo hydrogen sulfide.

PET images were obtained after injecting the $^{64}$Cu-labeled complex compound of Example 1 into a normal rat, and PET images were obtained again after excision of the tongue thereof. Results are shown in FIG. 22. In PET image before excision of the tongue (A), high uptake was observed in the tongue. However, after excision (B), the uptake was decreased in the same site. Further, high uptake was observed in the tongue removed by excision. (C) is a photograph taken before imaging the tongue after excision.

These results suggest that the probe for detecting hydrogen sulfide may be used in the detection of hydrogen sulfide under a normal condition as well as under a disease condition.

Figure 23:
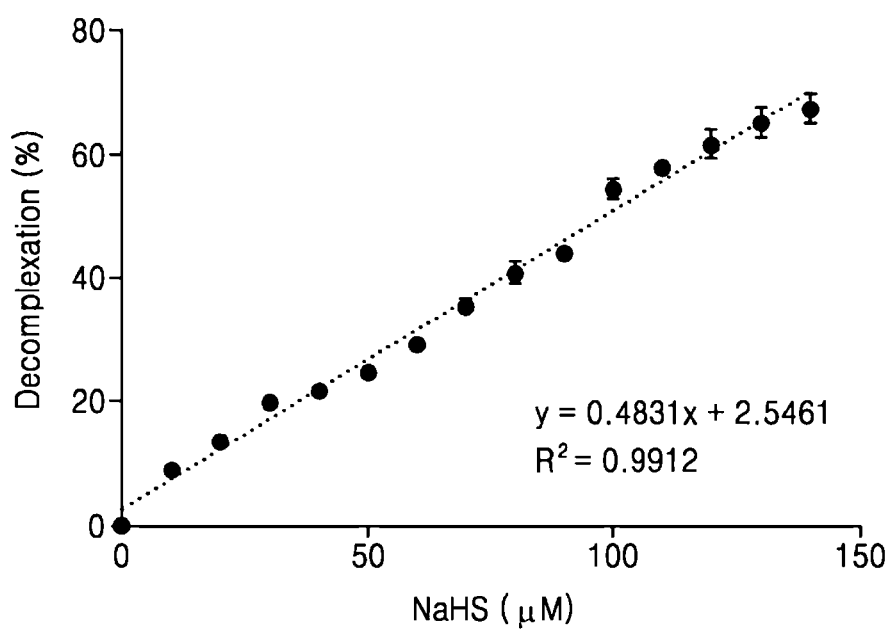
FIG. 23 shows a graph quantifying decomplexation by reacting the $^{64}$Cu-labeled complex compound of Example 20 according to the present disclosure with hydrogen sulfide at different concentrations, indicating that there is excellent correlation between the $^{64}$Cu-labeled complex compound according to the present disclosure and hydrogen sulfide.

Experimental Example 12: Calibration Study of Hydrogen Sulfide $^{64}$Cu-labeled TACN of Example 20 according to the present disclosures was reacted with various concentrations of NaHS which is a source of hydrogen sulfide, and decomplexation was measured to obtain a calibration curve, as shown in FIG. 23. There was a very excellent correlation therebetween, suggesting that concentrations of hydrogen sulfide may be accurately determined by measuring decomplexation.

Experimental Example 13: Comparison with Common Method of Measuring Hydrogen Sulfide Concentrations In order to demonstrate that the complex compound for detecting hydrogen sulfide according to the present disclosure specifically detects a model having a specific disease showing a higher concentration of hydrogen sulfide than a normal rat, data obtained by using the $^{64}$Cu-labeled complex compound of Example 20 and a common methylene blue method were compared.

The obtained data were shown in the following Table 7 and FIG. 24.

TABLE 7

|  | Normal rat | Standard deviation | Myocardial infarction model | Standard deviation |
|---|---|---|---|---|
| $^{64}$Cu-TACN | 23.6 | 3.9 | 41.8 | 2.0 |
| Methylene blue | 23.8 | 7.0 | 40.3 | 2.0 |

Figure 24:
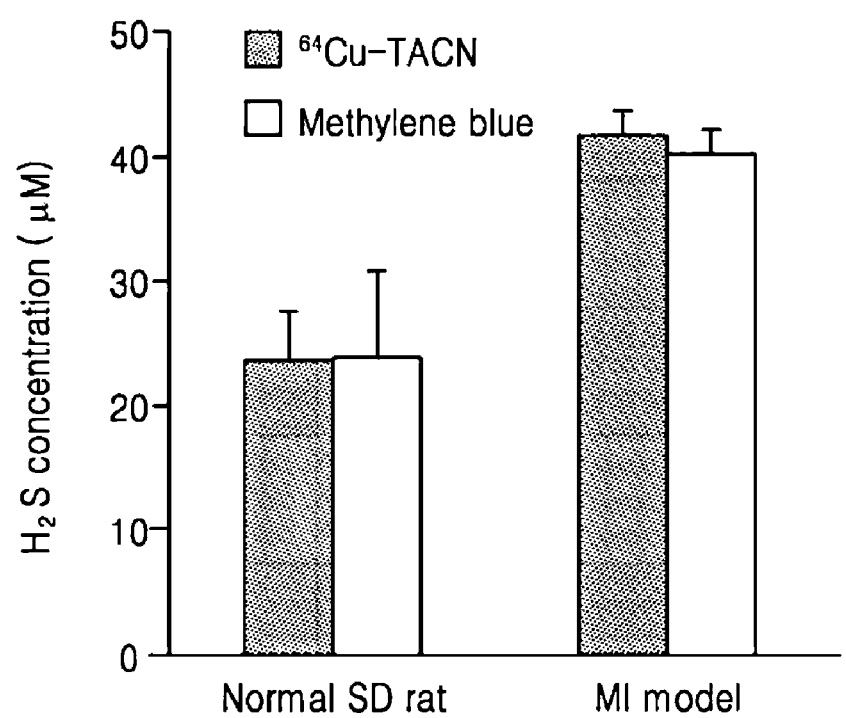
FIG. 24 shows a graph of hydrogen sulfide concentrations in the plasmas of a normal rat and a myocardial infarction model rat, which were measured by using the $^{64}$Cu-labeled complex compound of Example 20 according to the present disclosure, in which the $^{64}$Cu-labeled complex compound of Example 20 according to the present disclosure showed measured values very similar to those of a known methylene method, and the myocardial infarction model showed a very high plasma concentration of hydrogen sulfide, as compared with the normal rat.

Referring to Table 7 and FIG. 24, the complex compound for detecting hydrogen sulfide according to the present disclosure may specifically detect a myocardial infarction model generating hydrogen sulfide, which is comparable to the common methylene blue method.

The invention claimed is:

1. A probe for detecting hydrogen sulfide (H$_2$S), comprising a radioactive isotope Cu-introduced complex compound which is represented by the following Chemical Formula 2, wherein the complex compound reacts with the hydrogen sulfide to form a copper sulfide and is comprised in a dose of 50 μCi/kg-1000 μCi/kg, based on a dose immediately before use:

[Chemical Formula 2]

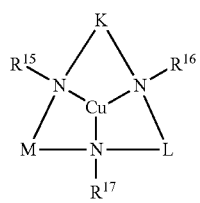

2

(wherein K, L and M are each independently one or more selected from  =C(R$^{18}$)(R$^{19}$)—C(R$^{20}$)(R$^{21}$)—,  =C(R$^{18}$)—C(R$^{19}$)(R$^{20}$)—C(R$^{21}$)(R$^{22}$)—,  C(R$^{18}$)(R$^{19}$)—C(R$^{20}$)(R$^{21}$)—C(R$^{22}$)(R$^{23}$)—, and =C(R$^{18}$)—C(R$^{19}$)=;

R$^{15}$ to R$^{23}$ are each independently one or more selected from hydroxy, substituted or unsubstituted C$_1$-C$_{20}$ linear or branched alkyl, substituted or unsubstituted C$_1$-C$_6$ linear or branched alkyloxycarbonyl, substituted or unsubstituted C$_5$-C$_{12}$ aryl C$_1$-C$_6$ alkyl, substituted or unsubstituted C$_5$-C$_{12}$ heterocycloalkyl, substituted or unsubstituted C$_5$-C$_{20}$ aryl, substituted or unsubstituted C$_5$-C$_{20}$ arylsulfonyl, C$_1$-C$_6$ alkylamine, C$_1$-C$_6$ dialkylamine, and substituted or unsubstituted amine, the 'substituted' means being substituted with one or more substituents selected from hydroxy, hydroxy C$_1$-C$_6$ alkyl, C$_1$-C$_6$ dialkylamine, nitro, and $^{64}$Cu-labeled 3-methyl-1, 4, 7, 10-tetraazacyclotridecane;

Cu is any one selected from $^{60}$Cu, $^{61}$Cu, $^{62}$Cu, $^{64}$Cu, and $^{67}$Cu).

2. The probe for detecting H$_2$S of claim 1, wherein the complex compound of Chemical Formula 2 is used in one or more selected from a contrast agent for positron emission tomography (PET), a contrast agent for gamma camera, single photon emission computed tomography (SPECT), or Cherenkov optical imaging, a contrast agent for charge-coupled device (CCD), a contrast agent for magnetic resonance imaging (MRI), computed tomography (CT), and ultrasound (US).

3. A method of measuring, detecting or imaging hydrogen sulfide in a cell or tissue comprising administering the probe for detecting hydrogen sulfide comprising the radioactive isotope Cu-introduced complex compound of claim 1, and measuring, detecting or imaging hydrogen sulfide.

4. The method of measuring, detecting or imaging hydrogen sulfide in a cell or a tissue of claim 3, wherein the imaging of hydrogen sulfide is performed by measuring Cherenkov radiation emitted from the radioactive isotope Cu.

5. The method of measuring, detecting or imaging hydrogen sulfide in a cell of claim 4, wherein Cherenkov radiation has a wavelength of 200 nm to 1000 nm.

6. The method of measuring, detecting or imaging hydrogen sulfide in a cell or tissue of claim 3, wherein the probe for detecting hydrogen sulfide comprising the radioactive isotope Cu-introduced complex compound images hydrogen sulfide in a site where hydrogen sulfide is abnormally increased or in a cell or extracellular matrix localized to the site, after being administered.

7. A method for diagnosing diseases associated with hydrogen sulfide, comprising administering a probe for detecting hydrogen sulfide comprising the radioactive isotope Cu-introduced complex compound of claim 1 to a subject in need thereof, and performing diagnostic measurement, detection of imaging of hydrogen sulfide.

8. The method of claim 7, wherein the diseases are one or more selected from inflammatory diseases, cardiac diseases, Parkinson's disease, Alzheimer's disease, Down syndrome, tumors, sepsis, pains, arteriosclerosis, diabetes, stroke, liver cirrhosis, and asthma.

9. The method of claim 8, wherein the inflammatory diseases are one or more selected from rheumatoid arthritis, non-rheumatoid inflammatory arthritis, Lyme disease-associated arthritis, inflammatory osteoarthritis, encephalomeningitis, osteomyelitis, inflammatory bowel disease, appendicitis, pancreatitis, sepsis, pyelitis, nephritis, and inflammatory diseases caused by bacterial infections.

10. The method of claim 8, wherein the cardiac diseases are one or more selected from myocardial infarction, cardiac ischemia, angina, cardiomyopathy, and endocarditis.

11. The method of claim 8, wherein the diagnosing of tumors is to diagnose hypoxia in tumors.

\* \* \* \* \*